(12) United States Patent
Myers et al.

(10) Patent No.: US 6,492,386 B2
(45) Date of Patent: Dec. 10, 2002

(54) QUINUCLIDINE-SUBSTITUTED ARYL COMPOUNDS FOR TREATMENT OF DISEASE

(75) Inventors: Jason K. Myers, Kalamazoo, MI (US); Vincent E. Groppi, Jr., Kalamazoo, MI (US); David W. Piotrowski, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/932,325

(22) Filed: Aug. 17, 2001

(65) Prior Publication Data

US 2002/0052389 A1 May 2, 2002

Related U.S. Application Data

(60) Provisional application No. 60/226,164, filed on Aug. 18, 2000, provisional application No. 60/284,956, filed on Apr. 19, 2001, provisional application No. 60/284,971, filed on Apr. 19, 2001, and provisional application No. 60/284,968, filed on Apr. 19, 2001.

(51) Int. Cl.[7] .................. A61K 31/439; A61K 31/5377; C07D 453/02
(52) U.S. Cl. .................... 514/305; 514/233.2; 546/133; 544/127
(58) Field of Search .............................. 514/305, 233.2; 546/133; 544/127

(56) References Cited

U.S. PATENT DOCUMENTS 4,863,919 A * 9/1989 Smith .................... 514/214

* cited by examiner

Primary Examiner—Charanjit S. Aulakh
(74) Attorney, Agent, or Firm—Mary J. Hosley

(57) ABSTRACT

The invention provides compounds of Formula I:

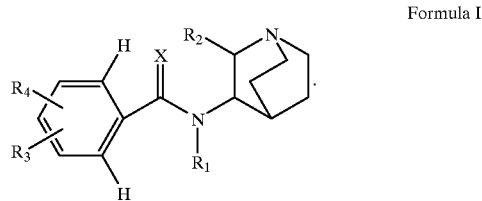

These compounds may be in the form of pharmaceutical salts or compositions, and racemic mixtures or pure enantiomers thereof. The compounds of Formula I are useful in pharmaceuticals in which α7 is known to be involved.

60 Claims, No Drawings

QUINUCLIDINE-SUBSTITUTED ARYL COMPOUNDS FOR TREATMENT OF DISEASE

CROSS REFERENCE TO RELATED APPLICATIONS

This application claims the benefit of US provisional application Ser. No. 60/226,164 filed on Aug. 18, 2000, under 35 USC 119(e)(i) and U.S. provisional applications Ser. No. 60/284,956, Ser. No. 60/284,971, and Ser. No. 60/284,968 all filed on Apr. 19, 2001, under 35 USC 119(e)(i), which are incorporated herein by reference in their entirety.

FIELD OF INVENTION

Nicotinic acetylcholine receptors (nAChRs) play a large role in central nervous system (CNS) activity. Particularly, they are known to be involved in cognition, learning, mood, emotion, and neuroprotection. There are several types of nicotinic acetylcholine receptors, and each one appears to have a different role in regulating CNS function. Nicotine affects all such receptors, and has a variety of activities. Unfortunately, not all of the activities are desirable. In fact, one of the least desirable properties of nicotine is its addictive nature and the low ratio between efficacy and safety. The present invention relates to molecules that have a greater effect upon the α7 nAChRs as compared to other closely related members of this large ligand-gated receptor family. Thus, the invention provides compounds that are active drug molecules with fewer side effects.

BACKGROUND OF THE INVENTION

U.S. Pat. No. 5,977,144 discloses compositions for benzylidene- and cinnamylidene-anabaseines and methods for using these compositions for treating conditions associated with defects or malfunctioning of nicotinic subtypes brain receptors. These compositions target the α7 receptor subtype with little or no activation of the α4β2 or other receptor subtypes.

U.S. Pat. No. 5,919,793 discloses heterocyclic derivatives useful in lowering cholesterol levels in blood plasma.

U.S. Pat. No. 5,837,489 discloses human neuronal nicotinic acetylcholine receptor and cells transformed with same DNA and mRNA encoding subunits.

U.S. Pat. No. 5,741,819 discloses arylsulfonylbenzene derivatives and their use as factor Xa inhibitors as being useful for the treatment of arterial and venous thrombotic occlusive disorders, inflammation, cancer, and neurodegenerative diseases.

U.S. Pat. No. 5,723,103 discloses substituted benzamides and radioligand analogs and methods of using the compounds for the identification of 5-$HT_3$ receptors and the detection and treatment of abnormal conditions associated therewith.

U.S. Pat. No. 5,561,149 discloses the use of a mono or bicyclic carbocyclic, or heterocyclic carboxylic, acid ester or amide or an imidazolyl carbazol in the manufacture of a medicament suitable for the treatment of stress-related psychiatric disorders, for increasing vigilance, for the treatment of rhinitis or serotonin-induced disorders and/or coadministration with another active agent to increase the bioavailability thereof, or for nasal administration.

U.S. Pat. No. 5,491,148 discloses isoquinolinones and dihydroisoquinolinones which are 5-$HT_3$ receptor antagonists.

U.S. Pat. No. 5,290,938 discloses optical active forms of the carboxylic acid amines of 3-aminoquinuclidine, generally N-(aminoquinuclidinyl-3)-alkylamides where alkyl is a linear or branched hydrocarbon chain of the general formula $C_nH_(2n+1)$, preferably $CH_3$ or $C_2H_5$, and the preparation thereof. These can be hydrolyzed to the optical active forms of 3-aminoquinuclidine.

U.S. Pat. No. 5,273,972 discloses novel 2-substituted-3-quinuclidinyl arylcarboxamides and arylthiocarboxamides and corresponding arylcarboxylates which have utility as therapeutic agents which exhibit gastric prokinetic, antiemetic, anxiolytic and 5-HT (serotonin) antagonist effects in warm blooded animals.

U.S. Pat. No. 5,246,942 discloses certain dibenzofurancarboxamides and their use as 5-$HT_3$ antagonists having unique CNS, anti-emetic and gastric prokinetic activity void of any significant $D_2$ receptor binding properties.

U.S. Pat. No. 5,237,066 discloses enantiomers of absolute configuration S of amide derivatives of 3-aminoquinuclidine, the process for preparing them and their use as medicinal products having activity in respect of gastric movements and antiemetic activity.

U.S. Pat. No. 5,236,931 discloses novel 3-quinuclidinyl benzamides and benzoates which have utility as therapeutical agents which exhibit anxiolytic, antipsychotic, cognition improvement, antiemetic and gastric prokinetic effects in warm blooded animals.

U.S. Pat. No. 5,206,246 discloses anxiolytic-R-N-(1-azabicyclo[2.2.2]oct-3-yl)-benzamides and thiobenzamides, their N-oxides and pharmaceutically acceptable salts thereof. A preferred compound is R-(+)-4-amino-N-(l-azabicyclo[2.2.2]oct-3-yl)-5-chloro-2-methoxybenzamide.

U.S. Pat. No. 5,183,822 discloses new heterocyclic compounds (3,4-annelated benzimidazole-2(11)-ones) having an antagonistic activity on 5-hydroxytryptamine (5-HT) receptors.

U.S. Pat. No. 5,175,173 discloses carboxamides useful as antiemetic or antipsychotic agents.

U.S. Pat. No. 5,106, 843 discloses heterocyclic compounds useful as 5-$HT_3$ antagonists.

U.S. Pat. No. 5,084,460 discloses methods of therapeutic treatment with N-(3-quinuclidinyl)-2-hydroxybenzamides and thiobenzamides. The therapeutic agents are disclosed as exhibiting anxiolytic antipsychotic and cognitive improving effects in warm blooded animals.

U.S. Pat. No. 5,070,095 discloses novel I-(azabicyclo [2.2.2]oct-3- or -4-yl)-benzamides substituted on the benzene ring with the basic substituted aminomethyleneamino group which has been found to be useful in treating emesis, including emesis due to chemical and radiation anticancer therapy, anxiety, and impaired gastric emptying.

U.S. Pat. No. 5,057,519 discloses 5-$HT_3$ antagonists as being useful in reducing opiate tolerance.

U.S. Pat. No. 5,039,680 disclose 5-$HT_3$ antagonists in preventing or reducing dependency on dependency-inducing agents.

U.S. Pat. No. 5,025,022 discloses a method of treating or preventing schizophrenia and/or psychosis using S-N-(1-azabicyclo[2.2.2]oct-3-yl)-benzamides and thiobenzamides, their N-oxides and pharmaceutically acceptable salts thereof. A preferred compound is S(−)-4-amino-N-(1-azabicyclo[2.2.2]oct-3-yl)-5-chloro-2-methoxybenzamide.

U.S. Pat. No. 5,017,580 discloses memory enhancing-R-N-(1-azabicyclo[2.2.2.]oct-3-yl)-benzamides and thiobenzamides, their N-oxides and pharmaceutically acceptable salts thereof. A preferred compound is R-(+)-4-amino-N-( 1-azabicyclo[2.2.2]oct-3-yl)-5-chloro-2-methoxybenzamide.

U.S. Pat. No. 4,921,982 discloses 5-halo-2,3-dihydro-2,2-dimethylbenzofuran-7-carboxylic acids which are useful as intermediates for 5-HT$_3$ antagonists.

U.S. Pat. No. 4,908,370 discloses anxiolytic-N-(1-azabicyclo[2.2.2]oct-3-yl)-benzamides and thiobenzamides as having anxiolytic activity, in particular, activity against anxiety induced by the withdrawal from ingested substances such as narcotics.

U.S. Pat. No. 4,877,794 discloses 2-alkoxy-N-(1-azabicyclo[2.2.2]oct-3-yl)-benzamide and thiobenzamide compositions and the use thereof to treat schizophrenia.

U.S. Pat. No. 4,877,780 discloses antiemetic N-substituted benzamides having pharmaceutical properties rendering them useful as antiemetic agents with reduced undesirable side effects.

U.S. Pat. No. 4,870,181 discloses a process for the preparation of 2-alkoxy-N-(1-azabicyclo[2.2.2])octan-3-yl)-aminobenzamide.

U.S. Pat. No. 4,835,162 discloses agonists and antagonists to nicotine as smoking deterrents.

U.S. Pat. No. 4,820,715 discloses anti-emetic quinuclidinyl benzamides. The compounds are particularly useful in the treatment of chemotherapy-induced emesis in cancer patients. Some of the compounds are also useful in disorders relating to impaired gastric motility.

U.S. Pat. No. 4,803,199 discloses pharmaceutically useful heterocyclic acid esters and amides or alkylene bridged peperidines as serotonin M antagonists.

U.S. Pat. No. 4,798,829 discloses 1-azabicyclo[3.2.2]nonane derivatives having gastric motility enhancing activity and/or anti-emetic activity and/or 5-HT receptor antagonist activity.

U.S. Pat. No. 4,721,720 discloses a method of treating emesis, anxiety and/or irritable bowel syndrome.

U.S. Pat. No. 4,717,563 discloses 2-alkoxy-N-(1-azabicyclo[2.2.2]oct-3-yl) benzamides and thiobenzamides in a method for alleviating emesis caused by non-platinum anticancer drugs.

U.S. Pat. No. 4,657,911 discloses 3-amino quinuclidine derivatives and the application thereof as accelerators of gastro-intestinal motor function and as medicament potentiators.

U.S. Pat. No. 4,605,652 discloses a method of enhancing memory or correcting memory deficiency with arylamido (and arylthioamido)-azabicycloalkanes, and the pharmaceutically acceptable acid addition salts, hydrates and alcoholates thereof.

U.S. Pat. No. 4,593,034 discloses 2-alkoxy-N-(1-azabicyclo[2.2.2]oct-3-yl)-benzamides and thiobenzamides having gastrokinetic and anti-emetic activity.

U.S. Pat. No. 4,093,734 discloses amino-benzoic acid amides useful as anxiolytics, anticonvulsives, antiemetics and antiulcerogenics.

U.S. Pat. No. 3,702,324 discloses 3,4,5-trimethoxybenzamides of substituted anilines and of alkylpiperidines which exert a specific effect on the central nervous system and a somewhat lesser effect on muscle function, and thus have utility as tranquilizers.

WO 01/36417 A 1 discloses novel N-azabicyclo-amide derivatives and use in therapy, especially in the treatment of prophylaxis of psychotic disorders and intellectual impairment disorders.

WO 00/73431 A2 discloses two binding assays to directly measure the affinity and selectivity of compounds at the α7 nAChR and the 5-HT$_3$R. The combined use of these functional and binding assays may be used to identify compounds that are selective agonists of the α7 nAChR.

WO 92/15579 discloses multicyclic tertiary amine polyaromatic squalene synthase inhibitors and method of treatment for lowering serum cholesterol levels using the compounds.

WO 92/11259 discloses azabicyclic amides or esters of halogenated benzoic acids having 5-HT$_3$ receptor antagonist activity.

EP 512 350 A2 discloses 3-(indolyl-2-carboxmido) quinuclidines useful for treating diseases characterized by an excess or enhanced sensitivity to serotonin, e.g., psychosis, nausea, vomiting, dementia or other cognitive diseases, migraine, diabetes. The compound may be used to control anxiety, aggression, depression, and pain. The compounds are disclosed as serotonin 5-HT$_3$ antagonists.

FR 2 625 678 discloses N-(quinuclidin-3-yl)-benzamides and thiobenzamides useful as diet-control agents.

In *Bioorg. & Med. Chem. Lett.* 11 (2001) 319–321, the 5-HT$_3$ antagonist tropisetron (ICS 205–930) is discussed as a potent and selective α7 nicotinic receptor partial agonist.

In Behavioral Brain Res., 113 (2000) 169–181, it is discussed that the brain α7 nicotinic receptor may be an important therapeutic target for the treatment of Alzheimer's disease using DMXBA which is known as GTS-21.

Cell surface receptors are, in general, excellent and validated drug targets. nAChRs comprise a large family of ligand-gated ion channels that control neuronal activity and brain function. These receptors have a pentameric structure. In mammals, this gene family is composed of nine alpha and four beta subunits that co-assemble to form multiple subtypes of receptors that have a distinctive pharmacology. Acetylcholine is the endogenous regulator of all of the subtypes, while nicotine non-selectively activates all nAChRs.

The α7 nAChR is one receptor system that has proved to be a difficult target for testing. Native α7 nAChR is not routinely able to be stably expressed in most mammalian cell lines (Cooper and Millar, *Nature*, 366(6454), p. 360–4, 1997). Another feature that makes functional assays of α7 nAChR challenging is that the receptor is rapidly (100 milliseconds) inactivated. This rapid inactivation greatly limits the functional assays that can be used to measure channel activity.

Recently, Eisele et al. has indicated that a chimeric receptor formed between the N-terminal ligand binding domain of the α7 nAChR (Eisele et al., *Nature*, 366(6454), p 479–83, 1993), and the pore forming C-terminal domain of the 5-HT$_3$ receptor expressed well in *Xenopus oocytes* while retaining nicotinic agonist sensitivity. Eisele et al. used the N-terminus of the avian (chick) form of the α7 nAChR receptor and the C-terminus of the mouse form of the 5-HT$_3$ gene. However, under physiological conditions the α7 nAChR is a calcium channel while the 5-HT$_3$R is a sodium and potassium channel. Indeed, Eisele et al. teaches that the chicken α7 nAChR/ mouse 5-HT$_3$R behaves quite differently than the native α7 nAChR with the pore element not conducting calcium but actually being blocked by calcium ions. WO 00/73431 A2 reports on assay conditions under which the 5-HT$_3$R can be made to conduct calcium. This assay may be used to screen for agonist activity at this receptor.

SUMMARY OF THE INVENTION

The present invention discloses compounds of the Formula I:

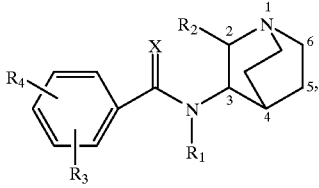

Formula I wherein X is O or S;

$R_1$ is independently selected from the group consisting of -H, alkyl, cycloalkyl, halogenated alkyl, and aryl;

Alkyl is both straight- and branched-chain moieties having from 1–6 carbon atoms;

Halogenated alkyl is an alkyl moiety having from 1–6 carbon atoms and having 1 to (2n+1) substituent(s) independently selected from —F, —Cl, —Br, or —I where n is the maximum number of carbon atoms in the moiety;

Cycloalkyl is a cyclic alkyl moiety having from 3–6 carbon atoms;

Aryl is phenyl, substituted phenyl, naphthyl, or substituted naphthyl;

Substituted phenyl is a phenyl either having 1–4 substituents independently selected from —F, —Cl, —Br, or —I, or having 1 substituent selected from -RI$_2$ and 0–3 substituents independently selected from —F, —Cl, —Br, or —I;

Substituted naphthyl is a naphthalene moiety either having 1–4 substituents independently selected from —F, —Cl, —Br, or —I, or having 1 substituent selected from —$R_{12}$ and 0–3 substituents independently selected from —F, —Cl, —Br, or —I, where the substitution can be independently on either only one ring or both rings of said naphthalene moiety;

$R_2$ is —H, alkyl, halogenated alkyl, substituted alkyl, cycloalkyl, benzyl, substituted benzyl, or aryl;

Substituted alkyl is an alkyl moiety from 1–6 carbon atoms and having 0–3 substituents independently selected from —F, —Cl, —Br, or —I and further having 1 substituent selected from —$OR_{10}$, —$SR_{10}$, —$NR_{10}R_{10}$, —$C(O)R_{10}$, —$C(O)NR_1R_{10}$, —CN, —$NR_{10}C(O)R_{10}$, —$S(O)_2NR_{10}R_{10}$—$NR_{10}S(O)_2R_{10}$, —$NO_2$, —$R_7$, —$R_9$, phenyl, or substituted phenyl;

Substituted benzyl is a benzyl either having 1–4 substituents independently selected from —F, —Cl, —Br, or —I, or having 1 substituent selected from —$R_{12}$ and 0–3 substituents independently selected from —F, —Cl, —Br, or —I, provided that all substitution is on the phenyl ring of the benzyl;

$R_3$ is selected from the group consisting of —H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, aryl, —$R_7$, —$R_9$, —$OR_8$, —$OR_{17}$, —$SR_8$, —F, —Cl, —Br, —I, —$NR_8R_8$, —$NR_{16}R_{16}$, —$C(O)R_8$, —$C(O)R_{16}$, —CN, —$C(O)NR_8R_8$, —$C(O)NR_{15}R_{15}$, —$NR_8C(O)R_8$, —$S(O)R_8$, —$OS(O)_2R_8$, —$NR_8S(O)_2R_8$, —$NO_2$, and —$N(H)C(O)N(H)R_8$;

Alkenyl is straight- and branched-chain moieties having from 2–6 carbon atoms and having at least one carbon-carbon double bond;

Halogenated alkenyl is an unsaturated alkenyl moiety having from 2–6 carbon atoms and having 1 to (2n–1) substituent(s) independently selected from —F, —Cl, —Br, or —I where n is the maximum number of carbon atoms in the moiety;

Substituted alkenyl is an unsaturated alkenyl moiety having from 2–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —$C(O)NR_{10}R_{10}$, —$NR_{10}C(O)R_{10}$, —$S(O)_2NR_{10}R_1$, —$NR_{10}S(O)_2R_{10}$—CN, phenyl, or substituted phenyl;

Alkynyl is straight- and branched-chained moieties having from 2–6 carbon atoms and having at least one carbon-carbon triple bond;

Halogenated alkynyl is an unsaturated alkynyl moiety having from 3–6 carbon atoms and having 1 to (2n–3) substituent(s) independently selected from —F, —Cl, —Br, or —I where n is the maximum number of carbon atoms in the moiety;

Substituted alkynyl is an unsaturated alkynyl moiety having from 3–6 carbon atoms and having 0–3 substituents independently selected from —F, or —Cl, and further having 1 substituent selected from —$R_7$, —$R_9$, —$OR_{10}$, —$SR_{10}$, —$NR_{10}R_0o$, —$C(O)R_{10}$, —$C(O)NR_{10}R_{10}$, —$NR_{10}C(O)R_{10}$, —$S(O)_2NR_{10}R_{10}$—$NR_{10}S(O)_2R_{10}$, —CN, phenyl, or substituted phenyl;

Halogenated cycloalkyl is a cyclic moiety having from 3–6 carbon atoms and having 14 substituents independently selected from —F, or —Cl;

Substituted cycloalkyl is a cyclic moiety having from 3–6 carbon atoms and having 0–3 substituents independently selected from —F, or —Cl, and further having 1 substituent selected from —$OR_{10}$, —$SR_{10}$, —$NR_{10}R_{10}$, —$C(O)R_{10}$, —CN, —$C(O)NR_{10}R_{10}$, —$NR_{10}C(O)R_{10}$, —$S(O)_2NR_{10}R_{10}$, —$NR_{10}S(O)_2R_1$, —$NO_2$, phenyl, or substituted phenyl;

Heterocycloalkyl is a cyclic moiety having 4–7 atoms with 1–2 atoms within the ring being —S—, —N($R_3$)—, or —O—;

Halogenated heterocycloalkyl is a cyclic moiety having from 4–7 atoms with 1–2 atoms within the ring being —S—, —N($R_3$)—, or —O-, and having 1–4 substituents independently selected from —F, or —Cl;

Substituted heterocycloalkyl is a cyclic moiety having from 4–7 atoms with 1–2 atoms within the ring being —S—, —N($R_3$)—, or —O—and having 0–3 substituents independently selected from —F, or —Cl, and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$NO_2$, —$S(O)_2NR_{10}R_{10}$, —$NR_{10}S(O)_2R_{10}$, phenyl, or substituted phenyl;

$R_4$ is selected from the group consisting of —O—$R_5$, —S—$R_5$, —S(O)—$R_5$, —C(O)—$R_5$, and alkyl substituted on the eα carbon with $R_5$ where said ω carbon is determined by counting the longest carbon chain of the alkyl moiety with the C-1 carbon being the carbon attached to the phenyl ring of the core molecule and the ω carbon being the carbon furthest from said C-1 carbon;

$R_5$ is selected from aryl, $R_7$, or $R_9$;

$R_7$ is 5-membered heteroaromatic mono-cyclic moieties containing within the ring 1–3 heteroatoms independently selected from the group consisting of —O—, =N—, —N($R_{14}$)—, and —S—, and having 0–1 substituent selected from —$R_{12}$ and 0–3 substituents independently selected from —F, —Cl, —Br, or —I, or $R_7$ is a 9-membered fused-ring moiety having a 6-membered ring fused to a 5-membered ring and having the formula

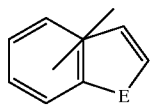

wherein E is O, S, or NR$_{14}$,

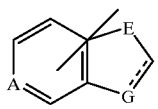

wherein E and G are independently selected from CR$_{18}$, O, S, or NR$_{14}$, and A is CR$_{18}$ or N, or

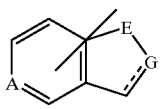

wherein E and G are independently selected from CR$_{18}$, O, S, or NR$_{14}$, and A is CR$_{18}$ or N, each 9-membered fused-ring moiety having 0–1 substituent selected from —R$_{12}$ and 0–3 substituent(s) independently selected from —F, —Cl, —Br, or —I, and having a bond directly or indirectly attached to the core molecule where valency allows in either the 6-membered or the 5-membered ring of the fused-ring moiety;

Each R$_8$ is independently selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, R$_7$, R$_9$, phenyl, or substituted phenyl;

R$_9$ is 6-membered heteroaromatic mono-cyclic moieties containing within the ring 1–3 heteroatoms selected from =N- and having 0–1 substituent selected from —R$_{12}$ and 0–3 substituent(s) independently selected from —F, —Cl, —Br, or —I, or 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from —R$_{12}$ and 0–3 substituent(s) independently selected from —F, —Cl, —Br, or —I and having a bond directly or indirectly attached to the core molecule where valency allows;

Each R$_{10}$ is independently selected from —H, alkyl, cycloalkyl, heterocycloalkyl, alkyl substituted with 1 substituent selected from R$_{13}$, cycloalkyl substituted with 1 substituent selected from R$_{13}$, heterocycloalkyl substituted with 1 substituent selected from R$_{13}$, halogenated alkyl, halogenated cycloalkyl, halogenated heterocycloalkyl, phenyl, or substituted phenyl;

Each R$_{11}$ is independently selected from —H, alkyl, cycloalkyl, heterocycloalkyl, halogenated alkyl, halogenated cycloalkyl, or halogenated heterocycloalkyl;

R$_{12}$ is selected from —OR$_{11}$, —SR$_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —NR$_{11}$R$_1$, —C(O)R$_1$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$;

R$_{13}$ is selected from —OR$_{11}$, —SR$_{11}$, —NR$_{11}$R$_{11}$, —C(O)R$_{11}$, —C(O)NR$_{11}$R$_{11}$, —CN, —CF$_3$, —NR$_{11}$C(O)R$_{11}$, —S(O)$_2$NR$_{11}$R$_{11}$, —NR$_{11}$S(O)$_2$R$_{11}$, or —NO$_2$;

R$_{14}$ is selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, phenyl, or substituted phenyl;

Each R$_{15}$ is independently selected from alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, R$_7$, R$_9$, phenyl, or substituted phenyl;

Each R$_{16}$ is independently selected from cycloalkyl, halogenated cycloalkyl, substituted cycloalkyl, heterocycloalkyl, halogenated heterocycloalkyl, substituted heterocycloalkyl, R$_7$, R$_9$, phenyl, or substituted phenyl;

R$_{17}$ is selected from cycloalkyl, halogenated cycloalkyl, substituted cycloalkyl, heterocycloalkyl, halogenated heterocycloalkyl, or substituted heterocycloalkyl;

Each R$_{18}$ is independently selected from —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$RS(O)$_2$R$_{11}$, —F, —Cl, —Br, or —I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from —F, —Cl, —Br, or —I;

and pharmaceutically acceptable salts thereof. Compounds of Formula I are useful to treat any one of or combination of attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulemia and anorexia nervosa, withdrawal symptoms associated with smoking cessation and dependant drug cessation, Gilles de la Tourette's Syndrome, glaucoma, neurodegeneration associated with glaucoma, or symptoms associated with pain.

DETAILED DESCRIPTION OF THE INVENTION

Surprisingly, we have found that compounds of Formula I:

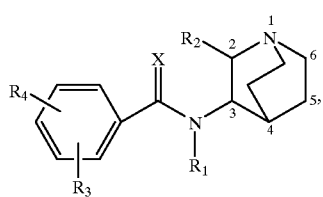

Formula I wherein X is O or S;

$R_1$ is independently selected from the group consisting of —H, alkyl, cycloalkyl, halogenated alkyl, and aryl;

Alkyl is both straight- and branched-chain moieties having from 1–6 carbon atoms;

Halogenated alkyl is an alkyl moiety having from 1–6 carbon atoms and having 1 to (2n+1) substituent(s) independently selected from —F, —Cl, —Br, or —I where n is the maximum number of carbon atoms in the moiety;

Cycloalkyl is a cyclic alkyl moiety having from 3–6 carbon atoms;

Aryl is phenyl, substituted phenyl, naphthyl, or substituted naphthyl;

Substituted phenyl is a phenyl either having 1–4 substituents independently selected from —F, —Cl, —Br, or —I, or having 1 substituent selected from —$R_{12}$ and 0–3 substituents independently selected from —F, —Cl, —Br, or —I;

Substituted naphthyl is a naphthalene moiety either having 1–4 substituents independently selected from —F, —Cl, —Br, or I, or having 1 substituent selected from —$R_{12}$ and 0–3 substituents independently selected from —F, —Cl, —Br, or —I, where the substitution can be independently on either only one ring or both rings of said naphthalene moiety;

$R_2$ is —H, alkyl, halogenated alkyl, substituted alkyl, cycloalkyl, benzyl, substituted benzyl, or aryl;

Substituted alkyl is an alkyl moiety from 1–6 carbon atoms and having 0–3 substituents independently selected from —F, —Cl, —Br, or —I and further having 1 substituent selected from —$OR_{10}$, —$SR_{10}$, —$NR_{10}R_{10}$, —C(O)RlO, —C(O)$NR_{10}R_{10}$, —CN, —$NR_{10}C(O)R_{10}$, —S(O)$_2$$NR_{10}R_{10}$, —$NR_{10}S(O)_2R_{10}$, —$NO_2$, —$R_7$, —$R_9$, phenyl, or substituted phenyl;

Substituted benzyl is a benzyl either having 1–4 substituents independently selected from —F, —Cl, —Br, or —I, or having 1 substituent selected from —$R_{12}$ and 0–3 substituents independently selected from —F, —Cl, —Br, or —I, provided that all substitution is on the phenyl ring of the benzyl;

$R_3$ is selected from the group consisting of —H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, aryl, —$R_7$, —$R_9$, —$OR_8$, —$OR_{17}$, —$SR_8$, —F, —Cl, —Br, —I, —$NR_8R_8$, —$NR_{16}R_{16}$, —C(O)$R_8$, —C(O)$R_{16}$, —CN, —C(O)$NR_8R_8$, —C(O)$NR_{15}R_{15}$, —$NR_8C(O)R_8$, —S(O)$R_8$, —OS(O)$_2R_8$, —$NR_8S(O)_2R_8$, —$NO_2$, and —N(H)C(O)N(H)$R_8$;

Alkenyl is straight- and branched-chain moieties having from 2–6 carbon atoms and having at least one carbon-carbon double bond;

Halogenated alkenyl is an unsaturated alkenyl moiety having from 2–6 carbon atoms and having 1 to (2n−1) substituent(s) independently selected from —F, —Cl, —Br, or —I where n is the maximum number of carbon atoms in the moiety;

Substituted alkenyl is an unsaturated alkenyl moiety having from 2–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —C(O)$R_{10}$, —C(O)$NR_{10}R_{10}$, —$NR_{10}C(O)R_{10}$, —S(O)$_2NR_{10}R_{10}$, —$NR_{10}S(O)_2R_{10}$, —CN, phenyl, or substituted phenyl;

Alkynyl is straight- and branched-chained moieties having from 2–6 carbon atoms and having at least one carbon-carbon triple bond;

Halogenated alkynyl is an unsaturated alkynyl moiety having from 3–6 carbon atoms and having 1 to (2n−3) substituent(s) independently selected from —F, —Cl, —Br, or —I where n is the maximum number of carbon atoms in the moiety;

Substituted alkynyl is an unsaturated alkynyl moiety having from 3–6 carbon atoms and having 0–3 substituents independently selected from —F, or —Cl, and further having 1 substituent selected from —$R_7$, —$R_9$, —$OR_{10}$—$SR_{10}$, —$NR_{10}R_{10}$, —C(O)$R_{10}$, —C(O)$NR_{10}R_{10}$—$NR_{10}C(O)R_{10}$, —S(O)$_2NR_{10}R_{10}$, —$NR_{10}S(O)_2R_{10}$, —CN, phenyl, or substituted phenyl;

Halogenated cycloalkyl is a cyclic moiety having from 3–6 carbon atoms and having 1–4 substituents independently selected from —F, or —Cl;

Substituted cycloalkyl is a cyclic moiety having from 3–6 carbon atoms and having 0–3 substituents independently selected from —F, or —Cl, and further having 1 substituent selected from —$OR_{10}$, —$SR_{10}$, —$NR_{10}R_{10}$, —C(O)$R_{10}$, —CN, —C(O)$NR_{10}R_{10}$, —$NR_{10}C(O)R_{10}$, —S(O)$_2NR_{10}R_{10}$, —$NR_{10}S(O)_2R_{10}$, —$NO_2$, phenyl, or substituted phenyl;

Heterocycloalkyl is a cyclic moiety having 4–7 atoms with 1–2 atoms within the ring being —S—, —N($R_3$)—, or —O—;

Halogenated heterocycloalkyl is a cyclic moiety having from 4–7 atoms with 1–2 atoms within the ring being —S—, —N($R_3$)—, or —O—, and having 1–4 substituents independently selected from —F, or —Cl;

Substituted heterocycloalkyl is a cyclic moiety having from 4–7 atoms with 1–2 atoms within the ring being —S—, —N($R_3$)—, or —O— and having 0–3 substituents independently selected from —F, or —Cl, and further having 1 substituent selected from —$OR_{10}$, —$SR_{10}$, —$NR_{10}R_{10}$, —C(O)$R_{10}$, —C(O)$NR_{10}R_{10}$, —CN, —$NR_{10}C(O)R_{10}$, —$NO_2$, —S(O)$_2NR_{10}R_{10}$, —$NR_{10}S(O)_2R_{10}$, phenyl, or substituted phenyl;

$R_4$ is selected from the group consisting of —O—$R_5$, —S—$R_5$, —S(O)—$R_5$, —C(O)—$R_5$, and alkyl substituted on the ω carbon with $R_5$ where said ω carbon is determined by counting the longest carbon chain of the alkyl moiety with the C-1 carbon being the carbon attached to the phenyl ring of the core molecule and the ω carbon being the carbon furthest from said C-1 carbon;

$R_5$ is selected from aryl, $R_7$, or $R_9$;

$R_7$ is 5-membered heteroaromatic mono-cyclic moieties containing within the ring 1–3 heteroatoms independently selected from the group consisting of —O—, =N—, —N($R_{14}$)—, and —S—, and having 0–1 substituent selected from —$R_{12}$ and 0–3 substituents independently selected from —F, —Cl, —Br, or —I, or $R_7$ is a 9-membered fused-ring moiety having a 6-membered ring fused to a 5-membered ring and having the formula

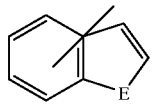

wherein E is O, S, or $NR_{14}$,

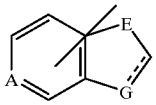

wherein E and G are independently selected from $CR_{18}$, O, S, or $NR_{14}$, and A is $CR_{18}$ or N, or

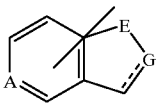

wherein E and G are independently selected from $CR_{18}$, O, S, or $NR_{14}$, and A is $CR_{18}$ or N, each 9-membered fused-ring moiety having 0–1 substituent selected from —$R_{12}$ and 0–3 substituent(s) independently selected from —F, —Cl, —Br, or —I, and having a bond directly or indirectly attached to the core molecule where valency allows in either the 6-membered or the 5-membered ring of the fused-ring moiety;

Each $R_8$ is independently selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from —$R_{12}$ and 0–3 substituent(s) independently selected from —F, —Cl, —Br, or —I, or 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from —$R_{12}$ and 0–3 substituent(s) independently selected from —F, —Cl, —Br, or —I and having a bond directly or indirectly attached to the core molecule where valency allows;

Each $R_{10}$ is independently selected from —H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or substituted phenyl;

Each $R_{11}$ is independently selected from —H, alkyl, cycloalkyl, heterocycloalkyl, halogenated alkyl, halogenated cycloalkyl, or halogenated heterocycloalkyl;

$R_{12}$ is selected from —$OR_{11}$, —$SR_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$NR_{11}R_{11}$, —$C(O)R_{11}$, —$NO_2$, —$C(O)NR_{11}R_{11}$, —CN, —$NR_{11}C(O)R_{11}$, —$S(O)2NR_{11}R_{11}$, or —$NR_{11}S(O)_2R_{11}$;

$R_{13}$ is selected from —$OR_{11}$, —$SR_{11}$, —$NR_{11}R_{11}$, —$C(O)R_{11}$, —$C(O)NR_{1111}$, —CN, —$CF_3$, —$NR_{11}C(O)R_{11}$, —$S(O)_2NR_{11}R_{11}$, —NRI $S(O)_2R_{11}$, or —$NO_2$;

$R_{14}$ is selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, phenyl, or substituted phenyl;

Each $R_{15}$ is independently selected from alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

Each $R_{16}$ is independently selected from cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_{17}$ is selected from cycloalkyl, halogenated cycloalkyl, substituted cycloalkyl, heterocycloalkyl, halogenated heterocycloalkyl, or substituted heterocycloalkyl;

Each $R_{18}$ is independently selected from —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}RI$, —$C(O)R_{11}$, —$NO_2$, —$C(O)NR_{11}R_{11}$, —CN, —$NR_{11}C(O)R_1$, —$S(O)_2NR_{11}R_{11}$, or —$NR_{11}S(O)_2R_{11}$, —F, —Cl, —Br, or —I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring moiety has 0–3 substituent(s) selected from —F, —Cl, —Br, or —I;

and pharmaceutically acceptable salts thereof are useful to treat any one of or combination of attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulemia and anorexia nervosa, withdrawal symptoms associated with smoking cessation and dependant drug cessation, Gilles de la Tourette's Syndrome, glaucoma, neurodegeneration associated with glaucoma, or symptoms associated with pain.

Abbreviations which are well known to one of ordinary skill in the art may be used (e.g., "Ph" for phenyl, "Me" for methyl, "Et" for ethyl, "h" for hour or hours, "rt" for room temperature, and min for minute or minutes).

All temperatures are in degrees Centigrade.

Room temperature is within the range of 15–25 degrees Celsius.

Eq refers to equivalents.

AChR refers to acetylcholine receptor.

nAChR refers to nicotinic acetylcholine receptor.

$5HT_3R$ refers to the serotonin-type 3 receptor.

α-btx refers to αbungarotoxin.

FLIPR refers to a device marketed by Molecular Devices, Inc. designed to precisely measure cellular fluorescence in a high throughput whole-cell assay. (Schroeder et. al., *J. Biomolecular Screening*, 1(2), p 75–80, 1996).

TLC refers to thin-layer chromatography.

HPLC refers to high pressure liquid chromatography.

MeOH refers to methanol.

EtOH refers to ethanol.

IPA refers to isopropyl alcohol.

THF refers to tetrahydrofuran.

DMSO refers to dimethylsulfoxide.

DMF refers to dimethylformamide.

EtOAc refers to ethyl acetate.

TMS refers to tetramethylsilane.

TEA refers to triethylamine.

DIEA refers to diisopropylethylamine.

-MLA refers to methyllycaconitine.

Ether refers to diethyl ether.

$MgSO_4$ refers magnesium sulfate.

$NaHCO_3$ refers to sodium bicarbonate.

$KHCO_3$ refers to potassium bicarbonate.

$CH_3CN$ refers to acetonitrile.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-6}$ alkyl refers to alkyl of one to six carbon atoms.

Halogen is F, Cl, Br, or I.

Alkyl denotes both straight- and branched-chained hydrocarbyl radicals having from 1–6 carbon atoms. For example, $C_{1-6}$ alkyl includes methyl, ethyl, propyl, isopropyl, butyl, iso-butyl, sec-butyl, pentyl, 3-pentyl, hexyl, and their isomeric forms thereof.

Halogenated alkyl is an alkyl moiety having from 1–6 carbon atoms and having 1 to (2n+1) halogen atom(s) where n is the maximum number of carbon atoms in the moiety.

Substituted alkyl is an alkyl moiety having from 1–6 carbon atoms and having 0–3 substituents independently selected from —F, —Cl, —Br, or —I, and further having 1 substituent selected from —$R_7$, —$R_9$, —$OR_{10}$, —$SR_{10}$, —$NR_{10}R_{10}$, —$C(O)R_{10}$, —$NO_2$, —$C(O)NR_{10}R_{10}$, —CN, —$NR_{10}C(O)R_{10}$, —$S(O)_2NR_{10}R_{10}$, —$NR_{10}S(O)_2R_{10}$, phenyl, or substituted phenyl.

Alkenyl is straight- and branched-chained hydrocarbyl radicals having from 2–6 carbon atoms and having at least one carbon-carbon double bond.

Halogenated alkenyl is an unsaturated alkenyl moiety having from 2–6 carbon atoms and having 1 to (2n–1) halogen atom(s) where n is the maximum number of carbon atoms in the moiety.

Substituted alkenyl is an unsaturated alkenyl moiety having from 2–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —CN, —$C(O)NR_{10}R_{10}$—$NR_{10}C(O)R_{10}$, —$S(O)_2NR_{10}R_{10}$—$NR_{10}S(O)_2R_{10}$, phenyl, or substituted phenyl.

Alkynyl is straight- and branched-chained hydrocarbyl radicals having from 2–6 carbon atoms and having at least one carbon-carbon triple bond.

Halogenated alkynyl is an unsaturated alkynyl moiety having from 3–6 carbon atoms and having 1 to (2n–3) halogen atom(s) where n is the maximum number of carbon atoms in the moiety.

Substituted alkynyl is an unsaturated alkynyl moiety having from 3–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —CN, —$C(O)NR_{10}R_{10}$, —$NR_{10}C(O)R_{10}$, —$S(O)_2NR_{10}R_{10}$, —$NR_{10}S(O)_2R_{10}$, phenyl, or substituted phenyl.

Cycloalkyl is a cyclic alkyl moiety having from 3–6 carbon atoms.

Halogenated cycloalkyl is a cyclic moiety having from 3–6 carbon atoms and having 1–4 substituents independently selected from —F, or —Cl.

Substituted cycloalkyl is a cyclic moiety having from 3–6 carbon atoms and having 0–3 substituents independently selected from —F, or —Cl, and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$S(O)_2NR_{10}R_{10}$, —$NR_{10}S(O)_2R_{10}$, —$NO_2$, phenyl, or substituted phenyl.

Heterocycloalkyl is a cyclic moiety having 4–7 atoms with 1–2 atoms within the ring being —S—, —$N(R_3)$— or —O—.

Halogenated heterocycloalkyl is a cyclic moiety having from 4–7 atoms with 1–2 atoms within the ring being —S—, —$N(R_3)$—, or —O—, and having 1–4 substituents independently selected from —F, or —Cl.

Substituted heterocycloalkyl is a cyclic moiety having from 4–7 atoms with 1–2 atoms within the ring being —S—, —$N(R_3)$— or —O— and having 0–3 substituents independently selected from —F, or —Cl, and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$NO_2$, —$S(O)_2NR_{10}R_{10}$, —$NR_{10}S(O)_2R_{10}$, phenyl, or substituted phenyl.

Substituted benzyl is a benzyl either having 1–4 substituents independently selected from —F, —Cl, —Br, or —I, or having 1 substituent selected from —$R_{12}$ and 0–3 substituents independently selected from —F, —Cl, —Br, or —I, provided that all substitution is on the phenyl ring of the benzyl.

Aryl is phenyl, substituted phenyl, naphthyl, or substituted naphthyl.

Substituted phenyl is a phenyl either having 14 substituents independently selected from —F, —Cl, —Br, or —I, or having 1 substituent selected from —$R_{12}$ and 0–3 substituents independently selected from —F, —Cl, —Br, or —I.

Substituted naphthyl is a naphthalene moiety either having 1–4 substituents independently selected from —F, —Cl, —Br, or —I, or having 1 substituent selected from —$R_{12}$ and 0–3 substituents independently selected from —F, —Cl, —Br, or —I, where the substitution can be independently on either only one ring or both rings of said naphthalene moiety.

The ω carbon is determined by counting the longest carbon chain of the alkyl-type moiety with the C-1 carbon being the carbon attached to the phenyl ring of the core molecule and the co carbon being the carbon furthest, e.g., separated by the greatest number of carbon atoms in the chain, from said C-1 carbon.

The core molecule is the quinuclidinyl-(carboxamide-type moiety)-phenyl;

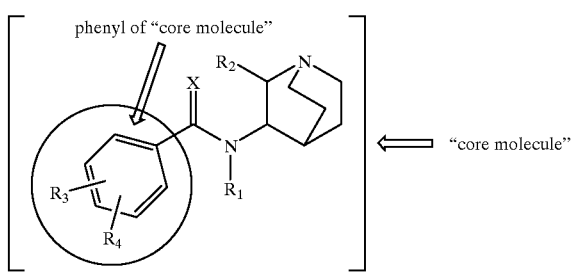

Therefore, when determining the ω carbon, the C-1 carbon will be the carbon attached to the phenyl ring of the core molecule and the ω carbon will be the carbon furthest from said C-1 carbon.

Mammal denotes human and other mammals.

Brine refers to an aqueous saturated sodium chloride solution.

IR refers to infrared spectroscopy.

Lv refers to leaving groups within a molecule, including Cl, OH, or mixed anhydride.

NMR refers to nuclear (proton) magnetic resonance spectroscopy, chemical shifts are reported in ppm (δ) downfield from TMS.

MS refers to mass spectrometry expressed as m/e or mass/charge unit. HRMS refers to high resolution mass spectrometry expressed as m/e or mass/charge unit. M+H$^+$ refers to the positive ion of a parent plus a hydrogen atom. M−H$^-$ refers to the negative ion of a parent minus a hydrogen atom. M+Na$^+$ refers to the positive ion of a parent plus a sodium atom. M+K$^+$ refers to the positive ion of a parent plus a potassium atom. EI refers to electron impact. ESI refers to electrospray ionization. CI refers to chemical ionization. FAB refers to fast atom bombardment.

Compounds of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N, N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a nontoxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

The compounds of Formula I have optically active center(s) on the quinuclidine ring. Although it is desirable that the stereochemical purity be as high as possible, absolute purity is not required. This invention involves racemic mixtures and compositions of varying degrees of streochemical purities. It is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions.

The preferred compounds of the present invention have the R configuration at the C3 position of the quinuclidine ring. It is also preferred for the compounds of the present invention that X is O. It is also preferred that $R_4$ is attached at the C4 position of the phenyl ring of the core molecule. Another group of compounds of Formula I includes compounds wherein X is O and $R_1$ is H. Another group of compounds of Formula I includes compounds wherein X is O and $R_2$ is H. Another group of compounds of Formula I includes compounds wherein X is O and $R_2$ is alkyl, halogenated alkyl, substituted alkyl, cycloalkyl, benzyl, substituted benzyl, or aryl.

The amount of therapeutically effective compound(s) that is administered and the dosage regimen for treating a disease condition with the compounds and/or compositions of this invention depends on a variety of factors, including the age, weight, sex and medical condition of the subject, the severity of the disease, the route and frequency of administration, and the particular compound(s) employed, and thus may vary widely. The compositions contain well know carriers and excipients in addition to a therapeutically effective amount of compounds of Formula I. The pharmaceutical compositions may contain active ingredient in the range of about 0.001–100 mg/kg/day for an adult, preferably in the range of about 0.1–50 mg/kg/day for an adult. A total daily dose of about 1–1000 mg of active ingredient may be appropriate for an adult. The daily dose can be administered in 1–4 doses per day.

In addition to the compound(s) of Formula I, the composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The serotonin type 3 receptor ($5HT_3R$) is a member of a superfamily of ligand-gated ion channels, which includes the muscle and neuronal nAChR, the glycine receptor, and the γ-aminobutyric acid type A receptor. Like the other members of this receptor superfamily, the $5HT_3R$ exhibits a large degree of sequence homology with α 7 nAChR but functionally the two ligand-gated ion channels are very different. For example, α7 nAChR is rapidly inactivated, is highly permeable to calcium and is activated by acetylcholine and nicotine. On the other hand, $5HT_3R$ is inactivated slowly, is relatively impermeable to calcium and is activated by serotonin. These experiments suggest that the α7 nAChR and $5HT_3R$ proteins have some degree of homology, but function very differently. Indeed the pharmacology of the channels is very different. For example, Ondansetron, a highly selective $5HT_3R$ antagonist, has little activity at the α7 nAChR. The converse is also true. For example, GTS-21, a highly selective α7 nAChR agonist, has little activity at the $5HT_3R$.

α7 nAChR is a ligand-gated $Ca^{++}$ channel formed by a homopentamer of α7 subunits. Previous studies have established that α-bungarotoxin (α-btx) binds selectively to this homopetameric, α7 nAChR subtype, and that α:7 nAChR has a high affinity binding site for both oc-btx and methyllycaconitine (-MLA). α7 nAChR is expressed at high levels in the hippocampus, ventral tegmental area and ascending cholinergic projections from nucleus basilis to thalamocortical areas. α7 nAChR agonists increase neurotransmitter release, and increase cognition, arousal, attention, learning and memory.

Data from human and animal pharmacological studies establish that nicotinic cholinergic neuronal pathways control many important aspects of cognitive function including attention, learning and memory (Levin, E. D., *Psychopharnmacology,* 108:417–31, 1992; Levin, E. D. and Simon B. B., *Psychopharmacology,* 138:217–30, 1998). For example, it is well known that nicotine increases cognition and attention in humans. ABT-418, a compound that activates α4β2 and α7 nAChR, improves cognition and attention in clinical trials of Alzheimer's disease and attention-deficit disorders (Potter, A. et. al., *Psychophannacology* (Berl)., 142(4):334–42, Mar. 1999; Wilens, T. E. et. al., *Am. J. Psychiatry,* 156(12):1931–7, Dec. 1999). It is also clear that nicotine and selective but weak α7 nAChR agonists increase cognition and attention in rodents and non-human primates.

Selective α7 nAChR agonists may be found using a functional assay on FLIPR (see WO 00/73431 A2). FLIPR is designed to read the fluorescent signal from each well of a 96 or 384 well plate as fast as twice a second for up to 30 minutes. This assay may be used to accurately measure the functional pharmacology of α7 nAChR and $5HT_3R$. To conduct such an assay, one uses cell lines that expressed functional forms of the α7 nAChR using the α7/5—$HT_3$ channel as the drug target and cell lines that expressed functional $5HT_3R$. In both cases, the ligand-gated ion channel was expressed in SH-EP1 cells. Both ion channels can produce robust signal in the FLIPR assay.

The compounds of the present invention are α7 nAChR agonists and may be used to treat a wide variety of diseases. For example, they may be used in treating the cognitive and attention deficits as well as the neurodegeneration associated with attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulemia and anorexia nervosa, withdrawal symptoms associated with smoking cessation and dependant drug cessation, Gilles de la Tourette's Syndrome, glaucoma, and symptoms associated with pain.

Attention deficit disorder is generally treated with methylphenidate, an amphetamine-like molecule that has some potential for abuse. Accordingly, it would be desirable to provide a drug that treats attention deficit disorder while having fewer side effects than the currently used drug.

Attention deficit hyperactivity disorder, otherwise known as ADHD, is a neurobehavioral disorder affecting 3–5% of all American children. ADHD concerns cognitive alone or both cognitive and behavioral actions by interfering with a person's ability to stay on a task and to exercise age-appropriate inhibition. Several types of ADHD exist: a predominantly inattentive subtype, a predominantly hyperactive-impulsive subtype, and a combined subtype. Treatment may include medications such as methylphenidate, dextroamphetamine, or pemoline, which act to decrease impulsivity and hyperactivity and to increase attention. No "cure" for ADHD currently exists. Children with the disorder seldom outgrow it; therefore, there is a need for appropriate medicaments.

Mood and affective disorders fall within a large group of diseases, including monopolar depression and bi-polar mood disorder. These diseases are treated with three major classes of compounds. The first group is the heterocyclic antidepressant (HCA's). This group includes the well-known tricyclic antidepressants. The second group of compounds used to treat mood disorders is the monoamine oxidase inhibitors (MAOI's) that are used in particular types of diseases. The third drug is lithium. Common side effects from HCA's are sedation and weight gain. In elderly patients with organic brain disease, the side effects of HCA's can also include seizures and behavioral symptoms. The main side effects from using MAOI's occur from dietary and drug interactions. Benign side effects from the use of lithium include, but are not limited to, weight gain, nausea, diarrhea, polyuria, polydipsia, and tremor. Toxic side effects from lithium can include persistent headache, mental confusion, and may reach seizures and cardiac arrhythmias. Therefore, agents with less side effects or interactions with food or other medications would be useful.

Depression is a mood disorder of varying lengths of normally several months to more than two years and of varying degrees of feelings involving sadness, despair, and discouragement. The heterocyclic antidepressants (HCA's) are currently the largest class of antidepressants, but monoamine oxidase inhibitors (MAOI's) are used in particular types of depression. Common side effects from HCA's are sedation and weight gain. In elderly patients with organic brain disease, the side effects from HCA's can also include seizures and behavioral symptoms. The main side effects from using MAOI's occur from dietary and drug interactions. Therefore, agents with fewer side effects would be useful.

Borderline personality disorder, although not as well known as bipolar disorder, is more common. People having borderline personality disorder suffer from a disorder of emotion regulation. Pharmaceutical agents are used to treat specific symptoms, such as depression or thinking distortions.

Acquired immune deficiency syndrome (AIDS) results from an infection with the human immunodeficiency virus (HIV). This virus attacks selected cells and impairs the proper function of the immune, nervous, and other systems. HIV infection can cause other problems such as, but not limited to, difficulties in thinking, otherwise known as AIDS dementia complex. Therefore, there is a need to drugs to relieve the confusion and mental decline of persons with AIDS.

Amyotrophic lateral sclerosis, also known as Lou Gehrig's disease, belongs to a class of disorders known as motor neuron diseases wherein specific nerve cells in the brain and spinal cord gradually degenerate to negatively affect the control of voluntary movement. Currently, there is no cure for amyotrophic lateral sclerosis although patients may receive treatment from some of their symptoms and although Riluzole has been shown to prolong the survival of patients. Therefore, there is a need for a pharmaceutical agent to treat this disease.

Traumatic brain injury occurs when the brain is damaged from a sudden physical assault on the head. Symptoms of the traumatic brain injury include confusion and other cognitive problems. Therefore, there is a need to address the symptoms of confusion and other cognitive problems.

Brain tumors are abnormal growths of tissue found inside of the skull. Symptoms of brain tumors include behavioral and cognitive problems. Surgery, radiation, and chemotherapy are used to treat the tumor, but other agents are necessary to address associated symptoms. Therefore, there is a need to address the symptoms of behavioral and cognitive problems.

Persons with Down's syndrome have in all or at least some of their cells an extra, critical portion of the number 21 chromosome. Adults who have Down's syndrome are known to be at risk for Alzheimer-type dementia. Currently, there is no proven treatment for Down's syndrome. Therefore, there is a need to address the dementia associated with Down's syndrome.

Genetically programmed degeneration of neurons in certain areas of the brain cause Huntington's disease. Early symptoms of Huntington's disease include mood swings, or trouble learning new things or remembering a fact. Most drugs used to treat the symptoms of Huntington's disease have side effects such as fatigue, restlessness, or hyperexcitability. Currently, there is no treatment to stop or reverse the progression of Huntington's disease. Therefore, there is a need of a pharmaceutical agent to address the symptoms with fewer side effects.

General anxiety disorder (GAD) occurs when a person worries about things such as family, health, or work when there is no reason to worry and is unable not to worry. About 3 to 4% of the U.S. population has GAD during the course of a year. GAD most often strikes people in childhood or adolescence, but can begin in adulthood, too. It affects women more often than men. Currently, treatment involves cognitive-behavioral therapy, relaxation techniques, and biofeedback to control muscle tension and medications such as benzodiazepines, imipramine, and buspirone. These drugs are effective but all have side-effect liabilities. Therefore, there is a need of a pharmaceutical agent to address the symptoms with fewer side effects.

Dementia with Lewy Bodies is a neurodegenerative disorder involving abnormal structures known as Lewy bodies found in certain areas of the brain. Symptoms of dementia with Lewy bodies include, but are not limited to, fluctuating cognitive impairment with episodic delirium. Currently, treatment concerns addressing the parkinsonian and psychiatric symptoms. However, medicine to control tremors or loss of muscle movement may actually accentuate the underlying disease of dementia with Lewy bodies. Therefore, there is a need of a pharmaceutical agent to treat dementia with Lewy bodies.

Age-related macular degeneration (AMD) is a common eye disease of the macula which is a tiny area in the retina that helps produce sharp, central vision required for "straight ahead" activities that include reading and driving. Persons with AMD lose their clear, central vision. AMD takes two forms: wet and dry. In dry AMD, there is a slow breakdown of light-sensing cells in the macula. There currently is no cure for dry AMD. In wet AMD, new, fragile blood vessels growing beneath the macula as dry AMD worsens and these vessels often leak blood and fluid to cause rapid damage to the macula quickly leading to the loss of central vision. Laser surgery can treat some cases of wet AMD. Therefore, there is a need of a pharmaceutical agent to address AMD.

Parkinson's disease is a neurological disorder characterized by tremor, hypokinesia, and muscular rigidity. Currently, there is no treatment to stop the progression of the disease. Therefore, there is a need of a pharmaceutical agent to address Parkinson's.

Tardive dyskinesia is associated with the use of conventional antipsychotic drugs. This disease is characterized by involuntary movements most often manifested by puckering of the lips and tongue and/or writhing of the arms or legs. The incidence of tardive dyskinesia is about 5% per year of drug exposure among patients taking conventional antipsychotic drugs. In about 2% of persons with the disease, tardive dyskinesia is severely disfiguring. Currently, there is no generalized treatment for tardive dyskinesia. Furthermore, the removal of the effect-causing drugs is not always an option due to underlying problems. Therefore, there is a need for a pharmaceutical agent to address the symptoms of tardive dyskinesia.

Pick's disease results from a slowly progressive deterioration of social skills and changes in personality with the resulting symptoms being impairment of intellect, memory, and language. Common symptoms include memory loss, lack of spontaneity, difficulty in thinking or concentrating, and speech disturbances. Currently, there is no specific treatment or cure for Pick's disease but some symptoms can be treated with cholinergic and serotonin-boosting antidepressants. In addition, antipsychotic medications may alleviate symptoms in FTD patients who are experiencing delusions or hallucinations. Therefore, there is a need for a pharmaceutical agent to treat the progressive deterioration of social skills and changes in personality and to address the symptoms with fewer side effects.

Post-traumatic stress disorder (PTSD) is a form of anxiety triggered by memories of a traumatic event that directly affected the patient or that the patient may have witnessed. The disorder commonly affects survivors of traumatic events including sexual assault, physical assault, war, torture, natural disasters, an automobile accident, an airplane crash, a hostage situation, or a death camp. The affliction also can affect rescue workers at an airplane crash or a mass shooting, someone who witnessed a tragic accident or someone who has unexpectedly lost a loved one. Treatment for PTSD includes cognitive-behavioral therapy, group psychotherapy, and medications such as Clonazepam, Lorazepam and selective serotonin-reuptake inhibitors such as Fluoxetine, Sertraline, Paroxetine, Citalopram and Fluvoxamine. These medications help control anxiety as well as depression. Various forms of exposure therapy (such as systemic desensitization and imaginal flooding) have all been used with PTSD patients. Exposure treatment for PTSD involves repeated reliving of the trauma, under controlled conditions, with the aim of facilitating the processing of the trauma. Therefore, there is a need for better pharmaceutical agents to treat Post traumatic stress disorder.

Dysregulation of food intake associated with eating disease, including bulemia nervosa and anorexia nervosa, involve neurophysiological pathways. Anorexia nervosa is hard to treat due to patients not entering or remaining in after entering programs. Currently, there is no effective treatment for persons suffering from severe anorexia nervosa. Cognitive behavioral therapy has helped patients suffering from bulemia nervosa; however, the response rate is only about 50% and current treatment does not adequately address emotional regulation. Therefore, there is a need for pharmaceutical agents to address neurophysiological problems underlying diseases of dysregulation of food intake.

Cigarette smoking has been recognized as a major public health problem for a long time. However, in spite of the public awareness of health hazard, the smoking habit remains extraordinarily persistent and difficult to break. There are many treatment methods available, and yet people continue to smoke. Administration of nicotine transdermally, or in a chewing gum base is common treatments. However, nicotine has a large number of actions in the body, and thus can have many side effects. It is clear that there is both a need and a demand of long standing for a convenient and relatively easy method for aiding smokers in reducing or eliminating cigarette consumption. A drug that could selectively stimulate only certain of the nicotinic receptors would be useful in smoke cessation programs.

Smoke cessation programs may involve oral dosing of the drug of choice. The drug may be in the form of tablets. However, it is preferred to administer the daily dose over the waking hours, by administration of a series of incremental doses during the day. The preferred method of such administration is a slowly dissolving lozenge, troche, or chewing gum, in which the drug is dispersed. Another drug in treating nicotine addiction is Zyban. This is not a nicotine replacement, as are the gum and patch. Rather, this works on other areas of the brain, and its effectiveness is to help control nicotine craving or thoughts about cigarette use in people trying to quit. Zyban is not very effective and effective drugs are needed to assist smokers in their desire to stop smoking. These drugs may be administered transdermally through the use of skin patches. In certain cases, the drugs may be administered by subcutaneous injection, especially if sustained release formulations are used.

Drug use and dependence is a complex phenomenon, which cannot be encapsulated within a single definition. Different drugs have different effects, and therefore different types of dependence. Drug dependence has two basic causes, that is, tolerance and physical dependence. Tolerance exists when the user must take progressively larger doses to produce the effect originally achieved with smaller doses. Physical dependence exists when the user has developed a state of physiologic adaptation to a drug, and there is a withdrawal (abstinence) syndrome when the drug is no longer taken. A withdrawal syndrome can occur either when the drug is discontinued or when an antagonist displaces the drug from its binding site on cell receptors, thereby counteracting its effect. Drug dependence does not always require physical dependence.

In addition drug dependence often involves psychological dependence, that is, a feeling of pleasure or satisfaction when taking the drug. These feelings lead the user to repeat the drug experience or to avoid the displeasure of being deprived of the drug. Drugs that produce strong physical dependence, such as nicotine, heroin and alcohol are often abused, and the pattern of dependence is difficult to break. Drugs that produce dependence act on the CNS and generally reduce anxiety and tension; produce elation, euphoria, or other pleasurable mood changes; provide the user feelings of increased mental and physical ability; or alter sensory perception in some pleasurable manner. Among the drugs that are commonly abused are ethyl alcohol, opioids, anxiolytics, hypnotics, cannabis (marijuana), cocaine, amphetamines, and hallucinogens. The current treatment for drug-addicted people often involves a combination of behavioral therapies and medications. Medications, such as methadone or LAAM (levo-alpha-acetyl-methadol), are effective in suppressing the withdrawal symptoms and drug craving associated with narcotic addiction, thus reducing illicit drug use and improving the chances of the individual remaining in treatment. The primary medically assisted withdrawal method for narcotic addiction is to switch the patient to a comparable drug that produces milder withdrawal symptoms, and then gradually taper off the substitute medication. The medication used most often is methadone, taken by mouth once a day. Patients are started on the lowest dose that prevents the more severe signs of withdrawal and then the dose is gradually reduced. Substitutes can be used also for withdrawal from sedatives. Patients can be switched to long-acting sedatives, such as diazepam or phenobarbital, which are then gradually reduced.

Gilles de la Tourette's Syndrome is an inherited neurological disorder. The disorder is characterized by uncontrollable vocal sounds called tics and involuntary movements. The symptoms generally manifest in an individual before the person is 18 years of age. The movement disorder may begin with simple tics that progress to multiple complex tics, including respiratory and vocal ones. Vocal tics may begin as grunting or barking noises and evolve into compulsive utterances. Coprolalia (involuntary scatologic utterances) occurs in 50% of patients. Severe tics and coprolalia may be physically and socially disabling. Tics tend to be more complex than myoclonus, but less flowing than choreic movements, from which they must be differentiated. The patient may voluntarily suppress them for seconds or minutes.

Currently simple tics are often treated with benzodiazepines. For simple and complex tics, Clonidine may be used. Long-term use of Clonidine does not cause tardive dyskinesia; its limiting adverse effect is hypotension. In more severe cases, antipsychotics, such as Haloperidol may be required, but side effects of dysphoria, parkinsonism, akathisia, and tardive dyskinesia may limit use of such antipsychotics. There is a need for a safe and effective methods for treating this syndrome.

Glaucoma is within a group of diseases occurs from an increase in intraocular pressure causing pathological changes in the optical disk and negatively affects the field of vision. Medicaments to treat glaucoma either decrease the amount of fluid entering the eye or increase drainage of fluids from the eye in order to decrease intraocular pressure. However, current drugs have drawbacks such as not working over time or causing side effects so the eye-care professional has to either prescribe other drugs or modify the prescription of the drug being used. There is a need for a safe and effective methods for treating problems manifesting into glaucoma.

Ischemic periods in glaucoma cause release of excitotoxic amino acids and stimulate inducible form of nitric oxide synthase (iNOS) leading to neurodegeneration. Alpha 7 nicotinic agonists may stimulate the release of inhibitory amino acids such as GABA which will dampen hyperexcitablity. Alpha 7 nicotinic agonists are also directly neuroprotective on neuronal cell bodies. Thus alpha 7 nicotinic agonists have the potential to be neuroprotective in glaucoma.

Persons afflicted with pain often have what is referred to as the "terrible triad" of suffering from the pain, resulting in sleeplessness and sadness, all of which are hard on the afflicted individual and that individual's family. Pain can manifest itself in various forms, including, but not limited to, headaches of all severity, back pain, neurogenic, and pain from other ailments such as arthritis and cancer from its existence or from therapy to irradicate it. Pain can be either chronic (persistent pain for months or years) or acute (short-lived, immediate pain to inform the person of possible injury and need of treatment. Persons suffering from pain respond differently to individual therapies with varying degrees of success. There is a need for a safe and effective methods for treating pain.

Finally, the compounds of the present invention may be used in combination therapy with typical and atypical anti-psychotic drugs. All compounds within the present invention are useful for and may also be used in combination with each other to prepare pharmaceutical compositions. Such combination therapy lowers the effective dose of the anti-psychotic drug and thereby reduces the side effects of the anti-psychotic drugs. Some typical anti-psychotic drugs that may be used in the practice of the invention include Haldol. Some atypical anti-psychotic drugs include Ziprasidone, Olanzapine, Resperidone, and Quetiapine.

Compounds of the present invention can generally be prepared using the synthetic schemes illustrated in Schemes 1 and 2. Starting materials can be prepared by procedures described in these schemes or by procedures that would be well known to one of ordinary skill in organic chemistry. The variables used in the Schemes are defined herein.

Compounds of Formula I can be prepared as shown in Scheme 1. The key step in the preparation of this class of compounds is the coupling of commercially available 3-aminoquinuclidine ($R_2$ =H) with the requisite activated carboxylic acid (Lv=OH), acid chloride (Lv=Cl), or mixed anhydride (e.g., Lv=diphenylphosphoryl, or acyloxy of the general formula of —O—C(O)—$R_{LV}$ where $R_{LV}$ includes phenyl or t-butyl)-. Suitable activating reagents are well known in the art, for examples see Kiso, Y.; Yajima, H. "Peptides" pp. 39–91, San Diego, Calif., Academic Press, (1995).

Scheme 1

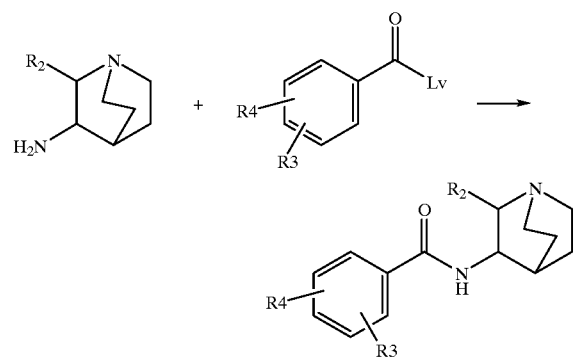

One of ordinary skill in the art will recognize that the methods described for the reaction of the unsubstituted 3-arninoquinuclidine ($R_2$=H) are equally applicable to substituted compounds ($R_2 \ne H$). Such compounds can be prepared by reduction of the oxime of the corresponding 3-quinuclidinone (see *J. Labelled Compds. Radiopharm.*, 53–60 (1995) and *J. Med. Chem.* 988–995, (1998)). The oximes can be prepared by treatment of the 3-quinuclidinones with hydroxylamine hydrochloride in the presence of a base. The 3-quinuclidinones, where $R_2$=substituted alkyl, cycloalkyl, substituted benzyl, can be prepared by known procedures (see *Tet. Lett.* 1015–1018, (1972), *J. Am. Chem. Soc.* 1278–1291 (1994), *J. Am. Chem. Soc.* 4548–4552 (1989), *Tetrahedron*, 1139–1146 (2000)). The 3-quinuclidinones, where $R_2$=aryl, can be prepared by palladium catalyzed arylation as described in *J. Am. Chem. Soc.* 1473–1478 (1999) and *J. Am. Chem. Soc.* 1360–1370 (2000).

It will be apparent to those skilled in the art that the requisite carboxylic acids can be obtained commercially or can be synthesized by known procedures. The acid required in Example 1 is synthesized by acetylation of the corresponding phenol with acetylchloride. The acids in Examples 2, 8–16 are synthesized from the corresponding esters by hydrolysis. Typical hydrolysis procedures are well known in the art. Preferably, the ester is treated with aqueous lithium hydroxide in a solvent such as dioxane. The requisite esters are synthesized from the reaction of a phenol and arylboronic acid as described in *Tet. Lett.*, 2937–2940 (1998). The phenol and boronic acid are reacted in the presence of a copper salt like copper (II) acetate and a base like TEA (Scheme 2). The acids for Examples 3–7 are commercially available. The acids required for Examples 17–22 are synthesized from the corresponding esters by hydrolysis as described above. The esters are synthesized by the reaction of a thiophenol with an aryl halide as described in *Synlett,*

1579–1581 (1999). Namely, the thiophenol and aryl iodide are heated in the presence of a palladium (0) source such as tetrakis(triphenylphosphine)palladium (0) and a base, preferably sodium tert-butoxide.

Scheme 2

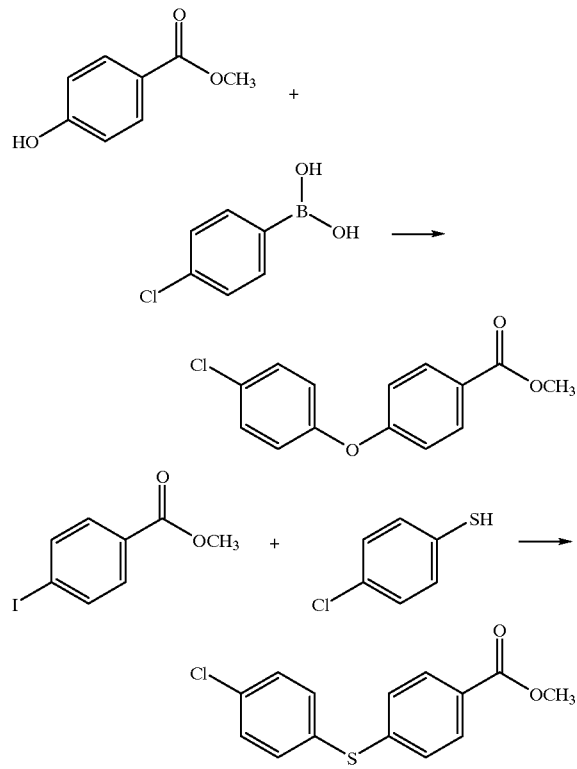

There are a variety of methods for constructing thioamides. One can treat the corresponding amide with a reagent such as Lawesson's reagent (2,4-bis(4-methoxyphenyl)-1,3-dithia-2,4-diphosphetane-2,4-disulfide), as shown in Scheme 3 (see Lawesson et. al. in Bull. Soc. Chim. Belg., 229 (1978)), or $P_4SIO$ (see *Chem. Rev.*, 45 (1961)).

Scheme 3

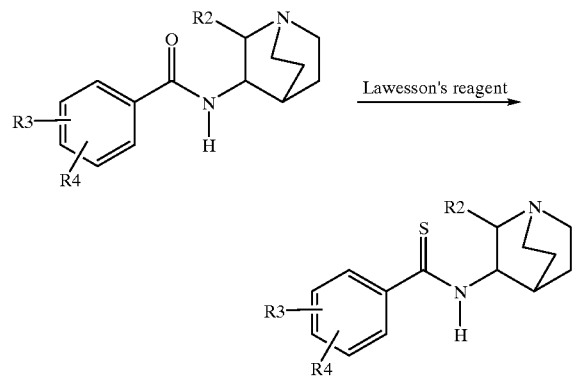

Alternatively one can react a dithiocarboxylic ester with the corresponding quinuclidine to form the same thioamide.

The following examples are provided as examples and are not intended to limit the scope of this invention to only those provided examples and named compounds. Also, the salts made in the examples are only exemplary and are not intended to limit the invention. Any pharmaceutically acceptable salt can be made by one of ordinary skill in the art. Further, the naming of specific stereoisomers is for exemplification, and is not intended to limit in anyway the scope of the invention. The invention includes the following examples in pure stereoisomeric form or as racemic mixtures.

EXAMPLE 1

N-[(3R)-1-azabicyclo[2.2.2]oct-3-yl]-4-(4-hydroxyphenoxy)benzamide:

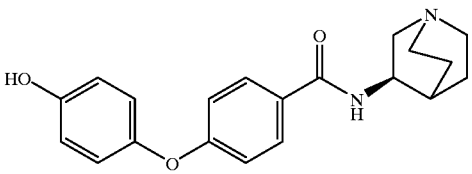

Step A. Preparation of 4-(4-acetoxyphenoxy)benzoic acid.

Acetylchloride (1.5 mnL, 21 mmol) is added to a solution of 4-(4-hydroxy-phenoxy) benzoic acid (2.3 g, 10 mmol) and TEA (2.9 mL, 21 mmol) in $CH_2Cl_2$ (50 mL). The reaction is stirred for 16 hours at room temperature. The reaction mixture is diluted with $CH_2Cl_2$ and washed three times with saturated $NaHCO_3$. The organic layer is dried over $MgSO_4$, filtered and concentrated in vacuo. The resulting material is dissolved in dioxane (6 mL). Aqueous LiOH (IN, 930 μL) is added, and the reaction is allowed to stir for one hour at room temperature. The reaction mixture is poured into $CH_2Cl_2$ and washed twice with $KHSO_4$. The organic layer is dried over $MgSO_4$, filtered and concentrated in vacuo to give the desired acid (1.5 g, 87%). $^1H$ NMR (300 MHz, DMSO) δ 12.80, 7.96, 7.23-7.13, 7.04, 2.29.

Step B. Preparation of N-[(3R)-1-azabicyclo[2.2.2]oct-3-yl]-4-(4-hydroxy-phenoxy) benzamide.

TEA (830 μL, 6.0 mmol) is added to a suspension of the product of Step A (1.5 g, 5.7 mmol) in $CH_2Cl_2$ (5 mL). Diphenylchlorophosphate (1.2 mL, 5.7 mmol) is added and the resulting solution is stirred at room temperature for 30 minutes. This solution is added to a solution of (R)-3-aminoquinuclidine (680 mg, 5.4 mmol) in DMF (6 μL). The resulting solution is stirred overnight at room temperature. MeOH is added and the mixture is poured through a column of AG50 W x2 ion exchange resin ($H^+$ form). The resin is washed with MeOH and then the product is eluted with 5% TEA in MeOH. The eluent is evaporated to dryness. The hydrochloride salt is formed and triturated with hot $CH_3CN$ to yield the desired product (1.2 g, 60%). MS for $C_{20}H_{22}N_2O_3$ (ESI) $(M+H)^+$ m/z 339.

EXAMPLE 2

N-[(3R)-1-azabicyclo[2.2.2]oct-3-yl]-4-(4-acetamidophenoxy)benzamide:

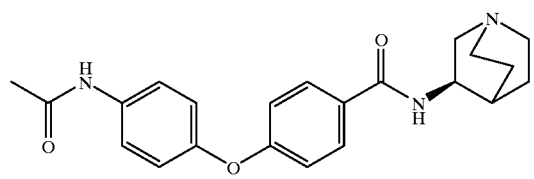

Step C. Preparation of methyl 4-(4-acetamidophenoxy) benzoate.

Dry air is bubbled through a solution of 4-acetamidophenol (320 mg, 2.1 mmol), copper(II) acetate (384 mg, 2.1 mmol), TEA (1.5 mL, 10.5 mol), (4-methoxycarbonylphenyl)-boronic acid (760 mg, 4.2 mmol), and powdered molecular sieves (2 g) in $CH_2Cl_2$ (21 mL) for 16 hours at room temperature. The resulting material is concentrated and purified by flash column chromatography (25–50% EtOAc in heptane) to give the desired product (450 mg, 75%). $^1$H NMR (300MHz, DMSO) δ 8.01, 7.54, 7.27, 7.05, 6.98, 3.92, 2.22.

Step D. Preparation of 4-(4-acetamidophenoxy)benzoic acid.

Aqueous LiOH (1M, 3.12 mL) is added to a suspension of the product of Step C (445 mg, 1.6 mmol) in dioxane (6 mL). The reaction is stirred for 90 minutes at room temperature. Concentrated HCl (1.5 mL) is added to lower the pH to less than 6 and the resulting precipitate is collected by filtration. The filter cake is washed with water then dried to give the desired product (337 mg, 80%). MS for $C_{15}Ht_3NO_4$ (ESI) (M-H)$^-$ m/z 270.

Step E. Preparation of N-[(3R)-1-azabicyclo[2.2.2]oct-3-yl] 4-(4-acetamido-phenoxy) benzamide.

TEA (130 μL, 1.0 mmol) is added to a suspension of the product of Step D (250 mg, 0.9 mmol) in $CH_2CL_2$ (9 mL). Diphenylchlorophosphate (190 μL, 0.9 mmol) is added and the resulting solution is stirred at room temperature for 30 minutes. This solution is added to a solution of (R)-3-aminoquinuclidine (110 mg, 0.88 mmol) in DMF (1mL). The resulting solution is stirred overnight at room temperature. MeOH is added and the mixture is poured through a column of AG50 W ×2 ion exchange resin (H$^+$ form). The resin is washed with MeOH and then the product is eluted with 5% TEA in MeOH. The eluent is evaporated to dryness. The product is crystallized from $CH_3CN$ to yield the desired product (130 mg, 39%). MS for $C_{22}H_{25}N_{3LO3}$ (ESI) (M+H)$^+$ m/z 380.

EXAMPLE 3
N-[(3R)—1-azabicyclo[2.2.2]oct-3-yl]-4-phenoxybenzamide:

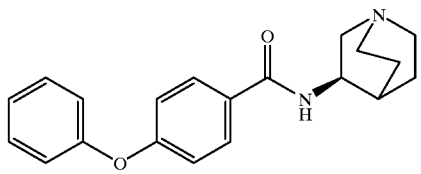

TEA (50 μL, 0.35 mmol) is added to a suspension of 4-phenoxybenzoic acid (75 mg, 0.35 mmol) in $CH_2Cl_2$ (1 mL). Diphenylchlorophosphate (62, μL, 0.3 mmol) is added and the resulting solution is stirred at room temperature for 30 minutes. A solution of (R)-3-aminoquinuclidine (IM in DMF, 0.2 mL, 0.2 mmol) is added and the resulting solution is stirred overnight at room temperature. MeOH is added and the mixture is poured through a column of AG50 W ×2 ion exchange resin (H+form). The resin is washed with MeOH and then the product is eluted with 5% TEA in MeOH. The eluent is evaporated to dryness to yield the desired product (49 mg, 76%). MS for $C_2GH_{22}N_2O_2$ (ESI) (M+H)$^+$ m/z 323.

EXAMPLEs 4–7

The following compounds are made from the corresponding carboxylic acids according to the procedure of Example 3, making non-critical variations.

EXAMPLE 4
N-[(3R)-1-azabicyclo[2.2.2]oct-3-yl]-4-benzylbenzamide (from 4-benzylbenzoic acid). MS for $C_2 lH_{24}N_2O$ (ESI) (M+H)$^+$ m/z 323.

EXAMPLE 5
N-[(3R)-1-azabicyclo[2.2.2]oct-3-yl]-4-(phenylsulfanyl)-benzamide, (from 4-(phenylsulfanyl)-benzoic acid). MS for $C_{20}H_{22}N_2OS$ (ESI) (M+H)$^+$ m/z 339.

EXAMPLE 6
N-[(3R)-1-azabicyclo[2.2.2]oct-3-yl]-3-phenoxybenzamide (from 3-phenoxybenzoic acid). MS for $C_{20}H_{22}N_2O_2$ (ESI) (M+H)$^+$ m/z 323.

EXAMPLE 7
N-[(3R)-1-azabicyclo[2.2.2]oct-3-yl]4-benzoylbenzamide (from 4-benzoylbenzoic acid). MS for $C_{21}H_{22}N_2O_2$ (ESI) (M+H)$^+$ m/z 335.

EXAMPLE 8
N-[(3R)-1-azabicyclo[2.2.2]oct-3-yl]-4-(4-fluorophenoxy) benzamide:

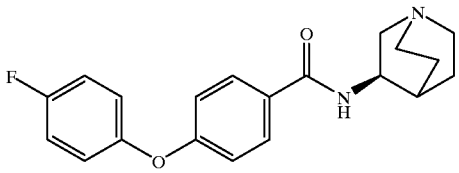

Step F. Preparation of 4-(4-fluorophenoxy)benzoic acid.

To a flask with 4-fluorophenyl boronic acid (2.1 g, 15 mmol), copper(u) acetate (1.4 g, 7.5 mmol), activated powdered molecular sieves (approximately 2 g), and methyl 4-hydroxybenzoate (1.2 g, 7.5 mmol) is added TEA (5.2 mL, 38 mmol) followed by $CH_2Cl_2$ (75 mL). The reaction is stirred for 16 hours at room temperature with air bubbling through it. The reaction mixture is diluted with $CH_2Cl_2$ and filtered through silica gel. The silica gel is washed with EtOAc-heptane. The solution is concentrated in vacuo and dissolved in dioxane (15 mL). To this solution is added aqueous LiOH (1N, 15 mL) and stirred for 18 hours at room temperature. To this reaction mixture is added aqueous HCl (1N) until acidic, having a pH less than 6. The resulting precipitate is collected by filtration and rinsed with water, and dried in vacuo to give the desired product (1.6 g, 90 %). MS for $C_{13}H_9OF_3$ (ESI) (M-H)— m/z 231.

Step G. Preparation of N-[(3R)-1-azabicyclo[2.2.2]oct-3-yl] 4-(4-fluoro-phenoxy) benzamide.

TEA (50 μL, 0.35 mmol) is added to a suspension of the acid from Step F (81 mg, 0.35 mmol) in $CH_2Cl_2$ (lmL). Diphenylchlorophosphate (62 μL, 0.3 mmol) is added and the resulting solution is stirred at room temperature for 30 minutes. A solution of (R)-3-aminoquinuclidine (1 .0 M in $CH_3CN$, 0.2 mL, 0.2 mmol) is added and the resulting solution is shaken overnight at room temperature. MeOH is added and the mixture is poured through a column of AG50 W ×2 ion exchange resin (H$^+$ form). The resin is washed with MeOH and then the product is eluted with 5% TEA in MeOH. The eluent is evaporated to dryness to yield the desired product (58 mg, 85%). MS for $C_{20}H_{21}FN_2O_2$ (ESI) (M+H)$^+$ m/z 341.

EXAMPLES 9–16

The following compounds are made from the corresponding boronic acids according to the procedure of Example 8, making non-critical variations.

EXAMPLE 9
N-[(3R)-1-azabicyclo[2.2.2]oct-3-yl]-4-(2-fluorophenoxy) benzamide (from 2-fluorophenylboronic acid). MS for $C_{20}H_{21}FN_2O_2$ (ESI) (M+H)$^+$ m/z 341.

EXAMPLE 10
N-[(3R)-1-azabicyclo[2.2.2]oct-3-yl]-4-(3-fluorophenoxy) benzamide (from 3-fluorophenylboronic acid). MS for $C_{20}H_{21}FN_{21}O_2$ (ESI) (M+H)+ m/z 341.

EXAMPLE 11
N-[(3R)-1-azabicyclo[2.2.2]oct-3-yl]-4-(2-chlorophenoxy) benzamide (from 2-chlorophenylboronic acid). MS for $C_{20}H_{21}CLNN_2O_2$ (ESI) (M+H)+ m/z 357.

EXAMPLE 12
N-[(3R)-1-azabicyclo[2.2.2]oct-3-yl]-4-(3-chlorophenoxy) benzamide (from 3-chlorophenylboronic acid). MS for $C_{20}H_{21}ClN_2O_2$ (ESI) (M+H)+ m/z 357.

EXAMPLE 13
N-[(3R)-1-azabicyclo[2.2.2]oct-3-yl]-4-(4-chlorophenoxy) benzamide (from 4-chlorophenylboronic acid). MS for $C_{20}H_{21}CLNN_2O_2$ (ESI) (M+H)+ m/z 357.

EXAMPLE 14
N-[(3R)— 1-azabicyclo[2.2.2]oct-3-yl]4-(2-methoxyphenoxy)benzamide (from 2-methoxyphenylboronic acid). MS for $C_{21}H_{24}N_2O_3$ (ESI) (M+H)+ m/z 353.

EXAMPLE 15
N-[(3R)-1-azabicyclo[2.2.2]oct-3-yl]-4-(3-methoxyphenoxy)benzamide (from 3-methoxyphenylboronic acid). MS for $C_{21}H_{24}N_2O_3$ (ESI) (M+H)+ m/z 353.

EXAMPLE 16
N-[(3R)-1-azabicyclo[2.2.2]oct-3-yl]-4-(4-methoxyphenoxy)benzamide (from 4-methoxyphenylboronic acid). MS for $C_{21}H_{24}N_2O_3$ (ESI) (M+H)+ m/z 353.

EXAMPLE 17
N-[(3R)-1-azabicyclo[2.2.2]oct-3-yl]-4-(3-chlorophenylsulfanyl)-benzamide:

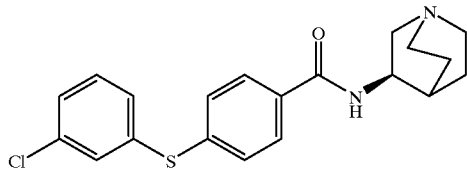

Step H. Preparation of methyl 4-(3-chlorosulfanyl)-benzoate.

A flask containing 3-chlorothiophenol (0.29 mL, 2.5 mmol), potassium tert-butoxide (0.28 g, 2.5 mmol), tetrakis (triphenylphosphine)palladium (0) (0.23 g, 0.2 mmol), and methyl 4-iodobenzoate (0.66 g, 2.5 mmol) is vacuum purged and $N_2$ filled three times. To this flask is added THF (50 mL) and the mixture is stirred at reflux for 24 hours. The solution is diluted with $CH_2Cl_2$ and extracted three times with LN NaOH. The organic layer is dried over $MgSO_4$ and concentrated in vacuo. The crude product is purified by flash-column chromatography (gradient of 0–1 % EtOAc in heptane) to give the desired product (0.53 g, 90%). $^1$H NMR (300MHz, CDCl$_3$) δ 7.96, 7.44-7.43, 7.34-7.29, 3.92.

Step I. Preparation of 4-(3-chlorosulfanyl)-benzoic acid.

The product of Step H (0.53 g, 1.89 mmol) is dissolved in dioxane (4 mnL) followed by addition of aqueous LiOH (lM, 4 mL). The mixture is stirred at room temperature for 5 hours then acidified with aqueous IN HCl to a pH of less than 6. The resulting precipitate is collected by filtration, rinsed with water, and dried in vacuo to give the desired product (0.44 g, 89%). MS for $C_{13}H_9ClO_2S$ (ESI) (M–H)− m/z 263.

Step J. Preparation of N-[(3R)-1-azabicyclo[2.2.2]oct-3-yl]-4-(3-chlorophenyl-sulfanyl) -benzamide.

TEA (50 μL, 0.35 mmol) is added to a suspension of the acid from Step I (93 mg, 0.35 mmol) in $CH_2CL_2$ (1 mL). Diphenylchlorophosphate (62ltL, 0.3 mmol) is added and the resulting solution is stirred at room temperature for 30 minutes. A solution of (R)-3-aminoquinuclidine (10 M in DMF, 0.2 mL, 0.2 mmol) is added and the resulting solution is allowed to sit overnight at room temperature. MeOH is added and the mixture is poured through a column of AG50 W×2 ion exchange resin (H+ form). The resin is washed with MeOH and then the product is eluted with 5% TEA in MeOH. The eluent is evaporated to dryness to yield the desired product (59 mg, 75%). MS for $C_{20}H_{21}ClN_2$ OS (ESI) (M+H)+ m/z 373.

EXAMPLES 18–22

The following compounds are made from the corresponding thiophenols according to the procedure of Example 17, making non-critical variations.

EXAMPLE 18
N-[(3R)-1-azabicyclo[2.2.2]oct-3-yl]-4-(4-chlorophenyl-sulfanyl) -benzamide (from 4-chlorothiophenol). MS for $C_{20}H_{21}ClN_2$ OS (ESI) (M+H)+ m/z 373.

EXAMPLE 19
N-[(3R)-1-azabicyclo[2.2.2]oct-3-yl]-4-(2-chlorophenyl-sulfanyl) -benzamide (from 2-chlorothiophenol). MS for $C_{20}H_{21}ClN_2$ OS (ESI) (M+H)+ m/z 373.

EXAMPLE 20
N-[(3R)-1-azabicyclo[2.2.2]oct-3-yl]-4-(4-methoxyphenyl-sulfanyl) -benzamide (from 4-methoxythiophenol). MS for $C_{21}H_{24}N_2O_2S$ (ESD (M+H)+ m/z 369.

EXAMPLE 21
N-[(3R)-1-azabicyclo[2.2.2]oct-3-yl]4-(3-methoxyphenyl-sulfanyl) -benzamide (from 3-methoxythiophenol). MS for $C_{21}H_{24}N_2O_2S$ (ESI) (M+H)+ m/z 369.

EXAMPLE 22
N-[(3R)-1-azabicyclo[2.2.2]oct-3-yl]-4-(2-methoxyphenyl-sulfanyl) -benzamide (from 2-methoxythiophenol). MS for $C_{21}H_{24}N_2O_2S$ (ESI) (M+H)+ m/z 369.

EXAMPLE 23
N-(2-methyl-1-azabicyclo[2.2.2]oct-3-yl)-4-phenoxybenzamide fumarate:

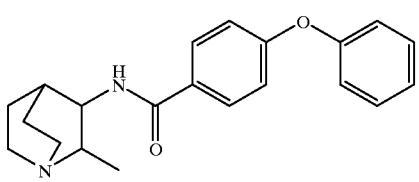

-continued

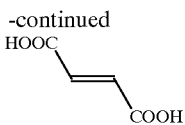

Step K: Preparation of 2-methylenequinuclidin-3-one.

A mixture of 2-methylene-3-quinuclidinone dihydrate hydrochloride (25.7 g, 0.1225 mol, leq) and $K_2CO_3$ (67.0 g, 0.4848 mol, 4eq) is dissolved in 125 mL water and 200 mL $CH_2Cl_2$ and stirred vigorously. After 16 h, the layers are separated and the aqueous layer is extracted with $CH_2Cl_2$. The combined organic layers are dried over $MgSO_4$, filtered and concentrated to give 14.75 g (88%) of 2-methylenequinuclidin-3-one as a yellow oil. MS (ESI) for $C_8H_{11}NO$ m/z 138.1 $(M+H)^+$.

Step L: Preparation of 2-methylquinuclidin-3-one hydrochloride.

The product from Step K (14.75 g, 0.1075 mol, 1 eq), formic acid (10.4 g, 0.2150 mol, 2 eq) and $(Ph_3P)_3RuCl_2$ (0.21 g, 0.21 mmol) are dissolved in 100 mL THF. The mixture is heated under reflux. Fresh portions of catalyst (0.58 g, 0.59 mmol (total)) and formic acid (1.2 g, 0.026 mol) are added periodically over the course of the reaction. After 72 h, the mixture is concentrated in vacuo. The residue is taken up in ether and excess HCl in dioxane (27 mL, 4.0 M) is added. The solids are washed with ether and recrystallized from EtOH to afford 14.4 g (76%) of 2-methylquinuclidin-3-one hydrochloride as a white solid. MS (ESI) for $C_8H_{13}NO$ m/z 140.2 $(M+H)^+$.

Step M: Preparation of 2-methyl-1-azabicyclo[2.2.2]octan-3-one oxime.

2-Methylquinuclidin-3-one hydrochloride from Step L (5.3 g, 30.2 mrol, 1 eq), hydroxylamine hydrochloride (2.5 g, 36.4 mmol, 1.2 eq) and sodium acetate trihydrate (12.4 g, 90.9 mmol, 3 eq) are suspended in 70 mL EtOH and stirred at room temperature. After 24 h, the mixture is concentrated in vacuo. The residue is suspended in $CHCl_3$ and the solids are filtered. The solids are rinsed with excess $CH_3CN$. The combined organic washes are concentrated in vacuo to give 4.65 g (100%) of 2-methyl-1-azabicyclo[2.2.2]octan-3-one oxime. MS (ESI) for $C_8H_{14}N_2O$ m/z 155.2 $(M+H)^+$.

Step N: Preparation of 2-methylquinuclidin-3-amine dihydrochloride.

Sodium (7.0 g, 0.303 mol, 10 eq) is added in portions to a solution of 2-methyl-1-azabicyclo[2.2.2]octan-3-one oxime from Step M (4.65 g, 30.2 mmol, 1 eq) in 100 mL n-propanol. The mixture is heated under reflux. After about 12 h, the mixture is cooled and 80 mL of water is added. The layers are separated and the aqueous layer is extracted with $CHCl_3$. The combined organic layers are dried over $MgSO_4$ and filtered. An excess of HCL in dioxane (lSmL, 4.0 M) is added to solution and the solvent is removed to give 6.0 g (93%) of 2-methylquinuclidin-3-amine dihydrochloride as an oil. A hygroscopic solid is obtained by trituration of the oil in hot IPA. MS (ESI) for $C_8H_{16}N_2$ m/z 141.3 $(M+H)^+$.

Step O: Preparation of N-(2-methyl-1-azabicyclo[2.2.2]oct-3-yl)-4-phenoxy-benzamide fumarate.

TEA (0.32 mL, 2.3 mmol, 1 eq) is added to a solution of 4-phenoxybenzoic acid (0.50 g, 2.3 mmol, 1 eq) in 15mL THF. Diphenylchlorophosphate (0.44 mL, 2.3 mmol, leq) is added and the mixture is stirred at room temperature. After 0.5 h, a suspension of 2-methylquinuclidin-3-amine dihydrochloride from Step N (0.49 g, 2.3 mmol, 1 eq) and TEA (1.30 mL, 9.2 mmol, 4 eq) in THF is added and the resulting mixture is stirred overnight at room temperature. 1N NaOH is added and the aqueous layer is extracted with $CHCl_3$. The combined organic layers are dried over $MgSO_4$, filtered and concentrated to provide 0.64 g (82%) of N-(2-methyl-1-azabicyclo[2.2.2]oct-3-yl)-4-phenoxybenzamide. MS (ESI) for $C_{21}H_{24}N_2O_2$ m/z 337.3 $(M+H)^+$. The fumaric acid salt of the product is made and crystallized from IPA to give the product as a white solid. Reverse phase HPLC (ZORBAX Eclipse XDB-C8, 4.6 mm×15cm, 75:5:20 $H_2O/CH_3CN/$ IPA) reveals an 85:15 trans/cis mixture of isomers.

The present invention also includes, by representation but not limitation, any one of the following or combination of the following compounds and pharmaceutically acceptable salts thereof, both of which can be made by one of ordinary skill in the art using the procedures provided making non-critical changes:

N-[(2S,3R)-2-methyl-1-azabicyclo[2.2.2]oct-3-yl]-4-(4-hydroxyphenoxy)benzamide; N-[(2S,3R)-2-methyl-1-azabicyclo[2.2.2]oct-3-yl]-4-(4-acetamidophenoxy) benzamide; N-[(2S,3R)-2-methyl-1-azabicyclo[2.2.2]oct-3-yl]-4-phenoxybenzamide; N-[(2S,3R) -2-methyl-1-azabicyclo [2.2.2]oct-3-yl]-4-benzylbenzamide; N-[(2S,3R)-2-methyl-1-azabicyclo[2.2.2]oct-3-yl]-4-(phenylsulfanyl) -benzamide; N-[(2S,3R)-2-methyl-1-azabicyclo[2.2.2]oct-3-yl]-3-phenoxybenzamide; N-[(2S,3R)-2-methyl-1-azabicyclo[2.2.2]oct-3-yl]-4-benzoylbenzamide; N-[(2 S,3R) -2-methyl-1-azabicyclo[2.2.2]oct-3-yl]-4-(4-fluorophenoxy) benzamide; N-[(2S,3R)-2-methyl-1-azabicyclo[2.2.2]oct-3-yl]-4-(2-fluorophenoxy)benzamide; N-[(2S,3R)-2-methyl-1-azabicyclo[2.2.2]oct-3-yl]-4-(3-fluorophenoxy)benzamide; N-[(2S,3R)-2-methyl-1-azabicyclo[2.2.2]oct-3-yl]-4-(2-chlorophenoxy)benzamide; N-[(2S,3R)-2-methyl-1-azabicyclo[2.2.2]oct-3-yl]-4-(3-chlorophenoxy)benzamide; N-[(2S,3R)-2-methyl-1-azabicyclo[2.2.2]oct-3-yl]-4-(4-chlorophenoxy)benzamide; N-[(2S,3R)-2-methyl-1-azabicyclo[2.2.2]oct-3-yl]-4-(2-methoxyphenoxy)benzamide; N-[(2S,3R)-2-methyl-1-azabicyclo[2.2.2]oct-3-yl]-4-(3-methoxyphenoxy) benzamide; N-[(2S,3R)-2-methyl-1-azabicyclo[2.2.2]oct-3-yl]-4-(4-methoxyphenoxy)benzamide; N-[(2S,3R)-2-methyl-1-azabicyclo[2.2.2]oct-3-yl]-4-(3-chlorophenylsulfanyl) -benzamide; N-[(2S,3R)-2-methyl-1-azabicyclo[2.2.2]oct-3-yl]-4-(4-chlorophenylsulfanyl) -benzamide; N-[(2S,3R)-2-methyl-1-azabicyclo[2.2.2]oct-3-yl]-4-(2-chlorophenylsulfanyl)-benzamide; N-[(2S,3R)-2-methyl-1-azabicyclo[2.2.2]oct-3-yl]-4-(4-methoxyphenylsulfanyl)-benzamide; N-[(2S,3R)-2-methyl-1-azabicyclo[2.2.2]oct-3-yl]-4-(3-methoxyphenylsulfanyl)-benzamide; N-[(2S,3R)-2-methyl-1-azabicyclo[2.2.2]oct-3-yl]-4-(2-methoxyphenylsulfanyl)-benzamide; N-[(2S,3R)-2-methyl-1-azabicyclo[2.2.2]oct-3-yl]4-phenoxybenzamide; N-[(3R)-1-azabicyclo[2.2.2]oct-3-yl]-4-(4-aminophenoxy)benzamide; N-[(3R)-1-azabicyclo[2.2.2]oct-3-yl]-4-(3-aminophenoxy)benzamide; N-[(3R)-1-azabicyclo[2.2.2]oct-3-yl]-4-(2-aminophenoxy)benzamide; N-[(3R)-1-azabicyclo[2.2.2]oct-3-yl]-4-(4-methanesulfonylamino-phenoxy)benzamide; N-[(3R)—l-azabicyclo[2.2.2]oct-3-yl-4-(3-methanesulfonylamino-phenoxy)benzamide; N-[(3R)-1-azabicyclo[2.2.2]oct-3-yl]-4-(2-methanesulfonylamino-phenoxy)benzamide; N-[(3R)— -azabicyclo[2.2.2]oct-3-yl]4-(4-acetoxyphenoxy)benzamide; N-[(3R)-1-azabicyclo[2.2.2] oct-3-y l]-4-(3-acetoxyphenoxy)benzamide; N-[(3R)-1-azabicyclo[2.2.2]oct-3-yl]-4-(2-acetoxyphenoxy) benzamide; N-[(3R)-1-azabicyclo[2.2.2]oct-3- yl]-4-(4-acetylphenoxy)benzanide; N-[(3R)-1-azabicyclo[2.2.2]oct-3-yl]-4-(3-acetylphenoxy)benzamide; N-[(3R)-1-azabicyclo[2.2.2]oct-3-yl]-4-(2-acetylphenoxy)benzamide; N-[(3R)-1-azabicyclo 2.2.2]oct-3-yl]-4-(4-carbamoylphenoxy)

benzamide; N-[(3R)-azabicyclo[2.2.2]oct-3-yl]-4-(3-carbamoylphenoxy)benzamide; N-[(3R)-1-azabicyclo[2.2.2]oct-3-yl]-4-(2-carbamoylphenoxy)benzarn-ide; N-[(3R)-1-azabicyclo[2.2.2]oct-3-yl]-4-(4-cyanophenoxy)benzamide; N-[(3R)-1-azabicyclo[2.2.2]oct-3-yl]4-(3-cyanophenoxy)benzamide; N-[(3R)-1-azabicyclo[2.2.2]oct-3-yl]-4-(2-cyanophenoxy)benzamide; N-[(3R)-1-azabicyclo[2.2.2]oct-3-yl]-4-(4-sulfamoylphenoxy)benzamide; N-[(3R)-1-azabicyclo[2.2.2]oct-3-yl]-4-(3-sulfamoylphenoxy)benzamide; N-[(3R)-1-azabicyclo[2.2.2]oct-3-yl]-4-(2-sulfamoylphenoxy)benz:de; N-[(3R)-1-azabicyclo[2.2.2]oct-3-yl]-4-(thiophen-2-yloxy)-benzamide; N-[(3R)-1-azabicyclo[2.2.2]oct-3-yl]-4-(5-methy-thiophen-2-yloxy)-benzamide; N-[(3R)-1-azabicyclo[2.2.2]oct-3-yl]-4-(5-chlorothiophen-2-yloxy)benzanide; N-[(3R)-1-azabicyclo [2.2.2]oct-3-yl]-4-(5-nethoxythiophen-2-yloxy)-benzamide; N-[(3R )-1-azabicyclo [2.2.2]oct-3-yl]-4-(2-cyanophenoxy)benzamide; N-[(3R)-1-azabicyclo[2.2. 2]oct -3-yl-1-4-(5-acety-thiophen-2-yloxy)-benzamide; N-[(3R )-1-azabicyclo[2.2.2]oct-3-yl]4-(5-acetar inothiophen-2-yloxy)-benzamide; N-[(3R )-1-azabicyclo[2.2.2]oct-3-yl]-4-(5-cyanothiophen-2-yloxy)-benzamide; N-[(3R)-1-azabicyclo[2.2.2]oct-3-yl]-4-(5-morpholin-4-yl-thiophen-2-yloxy)-benzamide; N-[(3R)-1-azabicyclo[2.2.2]oct-3-yl]-4-(4-methy-thiophen-2-yloxy)-benzamide; N-[(3R)-1-azabicyclo[2.2.2]oct-3-yl]-4-(4-chlorothiophen-2-yloxy)-benzamide; N-[(3R)-1-azabicyclo[2.2.2]oct-3-yl]-4-(4-methoxythiophen-2-yloxy)benzamiide; N-[(3R)-1-azabicyclo[2.2.2]oct-3-yl]-4-(4-trifluoromethy-thiophen-2-yloxy)-benzamide; N-[(3R)-1-azabicyclo[2.2.2]oct-3-yl]-4-(4-acety-thiophen-2-yloxy)-benzamide; N-[(3R)-1-azabicyclo[2.2.2]oct-3-yl]-4-(4-acetaminothiophen-2-yloxy)-benzamide; N-[(3R)-1-azabicyclo[2.2.2]oct-3-yl]-4-(4-cyanothiophen-2-yloxy)-benzamide; N-[(3R) -1-azabicyclo[2.2.2]oct-3-yl]-4-(4-morpholin-4-yl-thiophen-2-yloxy)-benzamide; N-[(3R)-1-azabicyclo[2.2.2]oct-3-yl]-4-(furan-2-yloxy)-benzamide; N-[(3R)-1-azabicyclo[2.2.2]oct-3-yL]-4-(5-methylfuran-2-yloxy)-benzamide; N-[(3R)-1-azabicyclo[2.2.2]oct-3-yl]4-(5-chlorofuran-2-yloxy)-benzamide; N-[(3R)-1-azabicyclo[2.2.2]oct-3-yl]-4-(5-metboxyfuran-2-yloxy)-benzamide; N-[(3R)-1-azabicyclo[2.2.2]oct-3-y-]-4-(5-trifluoromethylfuran-2-yloxy)-benzamide; N-[(3R)-1-azabicyclo[2.2.2]oct-3-yl]-4-(5-acetylfuran-2-yloxy)-benzamide; N-[(3R)-1-azabicyclo[2.2.2]oct-3-yl]-4-(5-acetamiinofuran-2-yloxy)-benzamide; N-[(3R)-1-azabicyclo[2.2.2]oct-3-yl]-4-(5-cyanofuran-2-yloxy)-benzamide; N-[(3R)-1-1-azabicyclo[2.2.2]oct-3-yl]-4-(4-methylfuran-2-yloxy)-benzamide; N-[(3R)-1-azabicyclo[2.2.2]oct-3-yl]4-(4-chlorofuran-2-yloxy)-benzamide; N-[(3R)-1-azabicyclo[2.2.2]oct-3-yl]-4-(4-methoxyfuran-2-yloxy)-benzamide; N-[(3R)-1-azabicyclo[2.2.2]oct-3-yl]-4-(4-trifluoromethylfuran-2-yloxy)-benzamide; N-[(3R)-1-azabicyclo[2.2.2]oct-3-yl]-4-(4-acetylfuran-2-yloxy)benzarniide; N-[(3R)-1-azabicyclo[2.2.2]oct-3-yl]-4-(4-acetaminofuran-2-yloxy)-benzamide; N-[(3R)-1-azabicyclo[2.2.2]oct-3-yl]-4-(4-cyanofuran-2-yloxy)-benzamide; N-[(3R)-1-azabicyclo[2.2.2]oct-3-yl]-4-(4-morpholin-4-yl-furan-2-yloxy)-benzamide; N-[(3R) -1-azabicyclo[2.2.2]oct-3-yl]-4-(oxazol-2-yloxy)— benzamide; N-[(3R)-1-azabicyclo[2.2.2]oct-3-yl]4-(5-methyloxazol-2-yloxy)-benzamide; N-[(3R)-1-azabicyclo[2.2.2]oct-3-yl]-4-(5-chlorooxazol-2-yloxy)-benzamide; N-[(3R)-1-azabicyclo[2.2.2]oct-3-yl]-4-(5- methox yoxazol-2-yloxy)-benzamide; N-[(3R)-1-azabicyclo[2.2.2]oct-3-yl]-4-(5-trifluorometnyloxazol-2-yloxy)-benzamide; N-[(3R)-1-azabicyclo[2.2.2]oct-3-yl]-4-(5-acetyloxazol-2-yloxy)-benzamide; N-[(3R)-1-azabicyclo[2.2.2]oct-3-yl]-4-(5-acetaminooxazol-2-yloxy)-benzamide; N-[(3R)-1-azabicyclo[2.2.2]oct-3-yl]-4-(5-cyanooxazol-2-yloxy)-benzamide; N-[(3R)-1-azabicyclo[2.2.2]oct-3-yl]-4-(5-morpholin-4-yl-oxazol-2-yloxy)-benzamide; N-[(3R)-1-azabicyclo[2.2.2]oct-3-yl]-4-(oxazol-2-yloxy)-benzamide; N-[(3R)-1-azabicyclo[2.2.2]oct-3-yl]-4-(4-methyloxazol-2-yloxy)-benzamide; N-[(3R)-1-azabicyclo[2.2.2]oct-3-yl]4-(4-chlorooxazol-2-yloxy)-benzamide; N-[(3R)-1-azabicyclo[2.2.2]oct-3-yl]-4-(4-methoxyoxazol-2-yloxy)-benzamide; N-[(3R)-1-azabicyclo[2.2.2]oct-3-yl]-4-(4-trifluoromethyloxazol-2-yloxy)-benzamide; N-[(3R)-1-azabicyclo[2.2.2]oct-3-yl]-4-(4-acetyloxazol-2-yloxy)-benzamide; N-[(3R)-1-azabicyclo[2.2.2]oct-3-yl]-4-(4-acetaminooxazol-2-yloxy)-benzamide; N-[(3R)-1-azabicyclo[2.2.2]oct-3-yl]-4-(4-cyanooxazol-2-yloxy)-benzamide; N-[(3R)-1-azabicyclo[2.2.2]oct-3-yl]-4-(4-morpholin-4-yl-oxazol-2-yloxy)-benzamide; N-[(3R) -1-azabicyclo[2.2.2]oct-3-yl]-4-(oxazol-5-yloxy)benza,ide; N-[(3R)-1-azabicyclo[2.2.2]oct-3-yl]-4-(2-methyloxazol-5-yloxy)-benzamide; N-[(3R )-1-azabicyclo[2.2.2]oct-3-yl]-4-(2-chlorooxazol-5-yloxy)benz.de; N-[(3R)-1-azabicyclo[2.2.2]oct-3-yl]-4-(2-methoxyoxazol-5-yloxy)-benzamide; N-[(3R)-1-N-[(3R)-1-azabicyclo[2.2.2]oct-3-yl]-4-(2-acetyloxazol-5-yloxy)-benzamide; N-[(3R)-1-azabicyclo[2.2.2]oct-3-yl]-4-(2-acetaniinooxazol-5-yloxy)-benzamide; N-[(3R)-1-azabicyclo[2.2.2]oct-3-yl]4-(2-cyanooxazol-5-yloxy)-benzamide; N-[(3R)-1-azabicyclo[2.2.2]oct-3-yl]-4-(2-morpholin-4-yl-oxazol-5-yloxy)-benzamide; N-[(3R) -1-azabicyclo[2.2.2]oct-3-yl]-4-(thi azol-2- yloxy)-benzamide; N-[(3R)-1-azabicyclo[2.2.2]oct-3-yl]-4-(5-methylthiazol-2-yloxy)-benzamide; N-[(3R)-1-azabicyclo[2.2.2]oct-3-yl]-4-(5-chlorothiazol-2-yloxy)-benzamide; N-[(3R)-1-azabicyclo[2.2.2]oct-3-yl]-4-(5-methoxythiazol-2-yloxy)-benzamide; N-[(3R)-1-azabicyclo[2.2.2]oct-3-yl]4-(thiazol-2-yloxy)-benzamide; N-[(3R )-1-azabicyclo[2.2.2]oct-3-yl]-4-(5-acetylthiazol-2-yloxy)-benzamide; N-[(3R)-1-azabicyclo[2.2.2]oct-3-yl]-4-(5-acetaminothiazol-2-yloxy)-benzamide; N-[(3R)-1-azabicyclo[2.2.2]oct-3-yl]-4-(5-cyanothiazol-2-yloxy)-benzamide; N-[(3R)-1-azabicyclo[2.2.2]oct-3-yl]-4-(5-morpholino4-yl-thiazol-2-yloxy)-benzamide; N-[(3R)-1-azabicyclo[2.2.2]oct-3-yl]-4-(thiazol-2-yloxy)-benzamide; N— [(3R)-1-azabicyclo[2.2.2]oct-3-yl]4-(4-methylthiazol-2-yloxy)-benzamide; N-[(3R)-1-azabicyclo[2.2.2]oct-3-yl]-4-(4-chlorothiazol-2-yloxy)-benzamide; N-[(3R)-1-azabicyclo[2.2.2]oct-3-yl]-4-(4-methoxythiazol-2-yloxy)-benzamide; N-[(3R)-1-azabicyclo[2.2.2]oct-3-yl]4-(4-trifluoromethylthiazol-2-yloxy)-benzamide; N-[(3R) -1-azabicyclo[2.2.2]oct-3-yl]4-(4-acetylthiazol-2-yloxy)-benzamide; N-[(3R)-1-azabicyclo[2.2.2]oct-3-yi]-4-(4-acetaminothiazol-2-yloxy)-benzamide; N-[(3R)-1-azabicyclo[2.2.2]oct-3-yI]4-(4-cyanothiazol-2-yloxy)-benzamide; N-[(3R)-1-azabicyclo[2.2.2]oct-3-yl]-4-(4-morpholin-4-yl-thiazol-2-yloxy)-benzamide; N-[(3R) -1-azabicyclo[2.2.2]oct-3-yl]-4-(thiazol-5-yloxy)-benzamide; N-[(3R)-1-azabicyclo[2.2.2]oct-3-yl]-4-(2-methylthiazol-5-yloxy)-benzamide; N-[(3R)-1-azabicyclo[2.2.2]oct-3-yl]-4-(2-chlorothiazol-5-yloxy)-benzamide; N-[(3R)-1-azabicyclo[2.2.2]oct-3-yl]-4-(2-methoxythiazol-5-yloxy)-benzamide; N-[(3R)-1-N-[(3R)-1-azabicyclo[2.2.2]oct-3-yl]4-(2-ac etylthiazol-5- yloxy)-benzamide; N-[(3R)-1-azabicyclo[2.2.2]oct-3-yl]4-(2-acetarninothiazol-5-yloxy)-benzamide; N-[(3R)-1-azabicyclo[2.2.2]oct-3-yl]-4-(2-cyanothiazol-5-yloxy)-benzamide; N-[(3R)-1-azabicyclo[2.2.2]oct-3-y1-4-(2-morpholin-4-yl-thiazol-5-yoxy)benzamide; N-[(3R) -1- azabicyclo[2.2.2]oct-3-yl]-4-([1,3c,4oxadiazol-2-yloxy)-benzamide; N-[(3R)-1-azabicyclo[2.2.2]oct-3-yl]-4-(5-methyl[1,3,4]oxadiazol-2-yloxy)-benzamide; N -[(3R)-1-azabicyclo[2.2.2]oct-3-yl]-4-(5-chloro[1,3,4]oxadiazol-2-yloxy)-benzamide; N-[(3R)-1-azabicyclo[2.2.2]oct -3-yl]-4-(5-methoxy[1,3,4]oxadiazol-2-yloxy) -benzamide; N-[(3R)-1-azabicyclo[2.2.2]oct-3-yl]-4-(5-trifluoromethyl[1,3,4]oxadiazol-2-yloxy)-benzamide; N-[(3R)-1-azabicyclo[2.2.2]oct-3-yl]-4-(5-acetyl[1,3,4]oxadiazol-2-yloxy)-benzamide; N-[(3R) -1-azabicyclo[2.2.2]oct-3-yl]-4-(5-acetamino[1,3,4]oxadiazol-2-yloxy)-benzamide; N -[(3R)-1-azabicyclo[2.2.2]oct-3-yl]-4-(5-cyano[1,3,4]oxadiazol-2-yloxy)-benzamide; N-[(3R)-1-azabicyclo[2.2.2]oct-3-yl]-4-(5-morpholin-4-yl-[1,3,4]oxadiazol-2-yloxy) -benzamide; N-[(3R)-1-azabicyclo[2.2.2]oct-3-yl]-4-([1,3,4]thiadiazol-2-yloxy) -benzamide; N-[(3R)-1-azabicyclo[2.2.2]oct-3-yl]-4-(5-methyl[1,3,4]thiadiazol-2-yloxy)-benzamide; N-[(3R)-1-azabicyclo[2.2.2]oct-3-yl]-4-(5-chloro[1,3,4]thiadiazol -2-yloxy)-benzamide; N-[(3R)-1-azabicyclo[2.2.2]oct-3-yl]-4-(5-methoxy[1,3,4thiadiazol-2-yloxy)-benzamide; N-[(3R)-1-azabicyclo[2.2.2]oct-3-yl]-4-(5-trifluoromethyl[1,3,4]thiadiazol-2-yloxy)-benzamide; N-[(3R)-1-azabicyclo[2.2.2]oct-3-yl]-4-(5-acetyl[1,3,4]thiadiazol-2-yloxy)-benzamide; N-[(3R) -1-azabicyclo[2.2.2]oct-3-yl]4-(5-acetarnino[1,3,4]thiadiazol-2-yloxy)-benzamide; N -[(3R)-1-azabicyclo[2.2.2]oct-3-yl]-4-(5-cyano[1,3,4]thiadiazol-2-yloxy)-benzamide; N-[(3R)-1-azabicyclo[2.2.2]oct-3-yl]-4-(5-morpholin-4-yl-[1,3,4]thiadiazol-2-yloxy) -benzamide; N-[(3R)-1-azabicyclo[2.2.2]oct-3-yl]-4-(4-aminophenylsulfanyl) -benzamide; N-[(3R)-1-azabicyclo[2.2.2]oct-3-yl]-4-(3-aminophenylsulfanyl) -benzamide; N-[(3R)-1-azabicyclo[2.2.2]oct-3-yl]-4-(2-aminophenylsulfanyl) -benzamide; N-[(3R)-1-azabicyclo[2.2.2]oct-3-yl]-4-(4-methanesulfonylamino -phenylsulfanyl)-benzarmide; N-[(3R)-1-azabicyclo[2.2.2]oct-3-yl]-4-(3-methanesulfonylamino-phenylsulfanyl)-benzamide; N-[(3R)-1-azabicyclo[2.2.2]oct -3-yl]-4-(2-methanesulfonylamino-phenylsulfanyl)-benzamide; N-[(3R)-1-azabicyclo[2.2.2]oct-3-yl]-4-(4-acetoxyphenylsulfanyl)-benzamide; N-[(3R)-1-azabicyclo[2.2.2]oct-3-yl]-4-(3-acetoxyphenylsulfan)-benzamide; N-[(3R)-1-azabicyclo[2.2.2]oct-3-yl]4-(2-acetoxyphenylsulfanyl)-benzamide; N-[(3R)-1-azabicyclo[2.2.2]oct-3-yl]-4-(4-acetylphenylsulfanyl)-benzamide; N-[(3R)-1-azabicyclo[2.2.2]oct-3-yl]-4-(3-acetylphenylsulfanyl)-benzamide; N-[(3R)-1-azabicyclo[2.2.2]oct-3-yl]-4-(2-acetylphenylsulfanyl)-benzamide; N-[(3R)-1-azabicyclo[2.2.2]oct-3-yl]-4-(4-carbamoylphenylsulfanyl)-benzamide; N-[(3R)-1-azabicyc:o[2.2.2]oct-3-yl]-4-(3-carbamoylphenylsulfanyl)-benzamide; N-[(3R)-2-azabicyclo[2.2.2]oct-3-yl]-4-(2-carbamoylphenylsulfanyl)-benzamide; N-[(3R)-1-azabicyclo[2.2.2]oct-3-yl]-4-(4-cyanophenylsulfanyl)-benzamide; N-[(3R)-1-azabicyclo[2.2.2]oct-3-yl]-4-(3-cyanophenylsulfanyl)-benzamide; N-[(3R)-1-azabicyclo[2.2.2]oct-3-yl]-4-(2-cyanophenylsulfanyl)-benzamide; N-[(3R)-1-azabicyclo[2.2.2]oct-3-y]-4-(4-sulfamoylphenylsulfanyl)-benzamide; N-[(3R)-1-azabicyclo[2.2.2]oct-3-yl]-4-(3-sulfamoylphenylsulfanyl)-benzamide; N-[(3R)-1-azabicyclo[2.2.2]oct-3-yl]-4-(2-sulfamoylphenylsulfanyl)-benzamide; N-[(3R)-1-azabicyclo[2.2.2]oct-3-yl]-4-(4-hydroxyphenylsulfanyl)-benzamide; N-[(3R)-1-azabicyclo[2.2.2]oct-3-yl]-4-(3-hydroxyphenylsulfanyl)-benzamide; N-[(3R)-1-azabicyclo[2.2.2]oct-3-yl]-4-(2-hydroxyphenylsulfanyl)-benzamide; N-[(3R)-1-azabicyclo[2.2.2]oct-3-yl]-4-(4-acetamidophenylsulfanyl)-benzamide; N-[(3R)-1-azabicyclo[2.2.2]oct-3-yl]-4-(3-acetaridophenylsulfanyl)-benzamide; N-[(3R)-1-azabicyclo[2.2.2]oct-3-yl]-4-(2-acetanidophenylsulfanyl)-benzamide; N-[(3R)-1-azabicyclo[2.2.2]oct-3-yl]-4-(thliopihen-2-ylsulfanyl)-benzamide; N-[(3R)-1-azabicyclo[2.2.2]oct-3-yl]-4-(5-methy-thiophen-2-ylsulfanyl)-benzamide; N-[(3R)-1-azabicyclo[2.2.2]oct-3-yl]-4-(5-chlorothiophen-2-yisulfanyl)-benzamide; N-[(3R)-1-azabicyclo[2.2.2]oct-3-yl]-4-(5-methoxythiophen-2-ylsulfanyl)-benzamide; N-[(3R) -1-azabicyclo[2 .2.2]oct-3-yl]-4-(5-trifluoromethy-thiophen-2-ylsulfanyl)-benzamide; N-[(3R)-1-azabicyclo[2.2.2]oct-3-yl]-4-(5-acety-thiophen-2-ylsulfanyl)-benzamide; N-[(3R)-1-azabicyclo[2.2.2]oct-3-yl]-4-(5-acetaminothiophen-2-ylsulfanyl) -benzamide; N-[(3R)-1-azabicyclo[2.2.2]oct-3-yl]-4-(5-cyanothiophen-2-ylsulfanyl) -benzamide; N-[(3R)-1-azabicyclo[2.2.2]oct-3-yl]-4-(5-morpholin-4-yl-thiophen-2-ylsulfanyl)-benzamide; N-[(3R)-1-azabicyclo[2.2.2]oct-3-yl]-4-(4-methy-thiophen-2-ylsulfanyl)-benzamide; N-[(3R)-1-azabicyclo[2.2.2]oct-3-yl]4-(4-chlorothiophen-2-ylsulfanyl)-benzamide; N-[(3R)-1-azabicyclo[2.2.2]oct-3-yl]-4-(4-methoxythiophen -2-ylsulfanyl)-benzamide; N-[(3R)-1-azabicyclo[2.2.2]oct-3-yl]-4-(4-trifluoromethy-thiophen-2-ylsulfanyl)-benzamide; N-[(3R)-1-azabicyclo[2.2.2]oct-3-yl]-4-(4-acety-thiophen-2-ylsulfanyl)-benzamide; N-[(3R)-1-azabicyclo[2.2.2]oct-3-yl]-4-(4-acetaminothiophen-2-ylsulfanyl)-benzamide; N-[(3R)-1-azabicyclo[2.2.2]oct-3-yl]-4-(4-cyanothiophen-2-ylsulfanyl)-benzamide; N-[(3R)-1-azabicyclo[2.2.2]oct-3-yl-4-(4-morpholin-4-yl-thiophen-2-ylsulfanyl) --benzamide; N-f(3R)-1-azabicyclo[2.2.2]oct-3-yl]-4-(furan-2-ylsulfanyl)-benzamide; N-[(3R)-lI-azabicylo[2.2.2]oct-3-yl]-4-(5-methylfuran-2-ylsulfanyl)-benzamide; N -[(3R)-1-azabicyclo[2.2.2]oct-3-yl]-4-(5-chlorofuran-2-ylsulfanyl)-benzamide; N -[(3R)-1-azabicyclo[2.2.2]oct-3-yl]-4-(5-methoxyfuran-2-ylsulfanyl)-benzarniide; N -[(3R)-1-azabicyclo[2.2,2]oct-3-yl]-4-(5-trifluoromethylfuran-2-ylsulfanyl)-benzamide; N-[(3R)-1-azabicyclo[2.2.2]oct-3-yl]-4-(5-acetylfuran-2-ylsulfanyl)-benzamide; N-[(3R)-1-azabicyclo[2.2.2]oct-3-yl]-4-(5-acetarninofuran-2-ylsulfanyl)-benzaide; N -[(3R)-1-azabicyclo[2.2.2]oct-3-yl]-4-(5-cyanofuran-2-ylsulfanyl)-benzamide; N -[(3R)-1-azabicyclo[2.2.2]oct-3-yl]-4-(5-morpholin-4-yl-furan-2-ylsulfanyl) --benzamide; N-[(3R)-1-azabicyclo[2.2.2]oct-3-yl]-4-(4-methylfuran-2-ylsulfanyl) -benzamide; N-[(3R)-1-azabicyclo[2.2.2]oct-3-yl]-4-(4-chlorofuran-2-ylsulfanyl) -benzamide; N-[(3R)-1-azabicyclo[2.2.2]oct-3-yl]-4-(4-methoxyfuran-2-ylsulfanyl) -benzamide; N-[(3R)-1-azabicyclo[2.2.2]oct-3-yl]-4-(4-trifluoromethylfuran-2-ylsulfanyl)-benzamide; N-[(3R)-1-azabicyclo[2.2.2]oct-3-yl]-4-(4-acetylfuran-2-ylsulfanyl)-benzamide; N-[(3R)-1-azabicyclo[2.2.2]oct-3-yl]-4-(4-acetaminofuran-2-ylsulfanyl)-benzamide; N-[(3R)-1-azabicyclo[2.2.2]oct-3-yl]-4-(4-cyanofuran-2-ylsulfanyl)-benzamide; N-[(3R)-1-azabicyclo[2.2.2]oct-3-yl]-4-(4-morpholin-4-yl -furan-2-ylsulfanyl)-benzamide; N-[(3R)-1-azabicyclo[2.2.2]oct-3-yl]-4-(oxazol-2-ylsulfanyl)-benzamide; N-[(3R)-1-azabicyclo[2.2.2]oct-3-yl]-4-(5-methyloxazol-2-ylsulfanyl)-benzamide; N-[(3R)-1-azabicyclo[2.2.2]oct-3-yl]-4-(5-chlorooxazol-2-ylsulfanyl)-benzamide; N-[(3R)-1-azabicyclo[2.2.2]oct-3-yl]-4-(5-methoxyoxazol-2-ylsulfanyl)-benzamide; N-[(3R)-1-azabicyclo[2.2.2]oct-3-yl]-4-(5-trifluoromethyloxazol-2-ylsulfanyl)-benzamide; N-[(3R)-1-azabicyclo[2.2.2]oct-3-yl]-4-(5acetyloxazol-2-ylsulfanyl)-benzamide; N-[(3R)-1-azabicyclo[2.2.2]oct-3-yl]-4-(5acetaminooxazol-2-ylsulfanyl)-benzamide; N-[(3R)-1-azabicyclo[2.2.2]oct-3- yl]-4-(5cyanooxazol-2-ylsulfanyl)-benzamide; N-[(3R)-1-azabicyclo[2.2.2]oct-3-yl]-4-(5morpholin-4-yl-oxazol-2-ylsulfanyl)-benzamide; N-[(3R)-1-azabicyclo[2.2.2]oct-3-yl]-4-(oxazol-2-ylsulfanyl)-benzamide; N-[(3R)-1-azabicyclo[2.2.2]oct-3-yl]-4-(4-methyloxazol-2-ylsulfanyl)-benzanide; N-[(3R)-1-azabicyclo[2.2.2]oct-3-yl]-4-(4-chlorooxazol-2-ylsulfanyl)-benzamide; N-[(3R)-1-azabicyclo[2.2.2]oct-3-yl]-4-(4-methoxyoxazol-2-ylsulfanyl)-benzamide; N-[(3R)-1-azabicyclo[2.2.2]oct-3-yl]-4-(4-methyoxazol -2-ylsulfanyl)- -benzamide; N -[(3R)-1-azabicyclo -[2.2.2]oct-3-yl]-4-(4- acetyloxazol-2-ylsulfanyl)-benzamide; N -[(3R)-1-N-[(3R)-1-azabicyclo[2.2.2]oct-3-yl]-4-(4-cyanooxazol-2-ylsulfanyl)-benzamide; N -[(3R)-1-azabicyclo[2.2.2]oct-3-yl]-4-(4-morpholin-4-yl-oxazol-2-ylsulfanyl) -benzamide; N-[(3R)-1-azabicyclo[2.2.2]oct -3-yl]-4-(oxazol-5-ylsulfanyl)-benzamide; N(3R)-1-azabicyclo[2.2.2]oct-3-yl]-4-(2meth yloxazol-5-ylsulfanyl) -[(3R)-1-azabicyclo[2.2.2]oct-3-yl]-4-(2chloro oxazol-5-ylsulfanyl)-benzamide; N -[(3R)-1-azabicyclo [2.2.2]oct-3-yl]-4-(2methoxyoxazol-5-ylsulfanyl)-benzamide; N -[(3R)-1-azabicyclo[2.2.2]oct-3-yl]-4-(2trfluoromethyloxazol -5-ylsulfanyl) -benzamide; N-[(3R)-1-azabicyclo[2.2.2]oct-3-yl]-4-(2acetyloxazol-5-ylsulfanyl) -benzamide; N-[(3R)-1-azabicyclo[2.2.2]oct-3-yl]-4-(2acetaminooxazol -5-ylsulfanyl)-benzamide ; N-[(3R)-1-azabicyclo[2.2.2]oct-3-yl]-4-(2cy anooxazol -5-ylsulfanyl)-benzamide; N-[(3R)-1-azabicyclo[2.2.2 ]oct-3-yl]-4-(2norpholin-4-yl -oxazol-5-ylsulfanyl)-benzamide; N-[(3R)-1-azabicyclo[2.2.2]oct-3-yl]-4-(thiazol-2-ylsulfanyl)-benzamide; N-[(3R)-1-azabicyclo[2.2.2]oct-3-yl]]-(5methy(thiazol-2-ylsulfanyl)-benzamide; N-[(3R)-1-azabicyclo[2.2.2]oct-3-yl]-4-(5chlorothiazol-2-ylsulfanyl)-benzamide; N-[(3R)-1-azabicyclo[2.2.2]oct-3-yl]-4-(5methoxythiazol-2-ylsulfanyl)-benzamide; N-[(3R)-1-azabicyclo[2.2.2]oct-3-yl]-4-(5-trifluoromethylthiazol-2-ylsulfanyl)-benzamide; N-[(3R)-1-azabicyclo[2.2.2]oct-3-yl]-4-(5acetylthiazol-2-ylsulfanyl)-benzamide; N-[(3R)-1-azabicyclo[2.2.2]oct-3-yl]-4-(5acetaminothiazol-2-ylsulfanyl)-benzamide; N-[(3R)-1-azabicyclo[2.2.2]oct-3-yl ]-4-(5cyanothiazol-2-ylsulfanyl)-benzamide; N-[(3R)-1-azabicyclo[2.2.2]oct-3-yl]-4-(5morpholin-4-yl-thiazol-2-ylsulfanyl)-benzamide; N-[(3R)-1-azabicyclo[2.2.2]oct-3-yl]-4-(thiazol-2-ylsulfanyl)-benzamide; N-[(3R)-1-azabicyclo[2.2.2]oct-3-yl]-4-(4-methylthiazol-2yisulfanyl)-benzamide; N-[(3R)-1-azabicyclo[2.2.2]oct-3-yl]-4-(4-chlorothiazol-2-ylsulfanyl)-benzamide; N-[(3R)-1-azabicyclo[2.2.2]oct-3-yl]-4-(4-methoxythiazol-2-ylsulfanyl)-benzamide; N-[(3R)-1-azabicyclo[2.2.2]oct-3-yl]-4-(4-trifluoromethylthiazol-2-ylsulfanyl)-benzamide; N -[(3R)-1-azabicyclo[2.2.2]oct-3-ylR-4-(4-acetylthiazol-2yisulfanyl)-benzamide; N -[(3R)-1-azabicyclo[2.2.2oct-3-yl]-4-(4-acetaninothiazol-2-ylsulfanyl)-benzamide; N-[(3R)-1-azabicyclo[2.2.2]oct-3-yl]-4-(4-cyanothiazol-2-ylsulfanyl)-benzanide; N -[(3R)-1-azabicyclo[2.2.2]oct-3-yl]-4-(4-morpholin-4-yl-thiazol-2-ylsulfanyl) -benzamide; N-[(3R)-1-azabicyclo[2.2.2]oct-3-yl]-4-(thiazol-5-ylsulfanyl)-benzamide; N-[(3R)-1-azabicyclo[2.2.2]oct-3-yl]-4-(thiazol-5-ylsulfanyl)-benzamide; N -[(3R)-1-azabicyclo[2.2.2]oct-3-yl]-4-(2chlorothiazol-5-ylsulfanyl)-benzamide; N -[(3R)-1-azabicyclo[2.2.2]oct-3-yl]-4-(2methoxythiazol-5-ylsulfanyl)-benzamide; N -[(3R)-1-azabicyclo[2.2.2]oct-3-yl]-4-(2trfluoromethylthiazol-5-ylsulfanyl) -benzamide; N-[(3R)-1-azabicyclo[2.2.2]oct-3-yl]-4-(2acetylthiazol -5-ylsulfanyl) -benzamide; N-[(3R)-1-azabicyclo[2.2.2]oct-3-yl]-4-(2acetaminothiazol-5-ylsulfanyl)-benzamide; N-[(3R)-1-azabicyclo[2.2.2]oct-3-yl]-4-(2cyanothiazol-5-ylsulfanyl)-benzamide; N-[(3R)-1-azabicyclo[2.2.2]oct-3-yl]-4-(2morphoin-4-yl -thiazol-5-ylsulfanyl)-benzamide; N-[(3R)-1-azabicyclo -[2.2.2]oct-3-yl]-4-([1,3,4]oxadiazol-2-ylsulfanyl)-benzamide; N-[(3R)-1-azabicyclo[2.2.2]oct -3-yl]-4(5methyl-[,3,4]oxadiazol-2-ylsulfanyl)-benzamide; N-[(3R )-1-azabicyclo[2.2.2]oct -3-yl]-4-(5chloro-[1,3,4]oxadiazol-2-ylsulfanyl)-benzamide; N-[(3R)-1-azabicyclo[2.2.2]oct-3-yl]-4-(5methoxy-[1 ,3,4]oxadiazol-2-ylsulfanyl)-benzamide; N-[(3R)-1-azabicyclo[2.2.2]oct-3-yl]-4-(5-trifluoromethyl-[1 ,3,4]oxadiazol-2-ylsulfanyl)-benzamide; N-[(3R)-1-azabicyclo[2.2.2]oct-3-yl]-4-(5acetyl-[1,3,4] oxadiazol-2-ylsulfanyl)-benzamide; N-[(3R)-1-azabicyclo [2.2.2]oct-3-yl]-4-(5acetamino-[1,3,4]oxadiazol-2-ylsulfanyl)-benzamide; N-[(3R)-1-azabicyclo[2.2.2]oct-3-yl]-4-(5cyano-[1,3,4]oxadiazol-2-ylsulfanyl)-benzamide; N -[(3R)-1-azabicyclo[2.2.2]oct-3-yl3-4-(5morpholin-4-yl-[1 ,3,4]oxadiazol-2-ylsulfanyl)-benzamide; N-[(3R)-1-azabicyclo[2.2.2]oct-3-yl]-4-([1,3,4]thiadiazol-2-ylsulfanyl)-benzamide; N-[(3R)-1-azabicyclo[2.2.2]oct-3-yl]-4-(5methyl-[1,3,4]thiadiazol-2-ylsulfanyl)-benzamide; N-[(3R)-1-azabicyclo[2.2.2]oct-3-yl]-4-(5chloro-[1,3,4] thiadiazol-2-ylsulfanyl)-benzamide; N-[(3R)-1-azabicyclo [2.2.2]oct-3-yl]-4-(5methoxy-[1,3,4]thiadiazol-2-ylsulfanyl)-benzamide; N-[(3R)-1-azabicyclo[2.2.2]oct-3-yl]-4-(5-trifluoromethyl-[1 ,3,4]thiadiazol-2-ylsulfanyl)-benzamide; N-[(3R)-1-azabicyclo[2.2.2]oct-3-yl]-4-(5acetyl-[1,3,4]thiadiazol-2-ylsulfanyl)-benzamide; N-[(3R)-1-azabicyclo[2.2.2]oct-3-yl]-4-(5acetamino-[1,3,4] thiadiazol-2-ylsulfanyl)-benzarfide; N-[(3R)-1-azabicyclo [2.2.2]oct-3-yl]-4-(5cyano-[1,3,4]thiadiazol-2-ylsulfanyl)-benzamide; N -[(3R)-1-azabicyclo[2.2.2]oct-3-yl]-4-(5morpholin-4-yl-[1,3,4]thiadiazol-2-ylsulfanyl)-benzamide; N-[(3R)-.-azabicyclo[2.2.2]oct-3-yl]-4-(pyrrol-2-yloxy) -benzamide; N-[(3R)-1-azabicyclo[2.2.2]oct-3--yl]-4-(5methylpyrrolrrol-2-yloxy) -benzamide; N-[(3R)-1-azabicyclo[2.2.2]oct-3-yl]-4-(5chloropyrrol-2-yloxy) -benzamide; N-[(3R)-1-azabicyclo[2.2.2]oct-3-yl]-4-(5methoxypyrrol-2-yloxy) -benzamide; N-[(3R)-1-azabicyclo[2.2.2]oct-3-yi]-4-(5-trifluoromethylpyrrolrrol-2-yloxy)-benzamide; N-[(3R)-1-azabicyclo[2.2.2]oct-3-yl]-4-(5acetylpyrrol-2-yloxy) -benzamide; N-[(3R)-1-azabicyclo [2.2.2]oct-3-yl]-4-(5acetaniinopyrrol-2-yloxy) -benzamide; N-[(3R)-1-azabicyclo[2.2.2]oct-3-yl]-4-(5cyanopyrrol-2-yloxy) -benzamide; N-[(3R)-1-azabicyclo[2.2.2]oct-3-yl]-4-(5morpholin-4-yl-pyrrol-2-yloxy)-benzamide; N-[(3R)-1-azabicyclo[2.2.2]oct-3-yl]-4-(3H-imidazol-4-yloxy) -benzamide; N-[(3R)-1-azabicyclo[2.2.2]oct-3-yl]-4-(2methyl-3H -imidazol-4-yloxy) -benzamide; N-[(3R)-1-azabicyclo[2.2.2]oct-3-yl]-4-(2chloro-3H-imidazo2-4-yloxy) -benzamide; N-[(3R)-1-azabicyclo[2.2.2]oct-3-yl]-4-(2methoxy-3H$_4$- idazol-4-yloxy) -benzamide; N-[(3R)-1-azabicyclo[2.2.2]oct-3-yl]-4-(2trifluoromethyl-3H-imidazol-4-yloxy)-benzamide; N-[(3R)-1-azabicyclo[2.2.2]oct-3-yl]-4-(2acetyl-3H-imidazol-4 -yloxy)-benzamide; N-[(3R)-1-azabicyclo[2.2.2]oct-3-yl]-4-(2acetamino-3H-imidazol-4-yloxy)-benzamide; N-[(3R)-1-azabicyclo[2.2.2] oct-3-yl]-4-(2cyano -3H-imidazol-4-yloxy)-benzamide; N-[(3R)-1-azabicyclo[2.2.2]oct-3-yl]-4-(2-morpholin-4-yl-3imidazol-4-yloxy)-benzamide; N-[(3R)-1-azabicyclo [2.2.2]oct-3-yl]-3-(isoxazol-2-yloxy)-benzamide; N-[(3R)-1-azabicyclo[2.2.2]oct-3-yl]-4-(5-methylisoxazol-3-yloxy)-benzamide; N-[(3R)-1-azabicyclo[2.2.2]oct-3-yl]-4-(5-chloroisoxazol-3-yloxy)-benzamide; N-[(3R)-1-azabicyclo [2.2.2]oct-3-yl]-4-(5-methoxyisoxazol-3-yloxy)-benzamide; N-[(3R)-1-azabicyclo[2.2.2]oct-3-yl]-4-(5-trifluoromethylisoxazol-3-yloxy)-benzamide; N-[(3R)-1-azabicyclo[2.2.2]oct-3-yl]-4-(5acetylisoxazol-3-yloxy)- benzamide; N-[(3R)-1-azabicyclo[2.2.2]oct-3-yl]-4-(5-acetaminoisoxazol-3-yloxy)-benzamide; N-[(3R)-1-azabicyclo[2.2.2]oct-3-yl]-4-(5-5 cyanoisoxazol-3-yloxy)-benzamide; N-[(3R)-1-azabicyclo[2.2.2]oct-3-yl]-4-(5-morpholin-4-yl-isoxazol-3-yloxy)-benzamide; N-[(3R)-1-azabicyclo[2.2.2]oct-3-yl]-4-(isothiazol-2-yloxy)-benzamide; N-[(3R)-1-azabicyclo[2.2.2]oct-3-yl]-4-(5-methyl-isothiazol-3-yloxy)-benzamide; N-[(3R)-1-azabicyclo[2.2.2]oct-3-yl]-4-(5-chloroisothiazol-3-yloxy)-benzamide; N-[(3R)-1-azabicyclo[2.2.2]oct-3-yl]-4-(5-methoxyisothiazol-3-yloxy)-benzamide; N-[(3R)-1-azabicyclo[2.2.2]oct-3-yl]-4-(5-trifluoromethyl-isothiazol-3-yloxy)-benzamide; N-[(3R)-1-azabicyclo[2.2.2]oct-3-yl]-4-(5-acetyl-isothiazol-3-yloxy)-benzamide; N-[(3R)-1-azabicyclo[2.2.2]oct-3-yl]-4-(5-acetactinoisothiazol-3-yloxy)-benzamide; N-[(3R)-1-azabicyclo[2.2.2]oct-3-yl]-4-(5-cyanoisothiazol-3-yloxy)-benzamide; N-[(3R)-1-azabicyclo[2.2.2]oct-3-yl]-4-(5-morpholin-4-yl-sothiazol-3-yloxy)-benzamide; N-[(3R)-1-azabicyclo -[2.2.2]oct-3-yl]-4-(pyrrol-2-ylsulfanyl)-benza mide; N-[(3R)-1-azabicyclo[2.2.2]oct-3- y l]-4-(5-methylpyrrolrrol-2-ylsulfanyl)-benzamide; N-[(3R)-1-azabicyclo[2.2.2]oct-3-yl]-4-(5-chloropyrrol-2-ylsulfanyl)-benzamide; N-[(3R)-1-azabicyclo[2.2.2]oct-3-yl]-4-(5-methoxypyrrol-2-ylsulfanyl)-benzamide; N-[(3R)-1-azabicyclo[2.2.2]oct-3-yl]-4-(5-trfluoromethylpyrrolrrol-2-ylsulfanyl)-benzamide; N-[(3R)-1-azabicyclo[2.2.2]oct-3-yl]-4-(5-acetylpyrrol-2-ylsulfanyl)-benzamide; N-[(3R)-1-azabicyclo[2.2.2]oct-3-yl]-4-(5-acetahninopyrrol-2-ylsulfanyl)-benzamide; N-[(3R)-1-azabicyclo[2.2.2]oct-3-yl]-4-(5-cyanopyrrol-2-ylsulfanyl)—benza mide; N-[(3R)-1-azabicyclo[2.2.2]oct-3-yl]-4-(5-morpholin-4-yl-pyrr ol-2-ylsulfanyl)-benzamide; N-[(3R)-1-azabicyclo[2.2.2]oct -3-yl]-4-(3H-iniodazol-4-ylsulfanyl)-benzamide; N-[(3R)-1-azabicyclo[2.2.2]oct-3-yl]-4-(2-methyl-3H-imidazol-4-ylsulfanyl)-benzamide; N-[(3R)-1-azabicyclo[2.2.2]oct-3-yl]-4-(2-chloro-3H-imidazol-4-ylsulfanyl)-benzamide; N-[(3R)-1-azabicyclo[2.2.2]oct-3-yl]-4-(2-methoxy-3H-imidazol-4-ylsulfanyl)-benzamide; N -[(3R)-1-azabicyclo[2.2.2]oct-3-yl]-4-(2-trifluoromethyl-3H-imidazol-4-ylsulfanyl) -benzamide; N-[(3R)-1-azabicyclo[2.2.2]oct-3-yl]-4-(2-acetyl-3H-imidazol-4-ylsulfanyl)-benzamide; N-[(3R)-1-azabicyclo[2.2.2]oct-3-yl]-4-(2-acetamino-3H -imidazol-4-ylsulfanyl)-benzamide; N-[(3R)-1-azabicyclo[2.2.2]oct-3-yl]-4-(2-cyano -3H-imidazol-4-ylsulfanyl)-benzamide; N-[(3R)-1-azabicyclo[2.2.2]oct-3-yl]-4-(2-morpholin-4-yl-3H-imidazol-4-ylsulfanyl)-benzamide; N-[(3R)-1-azabicyclo[2.2.2]oct-3-yl]-4-(isoxazol-2-ylsulfanyl)-benzamide; N-[(3R)-1-azabicyclo[2.2.2]oct-3-yl]-4-(5-methylisoxazol-3-ylsulfanyl)-benzamide; N-[(3R)-1-azabicyclo[2.2.2]oct-3-yl]-4-(5-chloroisoxazol-3-ylsulfanyl)-benzamide; N-[(3R)-1-azabicyclo[2.2.2]oct-3-yl]-4-(5-methoxyisoxazol-3-ylsulfanyl)-benzamide; N-[(3R) -1-azabicyclo[2.2.2]oct-3-yl]-4-(5-trifluoromethylisoxazol-3-ylsulfanyl)-benzamide; N-[(3R)-1-azabicyclo[2.2.2]oct-3-yi]-4-(5-acetylisoxazol-3-ylsulfanyl)-benzamide; N-[(3R)-1-azabicyclo[2.2.2]oct-3-yl]-4-(5-acetaminoisoxazol-3-ylsulfanyl) -benzamide; N-[(3R)-1-azabicyclo[2.2.2]oct-3-yl]-4-(5-cyanoisoxazol-3-ylsulfanyl) -benzamide; N-[(3R)-1-azabicyclo[2.2.2]oct-3-yl]-4-(5-morpholin-4-yl-isoxazol-3-ylsulfanyl)-benzamide; N-[(3R)-1-azabicyclo[2.2.2]oct-3-yl]-4-(isothiazol-2-ylsulfanyl)-benzamide; N-[(3R)-1-azabicyclo[2.2.2]oct-3-yl]-4-(5-methyl-isothiazol-3-ylsulfanyl)-benzamide; N.-[(3R)-1-azabicyclo[2.2.2]oct-3-yl]-4-(5-chloroisothiazol-3-ylsulfanyl)-benzamide; N-[(3R)-1-azabicyclo[2.2.2]oct-3-yl]-4-(5-methoxyisothiazol-3-ylsulfanyl)-benzamide; N-[(3R)-1-azabicyclo[2.2.2]oct-3-yl]-4-(5-trifluoromethyl-isothiazol-3-ylsulfanyl)-benzamide; N-[(3R)-1-azabicyclo[2.2.2]oct-3-yl]-4-(5-acetyl-isothiazol-3-ylsulfanyl)-benzamide; N-[(3R)-1-azabicyclo[2.2.2]oct-3-yl]-4-(5-acetaminoisothiazol-3-ylsulfanyl)-benzamide; N-[(3R)-1-azabicyclo[2.2.2]oct-3-yl]-4-(5-cyanoisothiazol-3-ylsulfanyl)-benzamide; N-[(3R)-1-azabicyclo[2.2.2]oct-3-yl]-4-(5-morpholin-4-yl-isothiazol-3-ylsulfanyl)-benzamide; N-[(3R)-1-azabicyclo[2.2.2]oct-3-yl]-4-(6-methylpyrrolridin-3-yloxy)-benzamide; N -[(3R)-1-azabicyclo[2.2.2]oct-3-yl]-4-(6-chloropyridin-3-yloxy)-benzamide; N-[(3R)-1-azabicyclof2.2.2]oct-3-yl]-4-(6-methoxypyridin-3-yloxy)-benzamide; N-[(3R)-1-azabicyclo[2.2.2]oct-3-yl]-4-(6-trifluoromethylpyrrolridin-3-yloxy)-benzamide; N-[(3R)-1-azabicyclo[2.2.2]oct-3-yl]-4-(6-acetylpyridin-3-yloxy)-benzamide; N-[(3R)-1-azabicyclo[2.2.2]oct-3-yl]-4-(6-acetaminopyridin-3-yloxy)-benzamide; N-[(3R)-1-azabicyclo[2.2.2]oct-3-yl]-4-(6-cyanopyridin-3-yloxy)-benzamide; N-[(3R)-1-azabicyclo[2.2.2]oct-3-yl]-4-(6-morpholin-4-yl-pyridin-3-yloxy)-benzamide; N -[(3R)-1-azabicyclo[2.2.2]oct-3-yl]-4-(2-methylpyrrolridin-4-yloxy)-benzamide; N-[(3R) -1-azabicyclo[2.2.2]oct-3-yl]-4-(2-chloropyridin-4-yloxy)-benzamide; N-[(3R)-1-azabicyclo[2.2.2]oct-3-yl]-4-(2-methoxypyridin-4-yloxy)-benzamide; N-[(3R)-1-azabicyclo[2.2.2]oct-3-yl]-4-(2-trifluoromethylpyrrolridin-4-yloxy)-benzamide; N-[(3R)-1-azabicyclo[2.2.2]oct-3-yl]-4-(2-acetylpyridin-4-yloxy)-benzamide; N-[(3R)-1-azabicyclo[2.2.2]oct-3-yl]-4-(2-acetaminopyridin-4-yloxy)-benzamide; N-[(3R)-1-azabicyclo[2.2.2]oct-3-yl]-4-(2-cyanopyridin-4-yloxy)-benzamide; N-[(3R)-1-azabicyclo[2.2.2]oct-3-yl]-4-(2-morpholin-4-yl-pyridin-4-yloxy)-benzamide; N -[(3R)-1-azabicyclo[2.2.2]oct-3-yl]-4-(5-methylpyrrolridin-2-yloxy)-benzamide; N-[(3R) -1-azabicyclo[2.2.2]oct-3-yl]-4-(5-chloropyridin-2-yloxy)-benzamide; N-[(3R)-1-azabicyclo[2.2.2]oct-3-yl]-4-(5-methoxypyridin-2-yloxy)-benzamide; N-[(3R)-1-azabicyclo[2.2.2]oct-3-yl]-4-(5-trifluoromethylpyrrolridin-2-yloxy)-benzamide; N-[(3R) -1-azabicyclo[2.2.2]oct-3-yl]-4-(5-acetylpyridin-2-yloxy)-benzamide; N-[(3R)-1-azabicyclo[2.2.2]oct-3-yl]-4-(5-acetaminopyridin-2-yloxy)-benzamide; N-[(3R)-1-azabicyclo[2.2.2]oct-3-yl]-4-(5-cyanopyridin-2-yloxy)-benzamide; N-[(3R)-1-[(3R)-1-azabicyclo[2.2.2]oct-3-ylJ-4-(4-methylpyrrolridin-2-yloxy)-benzamide; N-[(3R) -1I-azabicyclo[2.2.2]oct-3-yl]-4-(4-chloropyridin-2-yloxy)-benzamide; N-[(3R)-1-azabicyclo[2.2.2]oct-3-yl]-4-(4-methoxypyridin-2-yloxy)benzarmide; N-[(3R)-1az N-[(3R) -1-azabicyclo[2.2.2]oct-3-yl]-4-(4-acetylpyridin-2-yloxy)-benzamide; N-[(3R)-1-azabicyclo[2.2.2]oct-3-yl]-4-(4-acetaminopyridin-2-yloxy)-benzamide; N-[(3R)-1-azabicyclo[2.2.2]oct-3-yl]-4-(4-cyanopyridin-2-yloxy)-benzamide; N-[(3R)-1-[(3R)-1-azabicyclo[2.2.2]oct-3-yl]-4- (6-methylpyrrolridin-2-yloxy)-benzamide; N-[(3R) 1.-azabicyclo[2.2.2]oct-3-yl]-4-(6-chloropyridin-2-yloxy)-benzamide; N(3R)-1-azabicyclo[2.2.2]oct-3-yl]-4-(6-methoxypyridin-2-yloxy)-benzamide; N-[(3R)-1az N-[(3R) -1-azabicyclo[2.2.2]oct-3-yl]-4-(6-acetylpyridin-2-yloxy)-benzamide; N-[(3R)-1-azabicyclo[2.2.2]oct-3-yl]-4-(6-acetaminopyridin-2-yloxy)-benzamide; N-[(3R)-1-azabicyclo[2.2.2]oct-3-yl]-4-(6-cyanopyridin-2-yloxy)-benzamide; N-[(3R)-1-azabicyclo[2.2.2]oct-3-yl]-4-(4-morpholin-4-yl-pyridin-2-yloxy)-benzamide; N -[(3R)-1-azabicyclo[2.2.2]oct-3-yl]-4-(5-methylpyrrolridin-3-yloxy)-benzamide; N-[(3R) l-azabicyclo[2.2.2]oct-3-yl]-4-(5-chloropyridin-3-yloxy)-benzamide; N-[(3R)-1-azabicyclo[2.2.2]oct-3-yl]-4-(5-methoxypyridin-3-yloxy)-benzamide;

N-[(3R)-1-azabicyclo[2.2.2]oct-3-yl]-4-(6-trifluoromethylpyrrolridin-2-yloxy)-benzamide; N-[(3R)-1-azabicyclo[2.2.2]oct-3-yl]-4-(5-acetylpyridin-3-yloxy)-benzamide; N-[(3R)-1-azabicyclo[2.2.2]oct-3-yl]-4-(5-acetaminopyridin-3-yloxy)-benzamide; N-[(3R)-1-azabicyclo(2.2.2]oct-3-yl]-4-(5-cyanopyridin-3-yloxy)-benzamide; N— -[(3R)-1-azabicyclo[2.2.2]oct-3-yl]-4-(5-morpholin-4-yl-pyridin-3-yloxy)-benzamide; N -[(3R)-1-azabicyclo[2.2.2]oct-3-yl]-4-(2-chloropyridin-3-yloxy)-benzamide; N-[(3R) 1-azabicyclo[2.2.2]oct-3-yl]-4-(4-chloropyridin-3-yloxy)-benzamide; N-[(3R)-1-azabicyclo[2.2.2]oct-3-yl]-4-(3chloropyridin-4-yloxy)-benzamide; N-[(3R)-1-azabicyclo[2.2.2]oct-3-yl]-4-(3chloropyridin-2-yloxy)-benzamide; N-[(3R)-1-azabicyclo[2.2.2]oct-3-yl]-4-(6-methylpyrrolridin-3-ylsulfanyl)-benzamide; N-[(3R)-1-azabicyclo[2.2.2]oct-3-yl]-4-(6-chloropyridin-3-ylsulfanyl)-benzamide; N-[(3R)-1-azabicyclo[2.2.2]oct-3-yl]-4-(6-methoxypyridin-3-ylsulfanyl)-benzamide; N-[(3R)-1-azabicyclo[2.2.2]oct-3-yl]-4-(6-trifluoromethylpyrrolridin-3-ylsulfanyl)-benzamide; N -[(3R)-1-azabicyclo[2.2.2]oct-3-yl]-4-(6-acetylpyridin-3-ylsulfanyl)-benzamide; N -[(3R)— z -n N-[(3R)-1-azabicyclo[2.2.2]oct-3-yl]-4-(6-cyanopyridin-3-ylsulfanyl)-benzamide; N -[(3R)-1-azabicyclo[2.2.2]oct-3-yl]-4-(6-morpholin-4-yl-pyridin-3-ylsulfanyl) -benzanide; N-[(3R)-1-azabicyclo[2.2.2]oct-3-yl]1-4-(2-methylpyrrolridin-4-ylsulfany) -benzamide; N-[(3R)-1-azabicyclo[2.2.2]oct-3-yl]-4-(2-chloropyridin-4-ylsulfanyl) -benzamide; N-[(3R)-1-azabicyclo[2.2.2]oct-3-yl]-4-(2-methoxypyridin-4-ylsulfanyl) -benzamide; N-[(3R)-1-azabicyclo[2.2.2]oct-3-yl]-4-(2trirfluoromethylpyrrolridin-4-ylsulfanyl)-benzamide; N-[(3R)-1-azabicyclo[2.2.2]oct-3-yl ]-4(2-acetylpyridin-4-ylsulfanyl)-benzamide; N-[(3R)-1-azabicyclo[2.2.2]oct-3-yl 1-4(2-acetamnopyinin-4-4-ylsulfanyl)-benzamide; N-[(3R)-1-azabicyclo[2.2.2]oct-3-yl]-4-(2-cyanopyridin-4-ylsulfanyl)-benzamide; N-[(3R)-1-azabicyclo[2.2.2]oct-3-yl]-4-(2-morpholin-4yl -pyridin-4-ylsulfanyl)-benzamide; N-[(3R)-1-azabicyclo[2.2.2]oct-3-yl]-4-(5-methylpyrrolridin-2-ylsulfanyl)- -benzamide; N-[(3R)-1-azabicyclo[2.2.2]oct-3-yl]-4-(5-chloropyridin-2-ylsulfanyl)- -benzamide; N-[(3R)-1-azabicyclo[2.2.2]oct-3-yl]-4-(5-methoxypyridin-2-ylsulfanyl)- -benzamide; N-[(3R)-1-azabicyclo[2.2.2]oct-3-yl]-4-(5-trifluoromethylpyrrolridin-2-ylsulfanyl)- -benzamide; N-[(3R)-1-azabicyclo[2.2.2]oc t-3-yl]-4-(5-acetylpyridin-2-ylsulfanyl)-benzamide; N-[(3R)-1-azabicyclo[2.2.2]oct-3-yl]-4-(5-acetaminopyridin-2-ylsulfanyl)-benzamide; N-[(3R)-1-azabicyclo[2.2.2 ]oct-3yl]-4-(5-cyanopyridin-2-ylsulfanyl)-benzamide; N-[(3R)-1-azabicyclo[2.2.2]oct-3-yl]-4-(5-morpholin-4yl-pyridin-2-ylsulfanyl)-benzamide; N-[(3R)-1-azabicyclo[2.2.2]oct-3-yl]-4-(4methylpyrrolridin-2-ylsulfanyl)-benzamide; N-[(3R)-1-azabicyclo[2.2.2]oct-3-yl]-4-(4chloropyridin-2-ylsulfanyl)-benzamide; N-[(3R)-1-azabicyclo[2.2.2]oct-3-yl]-4-(4methoxypyridin-2-ylsulfanyl)-benzamide; N-[(3R)-1-azabicyclo[2.2.2]oct-3-yl]-4-(4trifluoromethylpyrrolridin-2-ylsulfanyl)-benzamide; N -[(3R)-1-azabicyclo2.2.2]oct-3-yl]-4-(4-acetylpyridin-2-ylsulfanyl)-benzamide; N -[(3R)-1-azabicyclo[2.2.2]oct-3-yl]-4-(4acetaminopyridin-2-ylsulfanyl)-benzamide; N-[(3R)-1-azabicyclo[2.2.2]oct-3-yl]-4-(4cyanopyridin-2-ylsulfanyl)-benzamide; N -[(3R)-1-azabicyclo[2.2.2]oct-3-yl]-4-(4morpholin-4yl-pyridin-2-ylsulfanyl) -benzamide; N-[(3R)-1-azabicyclo[2.2.2]oct-3-yl]-4-(6-methylpyrrolridin-2-ylsulfanyl) -benzamide; N-[(3R)-1-azabicyclo[2.2.2]oct-3-yl]-4-(6-chloropyridin-2-ylsulfanyl) -benzamide; N-[(3R)-1-azabicyclo[2.2.2]oct-3-yl]-4-(6-methoxypyridin-2-ylsulfanyl) -benzamide;

N-[(3R)-1-azabicyclo[2.2.2]oct-3-yl]-4-(6-trifluoromethylpyrrolridin-2-ylsulfanyl)-benzamide; N-[(3R)-1-azabicyclo[2.2.2]oct-3yI]-4-(6-acetylpyridin-2-ylsulfanyl)-benzamide; N-[(3R)-1-azabicyclo[2.2.2]oct-3-yl]-4-(6-acetaminopyridin -2-ylsulfanyl)-benzamide; N-[(3R)-1-azabicyclo[2.2.2]oct-3-yl]-4-(6-cyanopyridin-2-ylsulfanyl)-benzamide; N-[(3R)-1-azabicyclo[2.2.2]oct-3-yl]-4-(6-morpholin-4yl -pyridin-2-ylsulfanyl)-benzamide; N-[(3R)-1-azabicyclo[2.2.2]oct-3-yl]-4-(5-methylpyrrolridin-3-ylsulfanyl)-benzamide; N-[(3R)-1-azabicyclo[2.2.2]oct-3-yl]-4-(5-chloropyridin-3-ylsulfanyl)-benzamide; N-[(3R)-1-azabicyclo[2.2.2]oct -3-yl]-4-(5-methoxypyridin-3-ylsulfanyl)-benzamide; N-[(3R)-1-azabicyclo[2.2.2]oct-3-yl]-4-(5-trifluoromethylpyrrolridin-3-ylsulfanyl)-benzamide; N-[(3R)-1-azabicyclo[2.2.2]oct -3-yl]-4-(5-acetylpyridin-3-ylsulfanyl)- -benzamide; N-[(3R)-1-azabicyclo[2.2.2]oct -3-yl]-4-(5-acetaniinopyridin-3-ylsulfanyl)-benzamide; N-[(3R)-1-azabicyclo[2.2.2]oct-3-yl]-4-(5-cyanopyridin-3-ylsulfanyl)-benzamide; N-[(3R)-1-azabicyclo[2.2.2]oct-3-yl]-4-(5-morpholin-4yl-pyridin-3-ylsulfanyl)-benzamide; N-[(3R )-1-1-azabicyclo[2.2.2]oct-3-yl]-4-(2-chloropyridin-3-ylsulfanyl)-benzamide; N-[(3R)-1-1-azabicyclo[2.2.2]oct-3-yl]-4-(4chloropyridin-3-ylsulfanyl)-benzamide; N-[(3R)-1azabicyclo[2.2.2oct-3'- -yl]-5-chloropyridin-3-ylsulfanyl)-benzamide; N-[(3R)-1-azabicyclo[2.2.2]oct-3-yl]-4-(3chloropyridin-2-ylsulfanyl)-benzamide; N-[(2S,3R)-2-methyl-1-azabicyclo[2.2.2]oct -3-yl]-4-(4aminophenoxy)benzamide; N-[(2S,3R) -2-methyl-1-azabicyclo[2.2.2]oct-3-yl]-4-(3aminophenoxy )-benzamide; N-[(2S,3R) -2-methyl-1-azabicyclo[2.2.2]oct-3-yl]-4-(2aminophenoxy)benzamide; N-[(2S,3R) -2-methyl-1-azabicyclo[2.2.2]oct-3-yl]-4-(4methanesulfonylaminophenoxy) -benzamide; N-[(2S,3R)-2-methyl-1-azabicyclo[2.2.2]oct-3-yl]-4-(3methanesulfonylamino-phenoxy)-benzamide; N-[(2S,3R)-2-methyl-1-azabicyclo[2.2.2]oct-3-yl]-4-(2methanesulfonylamino-phenoxy)-benzamide; N -[(2S,3R)-2-methyl-1-azabicyclo[2.2.2]oct-3-yl]-4-(4acetoxyphenoxy)benzamide; N -[(2S,3R)-2-methyl-1-azabicyclo[2.2.2]oct-3-yl]-4-(3acetoxyphenoxy)benzamide; N -[(2S,3R)-2-methyl-1-azabicyclo[2.2.2]oct-3-yl]-4-(2-acetoxyphenoxy)benzamide; N -[(2S,3R)-2-methyl-1-azabicyclo[2.2.2]oct-3-yl]-4-(4acetylphenoxy)benzamide; N -[(2S,3R)-2-methyl-1-azabicyclo[2.2.2]oct-3-yl]-4-(3acetylphenoxy)benzamide; N -[(2S,3R)-2-methyl-1-azabicyclo[2.2.2]oct-3-yl]-4-(2-acetylphenoxy)benzamide; N -[(2S,3R)-2-methyl-1-azabicyclo[2.2.2]oct-3-yl]-4-(4carbamoylphenoxy)benzamide; N-[(2S,3R)-2-methyl-1-azabicyclo[2.2.2]oct-3-yl]-4-(3carbamoylphenoxy) -benzamide; N-[(2S,3R)-2-methyl-1-azabicyclo[2.2.2]oct-3-yl]-4-(2-carbamoylphenoxy)benzamide; N-[(2,,3R)-2-methyl-1-azabicyclo[2.2.2]oct-3-yl]-4-(4cyanophenoxy)benzamide; N-[(2S,3R)-2-methyl-1-azabicyclo[2.2.2]oct-3-yl]-4-(3cyanophenoxy)benzamide; N-[(2S,3R)-2-methyl-1-azabicyclo[2.2.2]oct-3-yl]-4-(2-cyanophenoxy)benzamide; N-[(2S:,3R)-2-methyl-azabicyclo[2.2.2]oct-3-yl]-4-(4sulfamoylphenoxy)benzamide; N-[(2S,3R)-2-methyl-1-azabicyclo[2.2.2]oct-3-yl]-4-(3sulfamoylphenoxy) benzamide; N-[(2S,3R)-2-methyl -11 -azabicyclo[22.2]oct-3-yl]-4-(2sulfamoylphenoxy)benzamide; N-[(2S,3R)-2-methyl-1-azabicyclo[2.2.2]oct-3-yl]-4-(thiophen-2-yloxy)-benzamide; N-[(2S,3R)-2-methyl-1-azabicyclo[2.2.2]oct-3-yl]-4-(5-methy-thiophen-2-yloxy)-benzamide; N -[(2S,3R)-2-methyl-1-azabicyclo[2.2.2]oct-3-yl]-4-(5-chlorothiophen-2-yloxy) -benzamide; N-[(2S,3R)-2-methyl-1-azabicyclo[2.2.2]oct-3-yl]-4-(5-methoxythiophen-2-yloxy)-benzamide; N-[(2S,3R)-2-methyl-1-azabicyclo[2.2.2]oct -3-yl]-4-(5-trifluoromethy-thiophen-2-yloxy)-benzamide; N-[(2S,3R)-2-methyl-1-azabicyclo[2.2.2]oct-3-yl]-4-(5-acety-thiophen-2-yloxy)-benzamide; N-[(2S,3R)-2-methyl-1-azabicyclo[2.2.2]oct-3-yl]-4-(5-acetaminothiophen-2-yloxy)-benzamide; N -[(2S,3R)-2-methyl-1-azabicyclo[2.2.2]oct-3-yl]-4-(5-cyanothiophen-2-yloxy) -benzamide; N-[(2S,3R)-2-methyl-1-azabicyclo[2.2.2]oct-3-yl]-4-(5-morpholin-4yl -thiophen-2-yloxy)-benzamide; N-[(2S,3R)-2-methyl-1-azabicyclo[2.2.2]oct-3-yl]-4-(4methy-thiophen-2-yloxy)-benzamide; N-[(2S,3R)-2-methyl-1-azabicyclo[2.2.2]oct-3-yl]-4-(4chlorothiophen-2-yloxy)benzamiide; N-[(2S,3R)-2-methyl-1-azabicyclo[2.2.2]oct-3-yl]-4-(4methoxythiophen-2-yloxy)-benzamide; N -[(2S,3R)-2-methyl-1-azabicyclo[2.2.2]oct-3-yl]-4-(4trifluoromethy-thiophen-2-yloxy)-benzamide; N-[(2S,3R)-2-methyl-1-azabicyclo[2.2.2]oct-3-yl]-4-(4-acety-thiophen-2-yloxy)-benzamide; N-[(2S,3R)-2-methyl-1-azabicyclo[2.2.2]oct-3-yl]-4-(4acetaminothiophen-2-yloxy)-benzamide; N-[(2S,3R)-2-methyl-1-azabicyclo[2.2.2]oct-3-yl]-4-(4cyanothiophen-2-yloxy)-benzamide; N-[(2S,3R)-2-methyl-1-azabicyclo[2.2.2]oct-3-yl]-4-(4morpholin-4yl-thiophen-2-yloxy) -benzamide; N-[(2S,3R)-2-methyl-1-azabicyclo[2.2.2]oct-3-yl]-4-(furan-2-yloxy) -benzamide; N-[(2S,3R)-2-methyl-1-azabicyclo[2.2.2]oct-3-yl]-4-(5-methylfuran-2-yloxy)-benzamide; N-[(2S,3R)-2-methyl-1-azabicyclo[2.2.2]oct-3-yl]-4-(5-chlorofuran-2-yloxy)-benzamide; N-[(2S,3R)-2-methyl-1-azabicyclo[2.2.2]oct-3-yl]-4-(5-methoxyfuran-2-yloxy)-benzamide; N-[(2S,3R)-2-methyl-1-azabicyclo[2.2.2]oct-3-yl]-4-(5-trifluoromethylfuran-2-yloxy)-benzamide; N -[(2S,3R)-2-methyl-1-azabicyclo[2.2.2]oct-3-yl]-4-(5-acetylfuran-2-yloxy)-benzamide; N-[(2S,3R)-2-methyl-1-azabicyclo[2.2.2]oct-3-yl]-4-(5-acetaminofuran-2-yloxy) -benzamide; N-[(2S,3R)-2-methyl-1-azabicyclo[2.2.2]oct-3-yl]-4-(5-cyanofuran-2-yloxy)-benzamide; N-[(2S,3R)-2-methyl-1-azabicyclo[2.2.2]oct-3-yl]-4-(5-morpholin-4yl-furan-2-yloxy)-benzamide; N-[(2S,3R)-2-methyl-1-azabicyclo[2.2.2]oct-3-yl]-4-(4methylfuran-2-yloxy) -benzamide; N-[(2S,3R)-2-methyl-1-azabicyclo[2.2.2]oct-3-yl]-4-(4chlorofuran-2-yloxy)-benzamide; N -[(2S,3R)-2-methyl-1-azabicyclo[2.2.2]oct-3-yl]-4-(4methoxyfuran-2-yloxy) -benzamide; N-[(2S,3R)-2-methyl-1-azabicyclo[2.2.2]oct-3-yl]-4-(4-trifluoromethylfuran-2-yloxy)-benzamide; N-[(2S,3R)-2-methyl-1-azabicyclo[2.2.2]oct-3-yl]-4-(4acetylfuran-2-yloxy)-benzamide; N-[(2S,3R)-2-methyl-1-azabicyclo[2.2.2]oct-3-yl]-4-(4acetaminofuran-2-yloxy) benzamiide; N -[(2S,3R)-2-methyl-1-azabicyclo[2.2.2]oct-3-yl]-4-(4cyanofuran-2-yloxy)-benzamide; N-[(2S,3R)-2-methyl-1-azabicyclo[2.2.2]oct-3-yl]-4-(4morpholin-4yl-furan-2-yloxy)-benzamide; N-[(2S,3R)-2-methyl-1-azabicyclo[2.2.2]oct-3-yl]-4-(oxazol-2-yloxy)-benzamide; N-[(2S,3R)-2-methyl-1-azabicyclo[2.2.2]oct-3-yl]-4-(5-methyloxazol-2-yloxy)-benzamide; N-[(2S,3R)-2-methyl-1-azabicyclo[2.2.2]oct-3-yl]-4-(5-chlorooxazol-2-yloxy)-benzamide; N-[(2S,3R)-2-methyl-1-azabicyclo[2.2.2]oct-3-yl]-4-(5-methoxyoxazol-2-yloxy)-benzamide; N-[(2S,3R)-2-methyl-1-azabicyclo[2.2.2]oct-3-yl]-4-(5-trifluoromethyloxazol-2-yloxy)benzanide; N-[(2S,3R)-2-methyl-1-azabicyclo[2.2.2]oct-3-yl]-4-(5-acetyloxazol-2-yloxy) -benzamide; N-[(2S,3R)-2-methyl-1-azabicyclo[2.2.2]oct-3-yl]-4-(5-acetaminooxazol 2-yloxy)-benzamide; N-[(2S,3R)-2-methyl-1-azabicyclo[2.2.2]oct-3-yl]-4-(5-cyanooxazol-2-yloxy)-benzamide; N-[(2S,3R)-2-methyl-1-azabicyclo[2.2.2]oct-3-yl]-4-(5-morpholin-4yl-oxazol-2-yloxy)-benzamide; N-[(2S,3R)-2-methyl-1-azabicyclo[2.2.2]oct-3-yl]-4-(oxazol-2-yloxy)-benzamide; N-[(2S,3R)-2-methyl-1-azabicyclo[2.2.2]oct-3-yl]-4-(4methyloxazol-2-yloxy)-benzamide; N-[(2S,3R)-2-methyl-1-azabicyclo[2.2.2]oct-3-yl]-4-(4chlorooxazol-2-yloxy)-benzamide; N -[(2S,3R)-2-methyl-1-azabicyclo[2.2.2]oct-3-yl]-4-(4methoxyoxazol-2-yloxy) -benzamiide; N-[(2S,3R)-2-methyl-1-azabicyclo[2.2.2]oct-3-yl]-4-(4-trifluoromethyloxazol-2-yloxy)-benzamide; N-[(2S,3R)-2-methyl-1-azabicyclo[2.2.2]oct-3-yl]-4-(4acetyloxazol-2-yloxy)-benzamide; N-[(2S,3R)-2-methyl-1-azabicyclo[2.2.2]oct-3-yl]-4-(4acetaminooxazol-2-yloxy)-benzamide; N -[(2S,3R)-2-methyl-1-azabicyclo[2.2.2]oct-3-yl]-4-(4cyanooxazol-2-yloxy) -benzanide; N-[(2S,3R)-2-methyl-1-azabicyclo[2.2.2]oct-3-yl]-4-(4morpholin-4yl -oxazol-2-yloxy)-benzamide; N-[(2S,3R)-2-methyl-1-azabicycio-[2.2.2]oct-3-yl]-4 -(oxazol-5-yloxy)-benzamide; N-[(2S,3R)-2-methyl-1-azabicyclo[2.2.2]oct-3-yl]-4-(2-methyloxazol-5-yloxy)-benzamide; N-[(2S,3R)-2-methy l-1-azabicyclo[2.2.2]oct-3-yl]-4-(2-chlorooxazol-5-yloxy)-benzamide; N-[(2S,3R)-2-methyl -11 -azabicyclo[2.2.2]oct-3-yl]-4-(2-methoxyoxazol-5-yloxy)-benzamide; N-[(2S, 3R)-2-methyl-1-azabloL2.2.2]oct-3-yl]-4-(2-methyoxazol-5-yloxy)benzanide; N-[(2S,3R)-2-methyl-1-azabicyclo[2.2.2]oct-3-yl]-4-(2-acetyloxazol-5-yloxy) -benzamide; N-[(2S,3R)-2-methyl-1-azabicyclo[2.2.2]oct-3-yl]-4-(2-acetaminooxazol -5-yloxy)-benzamide; N-[(2S,3R)-2-methyl-1-azabicycio-[2.2.2]oct-3-yl]-4-(2-cyanooxazol-5-yloxy)-benzamide; N-[(2S,3R)-2-methyl-1-azabicyclo[2.2.2]oct-3-yl]-4-(2-morpholin-4yl-oxazol-5-yloxy)-benzamide; N-[(2S,3R)-2-methyl-1-azabicyclo[2.2.2]oct-3-yl]-4-(thiazol-2-yloxy)-benzamide; N-[(2S,3R)-2-methyl-1-azabicyclo[2.2.2]oct-3-yl]-4-(5-methylthiazol-2-yloxy)-benzamide; N-[(2S,3R)-2-methyl-1-azabicyclo[2.2.2]oct-3-yl]-4-(5-chlorothiazol-2-yloxy)-benzamide; N -[(2S,3R)-2-methyl-1-azabicyclo[2.2.2]oct-3-yl]-4-(5-methoxythiazol-2-yloxy) -benzamide; N-[(2S,3R)-2-methyl-1-azabicyclo[2.2.2]oct-3-yl]-4-(5-trifluoromethylthiazol-2-yloxy)-benzamide; N-[(2S,3R)-2-methyl-1-azabicyclo[2.2.2]oct-3-yl]-4-(5-acetylthiazol-2-yloxy)-benzamide; N-[(2S,3R)-2-methyl-1-azabicyclo[2.2.2]oct-3-yl]-4-(5-acetaminothiazol-2-yloxy)-benzamide; N -[(2S,3R)-2-methyl-1-azabicyclo[2.2.2]oct-3-yl]-4-(5-cyanothiazol-2-yloxy) -benzamide; N-[(2S,3R)-2-methyl-1-azabicyclo[2.2.2]oct-3-yl]-4-(5-morpholin-4yl -thiazol-2-yloxy)-benzamide; N-[(2S,3R)-2-methyl-1-azabicyclo[2.2.2]oct-3-yl]-4-(thiazol-2-yloxy)-benzamide; N-[(2S,3R)-2-methyl-1-azabicyclo[2.2.2]oct-3-yl]-4-(4-methylthiazol-2-yloxy)-benzamide; N-[(2S,3R)-2-methyl-1-azabicyclo[2.2.2]oct-3-yl]-4-(4chlorothiazol-2-yloxy)-benzamide; N-[(2S,3R)-2-methyl-1-azabicyclo[2.2.2]oct-3-yl]-4-(4methoxythiazol-2-yloxy)-benzamide; N-[(2S,3R)-2-methyl-1-azabicyclo[2.2.2]oct-3-yl]-4-(4trifluoromethylthiazol-2-yloxy)-benzamide; N-[(2S,3R)-2-methyl-1-azabicyclo[2.2.2]oct-3-yl]-4-(4acetylthiazol-2-yloxy) -benzamide; N-[(2S,3R)-2-methyl-1-azabicyclo -[2.2.2]oct-3-yl]-4-(4acetaminothiazol -2-yloxy)-benzamide; N-[(2S,3R)-2-methyl-1-azabicyclo[2.2.2]oct-3-yl]-4-(4-cyanothiazol-2-yloxy)-benzamide; N-[(2S,3R)-2-methyl-1-azabicyclo[2.2.2]oct-3-yl]-4-(4morpholin-4yl-thiazol-2-yloxy)-benzamide; N-[(2S,3R)-2-methyl-1-azabicyclo[2.2.2]oct-3-yl]-4-(thiazol-5-yloxy)-benzamide; N-[(2S,3R)-2-methyl-1-azabicyclo[2.2.2]oct-3-yl]-4-(2-methylthiazol-5-yloxy)-benzamide; N-[(2S,3R)-2-methyl-1-azabicyclo[2.2.2]oct-3-yl]-4-(2-chlorothiazol-5-yloxy)-benzamide; N -[(2S,3R)-2-methyl-1-azabicyclo[2.2.2]oct-3-yl]-4-(2-methoxythiazol-5-yloxy) -benzamide; N-[(2S,3R)-2-methyl-1-azabicyclo -[2.2.2]oct-3-yl]-4-(2-trifluoromethylthiazol-5-yloxy)-benzamide; N-[(2S,3R)-2-methyl-1-azabicyclo[2.2.2]oct-3-yl]-4-(2-acetylthiazol-5-yloxy)-benzamide; N-[(2S,3R)-2-methyl-1-azabicyclo

[2.2.2]oct-3-yl]-4-(2-acetahinothiazol-5-yloxy)-benzamide; N -[(2S,3R)-2-methyl-1-azabicyclo[2.2.2]oct-3-yl]-4-(2-cyanothiazol-5-yloxy) -benzamide; N-[(2S,3R)-2-methyl-1-azabicyclo[2.2.2]oct-3-yl]-4-(2-morpholin-4yl -thiazol-5-yloxy)-benzamide; N-[(2S,3R) -2-methyl-1-azabicycio-[2.2.2]oct-3-yl]-4-([1 ,3,4]oxadiazol-2-yloxy)-benzamide; N-[(2S,3R)-2-methyl-1-azabicyclo[2.2.2]oct -3-yl]-4-(5-methyl]-1,3,4]oxadiazol-2yloxy)-benzamide; N-[(2S,3R)-2-methyl-1-azabicyclo[2.2.2]oct-3-yl]-4-(5-chloro-[1,3,4]oxadiazol-2-yloxy)-benzamide; N -[(2S,3R)-2-methyl-1-azabicyclo[2.2.2]oct-3-yl]-4-(5-methoxy1,35,4]oxadiazol-2-yloxy)-benzamide; N-[(2S,3R)-2-methyl-1-azabicyclo[2.2. 2]oct-3-yl]-4-(5-trifluoromethyl[1,3,4]oxadiazol-2-yloxy)-benzamide; N-[(2S,3R)-2-methyl-1-azabicyclo[2.2.2]oct-3-yl]-4-(5-acetyl[1,3,4]oxadiazol-2-yloxy)-benzamide; N -[(2S,3R)-2-methyl-1-azabicyclo[2.2.2]oct-3-yl]-4-(5-acetamino-[1 ,3,4]oxadiazol-2-yloxy)-benzamide; N-[(2S,3R)-2-methyl-1-azabicyclo[2.2.2]oct-3-yl]-4-(5-cyano-[1, 3,4]oxadiazol-2-yloxy)-benzamide; N-[(2S,3R)-2-methyl-1-azabicyclo[2.2.2]oct-3-yl]-4-(5-morpholin-4yl[1 ,3,4]oxadiazol-2-yloxy)-benzamide; N-[(2S,3R)-2-methyl-1-azabicyclo[2.2.2]oct-3-yl]-4-([1,3,4]thiadiazol-2-yloxy) -benzamide; N-[(2S,3R)-2-methyl-1-azabicyclo[2.2.2]oct-3-yl]-4-(5-methyl[1,3,4]thiadiazol-2-yloxy)-benzamide; N-[(2S,3R)-2-methyl-1-azabicyclo[2.2.2]oct-3-yl]-4-(5chloro-[1,3,4]thiadiazol-2-yloxy)-benzamide; N -[(2S,3R)-2-methyl-1-azabicyclo[2.2.2]oct-3-yl]-4-(5methoxy-[1,3,4]thiadiazol-2-yloxy)-benzamide; N-[(2S, 3R)-2-methyl-1-azabicyclo[2.2.2]oct-3-yl]-4-(5-trifluoromethyl[1,3,4]thiadiazol-2-yloxy)-benzamide; N-[(2S,3R)-2-methyl-1-azabicyclo[2.2.2]oct-3-yl]-4-(5acetyl[1,3,4]thiadiazol-2-yloxy)-benzamide; N -[(2S,3R)-2-methyl-1-azabicyclo[2.2.2]oct-3-yl]-4-(5acetamino-[1,3,4]thiadiazol-2-yloxy)-benzamide; N-[(2S,3R)-2-methyl-1-azabicyclo[2.2.2]oct-3-yl]-4-(5-cyano-[1,3,4]thiadiazol-2-yloxy)-benzamide; N-[(2S,3R)-2-methyl-1-azabicyclo[2.2.2]oct-3-yl]-4-(5morpholin-4yl[1,3,4]thiadiazol-2-yloxy)-benzamide; N-[(2S,3R)-2-methyl-1-azabicyclo[2.2.2]oct-3-yl]-4-(4aminophenylsulfanyl) -benzamide; N-[(2S,3R)-2-methyl-1-azabicyclo[2.2.2]oct-3-yl]-4-(3-aminophenylsulfanyl)-benzamide; N-[(2S,3R)-2-methyl-1-azabicyclo[2.2.2]oct-3-yl]-4-(2-aminophenylsulfanyl)-benzamide; N-[(2S,3R)-2-methyl-1-azabicyclo[2.2.2]oct -3-yl]-4-(4methanesulfonyl-amino-phenylsulfanyl)-benzamide; N-[(2S,3R)-2-methyl -1-azabicyclo[2.2.2]oct-3-yl]-4-(3methanesulfonyl-amino-phenylsulfanyl)-benzamide; N-[(2S,3R)-2-methyl-1-azabicyclo[2.2.2]oct-3-yl]-4-(2methanesulfonyl-amino -phenylsulfanyl)-benzamide; N-[(2S,3R)-2-methyl-1-azabicyclo[2.2.2]oct-3-yl]-4-(4-acetoxy-phenylsulfanyl)-benzamide; N-[(2S,3R)-2-methyl-1-azabicyclo[2.2.2]oct-3-yl]-4-(3acetoxy-phenylsulfanyl)-benzamide; N-[(2S,3R)-2-methyl-1-azabicyclo[2.2.2]oct-3-yl]-4-(2-acetoxy-phenylsulfanyl)-benzamide; N-[(2S,3R)-2-methyl-1-azabicyclo[2.2.2]oct-3-yl]-4-(4acetyl-phenylsulfanyl)-benzamide; N -[(2S,3R)-2-methyl-1-azabicyclo[2.2.2]oct-3-yl]-4-(3acetyl-phenylsulfanyl) -benzamide; N-[(2S,3R)-2-methyl-1-azabicyclo[2.2.2]oct-3-yl]-4-(2-acetyl-phenylsulfanyl)-benzamide; N-[(2S,3R)-2-methyl-1-azabicyclo[2.2.2]oct-3-yl]-4-(4carbamoylphenylsulfanyl)-benzamide; N-[(2S,3R)-2-methyl-1-azabicyclo[2.2.2]oct-3-yl]-4-(3carbamoylphenylsulfanyl)-benzamide; N-[(2S,3R)-2-methyl-1-azabicyclo[2.2.2]oct-3-yl]-4-(2carbamoylphenylsulfanyl)-benzamide; N -[(2S,3R)-2-methyl-1-azabicyclo[2.2.2]oct-3-yl]-4-(4cyanophenylsulfanyl) -benzamide; N-[(2S,3R)-2-methyl-1-azabicyclo[2.2.2]oct-3-yl]-4-(3-cyanophenylsulfanyl)-benzamide; N-[(2S,3R)-2-methyl-1-azabicyclo[2.2.2]oct-3-yl]-4-(2-cyanophenylsulfanyl)-benzamide; N-[(2S,3R)-2-methyl-1-azabicyclo[2.2.2]oct -3-yl]-4-(4sulfamoylphenylsulfanyl)-benzamide; N-[(2S,3R)-2-methyl-1-azabicyclo[2.2.2]oct-3-yl]-4-(3sulfamoylphenylsulfanyl)-benzamide; N-[(2S,3R)-2-methyl-1-azabicyclo[2.2.2]oct-3-yl]-4-(2sulfamoyl-phenylsulfanyl)-benzamide; N -[(2S,3R)-2-methyl-1-azabicyclo[2.2.2]oct-3-yl]-4-(4-hydroxyphenylsulfanyl) -benzamide; N-[(2S,3R)-2-methyl-1-azabicyclo[2.2.2]oct-3-yl]-4-(3-hydroxyphenylsulfanyl)-benzamide; N-[(2S,3R)-2-methyl-1-azabicyclo[2.2.2]oct-3-yl]-4-(2-hydroxyphenylsulfanyl)-benzamide; N-[(2S,3R)-2-methyl-1-azabicyclo[2.2.2]oct-3-yl]-4-(4-acetamidophenylsulfanyl)-benzamide; N-[(2S,3R)-2-methyl-1-azabicyclo[2.2.2]oct-3-yl]-4-(3-acetamidophenylsulfanyl)-benzamide; N -[(2S,3R)-2-methyl-1-azabicyclo[2.2.2]oct-3-yl]-4-(2--acetamidophenylsulfanyl) -benzamide; N-[(2S,3R)-2-methyl-1-azabicyclo[2.2.2]oct-3-yl]-4-(thiophen-2-ylsulfanyl)-benzamide; N-[(2S,3R)-2-methyl-1-azabicyclo[2.2.2]oct-3-yl]-4-(5-methy-thiophen-2-ylsulfanyl)-benzamide; N-[(2S,3R)-2-methyl-1-azabicyclo[2.2.2]oct-3-yl]-4-(5chlorothiophen-2-ylsulfanyl)-benzamide; N-[(2S,3R) -2-methyl-1-azabicyclo[2.2.2]oct-3-yl]-4-(5methoxythiophen-2-ylsulfanyl) -benzamide; N-[(2S,3R)-2-methyl-1-azabicyclo[2.2.2]oct-3-yl]-4-(5-trifluoromethy-thiophen-2-ylsulfanyl)-benzamide; N-[(2S,3R)-2-methyl-1-azabicyclo[2.2.2]oct-3-yl]-4-(5acety-thiophen-2-ylsulfanyl)-benzamide; N-[(2S,3R) -2-methyl-1-azabicyclo[2.2.2]oct-3-yl]-4-(5acetaminothiophen-2-ylsulfanyl) -benzamide; N-[(2S,3R)-2-methyl-1-azabicyclo[2.2.2]oct-3-yl]-4-(5cyanothiophen-2-ylsulfanyl)-benzamide; N-[(2S,3R)-2-methyl-1-azabicyclo[2.2.2]oct-3-yl]-4-(5-morpholin-4y-thiophen-2-ylsulfanyl)-benzamide; N-[(2S,3R)-2-methyl-1-azabicyclo[2.2.2]oct-3-yl]-4-(4methy-thiophen-2-ylsulfanyl)-benzamide; N -[(2S,3R)-2-methyl-1-azabicyclo[2.2.2]oct-3-yl]-4-(4chlorothiophen-2-ylsulfanyl) -benzamide; N-[(2S,3R)-2-methyl-1-azabicyclo[2.2.2]oct-3-yl]-4-(4-methoxythiophen-2-ylsulfanyl)-benzamide; N-[(2S,3R)-2-methyl-1-azabicyclo[2.2.2]oct-3-yl]-4-(4trifluoromethy-thiophen-2-ylsulfanyl)-benzamide; N -[(2S,3R)-2-methyl-1-azabicyclo[2.2.2]oct-3-yl]-4-(4acety-thiophen-2-ylsulfanyl) -benzamide; N-[(2S,3R)-2-methyl-1-azabicyclo[2.2.2]oct-3-yl]-4-(4-acetaminothiophen-2-ylsulfanyl)-benzamide; N-[(2S,3R)-2-methyl-1-azabicyclo[2.2.2]oct-3-yl]-4-(4cyanothiophen-2-ylsulfanyl)-benzamide; N-[(2S,3R) -2-methyl-1-azabicyclo[2.2.2]oct-3-yl]-4-(4morpholin-4y-thiophen-2-ylsulfanyl) -benzamide; N-[(2S,3R)-2-methyl-1-azabicyclo[2.2.2]oct-3-yl]-4-(furan-2-ylsulfanyl) -benzamide; N-[(2S,3R)-2-methyl-1-azabicyclo[2.2.2]oct-3-yl]-4-(5methylfuran-2-ylsulfanyl)-benzamide; N-[(2S,3R)-2-methyl-1-azabicyclo[2.2.2]oct-3-yl]-4-(5-chlorofuran-2-ylsulfanyl)-benzamide; N-[(2S,3R)-2-methyl-1-azabicyclo[2.2.2]oct-3-yl]-4-(5methoxyfuran-2-ylsulfanyl)-benzamide; N-[(2S,3R)-2-methyl-1-azabicyclo[2.2.2]oct-3-yl]-4-(5trifluoromethylfuran-2-ylsulfanyl)-benzamide; N -[(2S,3R)-2-methyl-1-azabicyclo[2.2.2]oct-3-yl]-4-(5acetylfuran-2-ylsulfanyl) -benzamide; N-[(2S,3R)-2-methyl-1-azabicyclo[2.2.2]oct-3-yl]-4-(5acetaminofuran -2-ylsulfanyl)-benzamide; N-[(2S,3R)-2-methyl-1-azabicyclo[2.2.2]oct-3-yl]-4-(5-cyanofuran-2-ylsulfanyl)-benzamide; N-[(2S,3R)-2-methyl-1-azabicyclo -[2.2.2]oct-3-yl]-4-(5morpholin-4ylfuran-2-ylsulfanyl)-benzamide; N-[(2S,3R)-2-methyl-1-azabicyclo[2.2.2]oct-3-yl]-4-(4methylfuran-2-ylsulfanyl)-benzamide; N-[(2S,3R)-2-methyl-1-azabicyclo[2.2.2]oct-3-yl]-4-(4chlorofuran-2-ylsulfanyl)-benzamide; N -[(2S,3R)-2-methyl-1-azabicyclo

[2.2.2]oct-3-yl]-4-(4methoxyfuran-2-ylsulfanyl) -benzamide; N-[(2S,3R)-2-methyl-1-azabicyclo[2.2.2]oct-3-yl]-4-(4-trifluoromethylfuran-2-ylsulfanyl)-benzamide; N-[(2S,3R)-2-methyl-1-azabicyclo[2.2.2]oct-3-yl]-4-(4acetylfuran-2-ylsulfanyl)-benzamide; N-[(2S,3R)-2-methyl-1-azabicyclo[2.2.2]oct-3-yl]-4-(4acetaminofuran-2-ylsulfanyl)-benzamide; N-[(2S,3R)-2-methyl-1-azabicyclo [2.2.2]oct-3-yl]-4-(4cyanofuran-2-ylsulfanyl) -benzamide; N-[(2S,3R)-2-methyl-1-azabicyclo[2.2.2]oct-3-yl]-4-(4morpholin-4yl -furan-2-ylsulfanyl)-benzamide; N-[(2S, 3R)-2-methyl-1-azabicyclo[2.2.2]oct-3-yl]-4-(oxazol-2-ylsulfanyl)-benzamide; N-[(2S,3R)-2-methyl-1-azabicyclo [2.2.2]oct-3-yl]-4-(5methyloxazol-2-ylsulfanyl)-benzamide; N-[(2S,3R)-2-methyl-1-azabicyclo[2.2.2]oct-3-yl]-4-(5chlorooxazol-2-ylsulfanyl)-benzamide; N-[(2S,3R)-2-methyl-1-azabicyclo[2.2.2]oct-3-yl]-4-(5methoxyoxazol-2-ylsulfanyl)-benzamide; N-[(2S,3R)-2-methyl-1-azabicyclo[2.2.2]oct-3-yl]-4-(5trifluoromethyloxazol-2-ylsulfanyl)-benzamide; N-[(2S,3R)-2-methyl-1-azabicyclo[2.2.2]oct-3-yl]-4-(5-acetyloxazol-2-ylsulfanyl)-benzamide; N-[(2S,3R)-2-methyl-1-azabicyclo[2.2.2]oct -3-yl]-4-(5acetaminooxazol-2-ylsulfanyl)-benzamide; N-[(2S,3R)-2-methyl-1-azabicyclo[2.2.2]oct-3-yl]-4-(5cyanooxazol-2-ylsulfanyl)-benzamide; N-[(2S,3R)-2-methyl-1-azabicyclo [2.2.2]oct-3-yl]-4-(5morpholin-4yloxazol-2-ylsulfanyl) -benzamide; N-[(2S,3R)-2-methyl-1-azabicyclo[2.2.2]oct-3-yl]-4-(oxazol-2-ylsulfanyl)-benzamide; N-[(2S,3R)-2-methyl-1-azabicyclo[2.2.2]oct-3-yl]-4-(4-methyloxazol-2-ylsulfanyl)-benzamide; N-[(2S,3R)-2-methyl-1-azabicyclo [2.2.2]oct -3-yl]-4-(4chlorooxazol-2-ylsulfanyl)-benzamide; N-[(2S,3R)-2-methyl-1-azabicyclo[2.2.2]oct-3-yl]-4-(4methoxyoxazol-2-ylsulfanyl)-benzamide; N-[(2S, 3R) -2-methyl-1-azabicyclo[2.2.2]oct-3-yl]-4-(4trifluoromethyloxazol-2-ylsulfanyl) -benzamide; N-[(2S, 3R)-2-methyl-1-azabicyclo[2.2.2]oct-3-yl]-4-(4acetyloxazol-2-ylsulfanyl)-benzamide; N-[(2S,3R)-2-methyl-1-azabicyclo[2.2.2]oct-3-yl]-4-(4-acetaminooxazol-2-ylsulfanyl)-benzamide; N-[(2S,3R)-2-methyl-1-azabicyclo[2.2.2]oct-3-yl]-4-(4cyanooxazol-2-ylsulfanyl)-benzamide; N-[(2S,3R)-2-methyl-1-azabicyclo[2.2.2]oct-3-yl]-4-(4morpholin-4yloxazol-2-ylsulfanyl) -benzamide; N-[(2S,3R)-2-methyl-1-azabicyclo[2.2.2]oct-3-yl]-4-(oxazol-5-sulfanyl)-benzaide; N-[(2S,3R)-2-methyl-1-azabicyclo[2.2.2]oct-3-yl]-4-(2-methyloxazol-5-ylsulfanyl)-benzamide; N-[(2S,3R)-2-methyl-1-azabicyclo [2.2.2]oct -3-yl]-4-(2-chlorooxazol-5-ylsulfanyl)-benzamide; N-[(2S,3R)-2-methyl-1-azabicyclo[2.2.2]oct-3-yl]-4-(2-methoxyoxazol-5-ylsulfanyl)-benzamide; N-[(2S, 3R) -2-methyl-1-azabicyclo[2.2.2]oct-3-yl]-4-(2-trifluoromethyloxazol-5-ylsulfanyl) -benzamide; N-[(2S, 3R)-2-methyl-1-azabicyclo[2.2.2]oct-3-yl]-4-(2-acetyloxazol-5-ylsulfanyl)-benzamide; N-[(2S,3R)-2-methyl-1-azabicyclo[2.2.2]oct-3-yl]-4-(2-acetaminooxazol-5-ylsulfanyl)-benzamide; N-[(2S,3R)-2-methyl-1-azabicyclo[2.2.2]oct-3-yl]-4-(2-cyanooxazol-5-ylsulfanyl)-benzamide; N-[(2S,3R)-2-methyl-1-azabicyclo[2.2.2]oct-3-yl]-4-(2-morpholin-4yloxazol-5-ylsulfanyl) -benzamide; N-[(2S,3R)-2-methyl-1-azabicyclo[2.2.2]oct-3-yl]-4-(thiazol-2-ylsulfanyl)-benzamide; N-[(2S,3R)-2-methyl-1-azabicyclo[2.2.2]oct-3-yl]-4-(5-methylthiazol-2-ylsulfanyl)-benzamide; N-[(2S,3R)-2-methyl-1-azabicyclo [2.2.2]oct -3-yl]-4-(5chlorothiazol-2-ylsulfanyl)-benzamide; N-[(2S,3R)-2-methyl-1-azabicyclo[2.2.2]oct-3-yl]-4-(5methoxythiazol-2-ylsulfanyl)-benzamide; N -[(2S, 3R)-2-methyl-1-azabicyclo[2.2.2]oct-3-yl]-4-(5trifluoromethylthiazol-2-ylsulfanyl)-benzamide; N-[(2S, 3R)-2-methyl-1-azabicyclo[2.2.2]oct-3-yl]-4-(5-acetylthiazol-2-ylsulfanyl)-benzamide; N-[(2S,3R)-2-methyl-1-azabicyclo[2.2.2]oct -3-yl]-4-(5acetaminothiazol-2-ylsulfanyl)-benzamide; N-[(2S,3R)-2-methyl-1-azabicyclo[2.2.2]oct-3-yl]-4-(5cyanothiazol-2-ylsulfanyl)-benzamide; N-[(2S,3R)-2-methyl-1-azabicyclo[2.2.2]oct-3-yl]-4-(5morpholin-4ylthiazol-2-ylsulfanyl) -benzamide; N-[(2S,3R)-2-methyl-1-azabicyclo[2.2.2]oct-3-yl]-4-(thiazol-2-ylsulfanyl)-benzamide; N-[(2S,3R)-2-methyl-1-azabicyclo[2.2.2]oct-3-yl]-4-(4-methylthiazol-2-ylsulfanyl)-benzamide; N-[(2S,3R)-2-methyl-1-azabicyclo [2.2.2]oct -3-yl]-4-(4chlorothiazol-2-ylsulfanyl)-benzamide; N-[(2S,3R)-2-methyl-1-azabicyclo[2.2.2]oct-3-yl]-4-(4methoxythiazol-2-ylsulfanyl)-benzamide; N -[(2S, 3R)-2-methyl-1-azabicyclo[2.2.2]oct-3-yl]-4-(4trifluoromethylthiazol-2-ylsulfanyl)-benzamide; N-[(2S, 3R)-2-methyl-1-azabicyclo[2.2.2]oct-3-yl]-4-(4-acetylthiazol-2-ylsulfanyl)-benzamide; N-[(2S,3R)-2-methyl-1-azabicyclo[2.2.2]oct -3-yl]-4-(4acetaminothiazol-2-ylsulfanyl)-benzamide; N— -[(2S,3R)-2-methyl-1-azabicyclo[2.2.2]oct-3-yl]-4-(4cyanothiazol-2-ylsulfanyl)-benzamide; N-[(2S,3R)-2-methyl-1-azabicyclo[2.2.2]oct-3-yl]-4-(4morpholin-4ylthiazol-2-ylsulfanyl) -benzamide; N-[(2S,3R)-2-methyl-1-azabicyclo[2.2.2]oct-3-yl]-4-(thiazol-5-ylsulfanyl)-benzamide; N-[(2S,3R)-2-methyl-1-azabicyclo[2.2.2]oct-3-yl]-4-(2-methylthiazol-5-ylsulfanyl)-benzamide; N-[(2S,3R)-2-methyl-1-azabicyclo [2.2.2]oct -3-yl]-4-(2-chlorothiazol-5-ylsulfanyl)-benzamide; N-[(2S,3R)-2-methyl-1-azabicyclo[2.2.2]oct-3-yl]-4-(2-methoxythiazol-5-ylsulfanyl)-benzamide; N -[(2S, 3R)-2-methyl-1-azabicyclo[2.2.2]oct-3-yl]-4-(2-trifluoromethylthiazol-5-ylsulfanyl)-benzamide; N-[(2S,3R) -2-methyl-1-azabicyclo[2.2.2]oct-3-yl]-4-(2-acetylthiazol-5-ylsulfanyl)-benzan-iide; N-[(2S,3R)-2-methyl-1-azabicyclo[2.2.2]oct -3-yl]-4-(2-acetaminothiazol-5-ylsulfanyl)-benzamide; N-[(2S,3R)-2-methyl-1-azabicyclo [2.2.2]oct-3-yl]-4-(2-cyanothiazol-5-ylsulfanyl)-benzamide; N-[(2S,3R)-2-methyl-1-azabicyclo[2.2.2]oct-3-yl]-4-(2-morpholin-4yl-thiazol-5ylsulfany-1) -benzamide; N-[(2S,3R)-2-methyl-1 1-azabicyclo[2.2.2]oct-3-yl]-4-([1,3, 4]oxadiazol-2-ylsulfanyl)-benzamide; N-[(2S,3R)-2-methyl-1-azabicyclo[2.2.2]oct-3-yl]-4-(5-methyl[1,3,4] oxadiazol-2-ylsulfanyl)-benzamide; N-[(2S,3R)-2-methyl-1-azabicyclo[2.2.2]oct-3y-1]-4-(5chloro-[1,3,4]oxadiazol-2-ylsulfanyl)-benzamide; N -[(2S,3R)-2-methyl-1-azabicyclo[2.2.2]oct-3-yl]-4-(5methoxy-[1,3,4]oxadiazol-2-ylsulfanyl)-benzamide; N-[(2S,3R) -2-methyl-1-azabicyclo [2.2.2]oct-3-yl]-4-(5-trifluoromethyl[1,3,4]oxadiazol-2-ylsulfanyl)-benzamide; N-[(2S,3R)-2-methyl -azabicyclo [2.2.2]oct-3-yl]-4-(5acetyl[1,3,4]oxadiazol-2-ylsulfanyl)-benzamide; N -[(2S,3R)-2-methyl-1-azabicyclo[2.2.2]oct-3-yl]-4-(5acetamino[1,3,4]oxadiazol-2-ylsulfanyl)-benzamide; N-[(2S,3R)-2-methyl-1-azabicyclo[2.2.2]oct-3-yl]-4-(5-cyano-[1,3,4]oxadiazol-2-ylsulfanyl)-benzamide; N-[(2S,3R)-2-methyl-1-azabicyclo[2.2.2]oct-3-yl]-4-(5morpholin-4yl[1,3,4]oxadiazol -2-ylsulfanyl) -benzamide; N-[(2S,3R)-2-methyl-1-azabicyclo[2.2.2]oct-3-yl]-4-([1,3, 4]thiadiazol-2-ylsulfanyl)-benzamide; N-[(2S,3R)-2-methyl-1-azabicyclo[2.2.2]oct-3-yl]-4-(5-methyl[1,3,4] thiadiazol-2-ylsulfanyl)-benzamide; N-[(2S,3R)-2-methyl-1-azabicyclo[2.2.2]oct-3-yl]-4-(5chloro-[1,3,4]thiadiazol-2-ylsulfanyl)-benzamide; N -[(2S,3R)-2-methyl-1-azabicyclo [2.2.2]oct-3-yl]-4-(5methoxy-[1,3,4]thiadiazol-2-ylsulfanyl)-benzamide; N-[(2S,3R)-2-methyl-1-azabicyclo [2.2.2]oct-3-yl]-4-(5-trifluoromethyl 1,3,4]thiadiazol-2-ylsulfanyl)-benzamide; N-[(2S,3R)-2-methyl-1-azabicyclo [2.2.2]oct-3-yl]-4-(5acetyl -[1,3,4]thiadiazol-2-ylsulfanyl)-benzamide; N -[(2S,3R)-2-methyl-1-azabicyclo[2.2.2]oct-3- yl]-4-(5acetamino[1,3,4]thiadiazol-2-ylsulfanyl)-benzamide; N-[(2S,3R)-2-methyl-1-azabicyclo[2.2.2]oct-3-yl]-4-(5-cyano-[1,3,4]thiadiazol-2-ylsulfanyl)-benzamide; N-[(2S,3R)-2-methyl-1-azabicyclo[2.2.2]oct-3-yl]-4-(5morpholin-4yl[1,3,4]thiadiazol-2-ylsulfanyl) -benzamide; N:-(2S,3R)-2-methyl-1-azabicyclo[2.2.2]oct-3-yl]-4-(pyrrol-2-yloxy) -benzamide; N-[(2S,3R)-2-methyl-1-azabicyclo[2.2.2]oct-3-yl]-4-(5methylpyrrol rro-2-yloxy)-benzamide; N-[(2S,3R)-2-methyl-1-azabicycio-[2.2.2]oct-3-yl]-4-(5-chloropyrrol-2-yloxy)-benzamide; N-[(2S,3R)-2-methyl-1-azabicyclo[2.2.2]oct-3yi]-4-(5methoxypyrrol-2-yloxy)-benzamide; N-[(2S,3R)-2-methyl-1-benzamide; N-[(2S,3R)-2-methyl-1-azabicyclo[2.2.2]oct-3-yl-4-(5-ceylpyrrol-2-yloxy -2-yloxy)-benzamide; N-[(2S,3R)-2-methyl-1-azabicyclo[2.2.2]oct-3-yl]-4-(5-cyanopyrrol-2-yloxy)-benzamide; N-[(2S,3R)-2-methyl-1-azabicyclo[2.2.2]oct-3-yl]4-(⁵-morphoiin-4ylpyrroi-2yloxy)-benzamide; N-[(2S,3R)-2-methyl -1-methyl-1-azabicyclo-[2.2.2]oct-3-yl]-4-(i-2-methyl-3H-ia-yloxy)-benzamide; N N-[(2S,3R)-2-methyl-1-azabicyclo -[2.2.2]oct-3-yl]-4-(2-chloro-3l-im idazol -4yloxy) -benzamide; N-[(2S,3R)-2-methyl-1-azabicyclo[2.2.2]oct-3-yl]-4-(2-methoxy-3H -2 imdazol-4yloxy)-benzamide; N-[(2S,3R)-2-methyl-1-azabicyclo[2.2.2]oct-3-yl]-4-(2-trifluoromethyl-3H-imidazol-4yloxy)-benzamide; N-[(2S,3R)-2-methyl-1-azabicyclo[2.2.2]oct-3-yl]-4-(3imidazol-4yloxy) -benzamide; N-[(2S,3R) -2-methyl-1-azabicyclo -[2.2.2]oct-3-yl]-4-(2-methyl-3H-imidazol-4yloxy) -benzamide; N-[(2S,3R)-2-methyl-1-azabicyclo[2.2.2]oct-3-yl]-4-(2-cyano-3H -imidazol-4yloxy)-benzamide; N-[(2S,3R)-2-methyl-1-azabicyclo[2.2.2]oct-3-yl]-4-(2-morpholin-4yl-3H-imidazol-4yloxy)-benzamide; N-[(2S,3R)-2-methyl-1-azabicyclo[2.2.2]oct-3-yl]-4-(isoxazol-2-yloxy)-benzamide; N-[(2S,3R)-2-methyl-1-azabicyclo[2.2.2]oct-3-yl]-4-(5methylisoxazol-3-yloxy)-benzamide; N-[(2S,3R)-2-methyl-1-azabicyclo[2.2.2]oct-3-yl]-4-(5chloroisoxazol-3-yloxy)-benzamide; N -[(2S,3R)-2-methyl-1-azabicyclo [2.2.2]oct-3-yl]-4-(5methoxyisoxazol-3-yloxy) -benzamide; N-[(2S,3R)-2-methyl-1-azabicyclo[2.2.2]oct-3-yl]-4-(5-trifluoromethylisoxazol-3-yloxy)-benzamide; N-[(2S,3R)-2-methyl-1-azabicyclo[2.2.2]oct-3-yl]-4-(5acetylisoxazol-3-yloxy)-benzamide; N-[(2S,3R)-2-methyl-1-azabicyclo [2.2.2]oct-3-yl]-4-(5-acetaminoisoxazol-3-yloxy)-benzamide; N -[(2S,3R)-2-methyl-1-azabicyclo[2.2.2]oct-3-yl]-4-(5cyanoisoxazol-3-yloxy) -benzamide; N-[(2S,3R)-2-methyl-1-azabicyclo[2.2.2]oct-3-yl]-4-(5morpholin-4yl -isoxazol-3-yloxy)-benzamide; N-[(2S.,3R)-2-methyl-1-azabicyclo -[2.2.2]oct-3-yl]-4-(isothiazol-2-yloxy)-benzamide; N-[(2S,3R)-2-methyl-1-azabicyclo[2.2.2]oct-3-yl]-4-(5-methylisothiazol-3-yloxy)-benzamide; N-[(2S,3R)-2-methyl-1-azabicyclo[2.2.2]oct-3-yl]-4-(5chloroisothiazol-3-yloxy)-benzamide; N-[(2S,3R)-2-methyl-1-azabicyclo[2.2.2]oct-3-yl]-4-(5-methoxyisothiazol -3-yloxy)-benzamide; N -[(2S,3R)-2-methyl-1-azabicyclo[2.2.2]oct-3-yl]-4-(5trifluoromethyl-isothiazol-3-yloxy)-benzamide; N-[(2S,3R)-2-methyl-1-azabicyclo[2.2.2]oct-3-yl]-4-(5-acetyl-isothiazol-3-yloxy)-benzamide; N-[(2S,3R)-2-methyl-1-azabicyclo[2.2.2]oct-3-yl]-4-(5acetaminoisothiazol-3-yloxy)-benzamide; N-[(2S,3R)-2-methyl-1-azabicyclo[2.2.2]oct-3-yl]-4-(5cyanoisothiazol-3-yloxy)-benzamide; N-[(2S,3R)-2-methyl-1-azabicyclo[2.2.2]oct-3-yl]-4-(5morpholin-4yl-isothiazol-3-yloxy) -benzamide; N-[(2S,3R)-2-methyl-1-azabicyclo[2.2.2]oct-3-yl]-4-(pyrrol-2-ylsulfanyl)-benzamide; N-[(2S,3R)-2-methyl-1-azabicyclo[2.2.2]oct-3-yl]-4-(5-methylpyrrolrrol-2-ylsulfanyl)-benzamide; N-[(2S,3R)-2-methyl-1-azabicyclo[2.2.2]oct -3-yl]-4-(5chloropyrrol-2-ylsulfanyl)-benzamide; N-[(2S,3R)-2-methyl-1-azabicyclo[2.2.2]oct-3-yl]-4-(5methoxypyrrol-2-ylsulfanyl)-benzamide; N-[(2S,3R) -2-methyl-1-azabicyclo[2.2.2]oct-3-yl]-4-(5trifluoromethylpyrrolrrol-2-ylsulfanyl) -benzamide; N-[(2S,3R)-2-methyl-1-azabicyclo[2.2.2]oct-3-yl]-4-(5acetylpyrrol-2-ylsulfanyl)-benzamide; N-[(2S,3R)-2-methyl-1-azabicyclo[2.2.2]oct-3-yl]-4-(5-acetaminopyrrol-2-ylsulfanyl)-benzamide; N-[(2S,3R)-2-methyl-1-azabicyclo[2.2.2]oct-3-yl]-4-(5cyanopyrrol-2-ylsulfanyl)-benzamide; N-[(2S,3R)-2-methyl-1-azabicyclo[2.2.2]oct-3-yl]-4-(5morpholin-4ylpyrrol-2-ylsulfanyl) -benzamide; N-[(2S,3R)-2-methyl-1-azabicyclo[2.2.2]oct-3-yl]-4-(3H-imidazol-4-ylsulfanyl)-benzamide; N-[(2S,3R)-2-methyl-1-azabicyclo[2.2.2]oct-3-yl]-4-(2-methyl-3 H-im-idazol-4-ylsulfanyl)-benzamide; N-[(2S,3R)-2-methyl-1-azabicyclo[2.2.2]oct-3-yl]-4-(2-chloro-3H-imidazol-4-ylsulfanyl)-benzamide; N -[(2S,3R)-2-methyl-1-azabicyclo[2.2.2]oct-3-yl]-4-(2-methoxy-3H-imidazol-4-ylsulfanyl)-benzamide; N-[(2S,3R)-2-methyl-1-azabicyclo[2.2.2]oct-3-yl]-4-(2-trifluoromethyl-3H-imidazol-4-ylsulfanyl)-benzamide; N-[(2S,3R)-2-methyl-1-azabicyclo[2.2.2]oct-3-yl]-4-(2-acetyl-3H-imidazol-4-ylsulfanyl)-benzamide; N -[(2S,3R)-2-methyl-1-azabicyclo[2.2.2]oct-3-yl]-4-(2-acetamino-3H-imidazol-4-ylsulfanyl)-benzamide; N-[(2S,3R)-2-methyl-1-azabicyclo[2.2.2]oct-3-yl]-4-(2-cyano-3H-imidazol-4-ylsulfanyl)-benzamide; N-[(2S,3R)-2-methyl-1-azabicyclo [2.2.2]oct-3-yl]-4-(2-morpholin-4yl-3H-imidazol-4-ylsulfanyl)-benzamide; N-[(2S,3R)-2-methyl-1-azabicyclo[2.2.2]oct-3-yl]-4-(isoxazol-2-ylsulfanyl) -benzamide; N-[(2S,3R)-2-methyl-1-azabicyclo[2.2.2]oct-3-yl]-4-(5methylisoxazol -3-ylsulfanyl)-benzamide; N-[(2S,3R)-2-methyl-1-azabicyclo[2.2.2]oct-3-yl]-4-(5-chloroisoxazol-3-ylsulfanyl)-benzamide; N-[(2S,3R)-2-methyl-1-azabicyclo [2.2.2]oct-3-yl]-4-(5methoxyisoxazol-3-ylsulfanyl)-benzamide; N -[(2S,3R)-2-methyl-1-azabicyclo[2.2.2]oct-3-yl]-4-(5trifluoromethylisoxazol-3-ylsulfanyl)-benzamide; N-[(2S,3R)-2-methyl-1-azabicyclo[2.2.2]oct-3-yl]-4-(5-acetylisoxazol-3-ylsulfanyl)-benzamide; N-[(2S,3R)-2-methyl-1-azabicyclo[2.2.2]oct-3-yl]-4-(5-acetaminoisoxazol-3-ylsulfanyl)-benzamide; N-[(2S,3R)-2-methyl-1-azabicyclo[2.2.2]oct-3-yl]-4-(5cyanoisoxazol-3-ylsulfanyl) -benzamide; N-[(2S,3R)-2-methyl-1-azabicyclo [2.2.2]oct-3-yl]-4-(5morpholin-4yl -isoxazol-3-ylsulfanyl)-benzamide; N-[(2S,3R)-2-methyl-1-azabicyclo[2.2.2]oct-3-yl]-4-(-isothiazol-2-ylsulfanyl)-benzamide; N-[(2S,3R)-2-methyl-1-azabicyclo[2.2.2]oct -3-yl]-4-(5-methylisothiazol-3-ylsulfanyl)-benzamide; N-[(2S,3R)-2-methyl-1-azabicyclo[2.2.2]oct-3-yl]-4-(5-chloroisothiazol-3-ylsulfanyl)-benzanide; N -[(2S,3R)-2-methyl-1-azabicyclo[2.2.2]oct-3-yl]-4-(5methoxy-isothiazol-3-ylsulfanyl) -benzamide; N-[(2S,3R)-2-methyl-1-azabicyclo[2.2.2]oct-3-yl]-4-(5-trifluoromethyl-isothiazol-3-ylsulfanyl)-benzamide; N-[(2S,3R)-2-methyl-1-azabicyclo[2.2.2]oct-3-yl]-4-(5-acetylisothiazol-3-ylsulfanyl)-benzamide; N -[(2S,3R)-2-methyl-1-azabicyclo[2.2.2]oct-3-yl]-4-(5acetaminoisothiazol-3-ylsulfanyl)-benzamide; N-[(2S,3R)-2-methyl-1-azabicyclo[2.2.2]oct-3-yl]-4-(5-cyano-isothiazol-3-ylsulfanyl)-benzamide; N-[(2S,3R)-2-methyl-1-azabicyclo[2.2.2]oct-3-yl]-4-(5morpholin-4yl-isothiazol-3-ylsulfanyl)-benzamide; N-[(2S,3R)-2-methyl-1-azabicyclo[2.2.2]oct-3-yl]-4-(6-methylpyrrolridin-3-yloxy) -benzamide; N-[(2S,3R)-2-methyl-1-azabicyclo[2.2.2]oct-3-yl]-4-(6-chloropyridin-3-yloxy)-benzamide; N-[(2S,3R)-2-methyl-1-azabicyclo[2.2.2]oct-3-yl]-4-(6-methoxypyridin-3-yloxy)-benzamide; N-[(2S,3R)-2-methyl-1-azabicyclo[2.2.2]oct-3-yl]-4-(6-trifluoromethylpyrrolridin-3-yloxy)-benzamide; N-[(2S, 3R)-2-methyl-1-azabicyclo[2.2.2]oct-3-yl]-4-(6-acetylpyridin-3-yloxy)-benzamide; N-[(2S,3R)-2-methyl-1-azabicyclo[2.2.2]oct-3-yl]-4-(6-acetaminopyridin-3-yloxy)-benzamide; N -[(2S,3R)-2-methyl-1-azabicyclo[2.2.2]oct-3-yl]-4-(6-cyanopyridin-3-yloxy) -benzamide; N-[(2S,3R)-2-methyl-1-azabicyclo[2.2.2]oct-3-yl]-4-(6-morpholin-4yl -pyridin-3yoxy)benzamide; N-[(2S,3R)-2-methyl-1-azabicyco-[2.2.2]oct-3-yl]-4-(2-methylpyrrolridin-4yloxy)-benzamide; N-[(2S,3R)-2-methyl-1-azabicyclo[2.2.2]oct-3-yl]-4-(2-chloropyridin-4yloxy)-benzamide; N-[(2S,3R)-2-methyl-1-azabicyclo[2.2.2]oct-3-yl]-4-(2-methoxypyridin-4yloxy)-benzamide; N-[(2S,3R)-2-methyl-1-azabicyclo[2.2.2]oct-3-yl]-4-(2-trifluoromethylpyrrolridin-4yloxy)-benzamide; N-[(2S,3R)-2-methyl-1-azabicyclo[2.2.2]oct-3-yl]-4-(2-acetylpyridin-4yloxy) -benzamide; N-[(2S,3R)-2-methyl-1-azabicyclo[2.2.2]oct-3-yl]-4-(2-acetaminopyridin-4yloxy)-benzamide; N-[(2S,3R)-2-methyl-1-azabicyclo[2.2.2]oct -3-yl]-4-(2-cyanopyridin-4yloxy)-benzamide; N-[(2S,3R)-2-methyl-1-azabicyclo[2.2.2]oct-3-yl]-4-(2-morpholin-4ylpyridin-4yloxy)-benzamide; N -[(2S,3R)-2-methyl-1-azabicyclo[2.2.2]oct-3-yl]-4-(5methylpyrrolridin-2-yloxy) -benzamide; N-[(2S,3R)-2-methyl-1-azabicyclo[2.2.2]oct-3-yl]-4-(5chloropyridin-2-yloxy)-benzamide; N-[(2S,3R)-2-methyl-1-azabicyclo[2.2.2]oct-3-yl]-4-(5-methoxypyridin-2-yloxy)-benzamide; N-[(2S,3R)-2-methyl-1-azabicyclo[2.2.2]oct-3-yl]-4-(5trifluoromethylpyrrolridin-2-yloxy)-benzamide; N-[(2S,3R)-2-methyl-1-azabicyclo[2.2.2]oct-3-yl]-4-(5-acetylpyridin-2-yloxy)-benzamide; N-[(2S,3R)-2-methyl-1-azabicyclo[2.2.2]oct-3-yl]-4-(5acetamnino-pyridin-2-yloxy)-benzamide; N -[(2S,3R)-2-methyl-1-azabicyclo[2.2.2]oct-3-yl]-4-(5cyanopyridin-2-yloxy) -benzamide; N-[(2S,3R)-2-methyl-1-azabicyclo[2.2.2]oct-3-yl]-4-(5morpholin-4yl -pyridin-2-yloxy)-benzamide; N-[(2S,3R)-2-methyl-1-azabicyclo[2.2.2]oct-3-yl]-4-(4-methylpyrrolridin-2-yloxy)-benzamide; N-[(2S,3R)-2-methyl-1-azabicyclo[2.2.2]oct-3-yl]-4-(4chloropyridin-2-yloxy)-benzamide; N-[(2S,3R)-2-methyl-1-azabicyclo[2.2.2]oct-3-yl]-4-(4methoxypyridin-2-yloxy)-benzamide; N-[(2S,3R)-2-methyl-1-azabicyclo[2.2.2]oct-3-yl]-4-(4trifluoromethylpyrrolridin-2-yloxy)benzamide; N-[(2S,3R)-2-methyl-1-azabicyclo[2.2.2]oct-3-yl]-4-(4-acetylpyridin-2-yloxy) -benzamide; N-[(2S,3R)-2-methyl-1-azabicyclo[2.2.2]oct-3-yl]-4-(4-acetaminopyridin-2-yloxy)-benzamide; N-[(2S,3R)-2-methyl-1-azabicyclo[2.2.2]oct -3-yl-4-(4cyanopyridin-2-yloxy)-benzamide; N-[(2S,3R)-2-methyl-1-azabicyclo[2.2.2]oct-3-yl]-4-(4morpholin-4ylpyridin-2-yloxy)-benzamide; N -[(2S,3R)-2-methyl-1-azabicyclo[2.2.2]oct-3-yl]-4-(6-methylpyrrolridin-2-yloxy) -benzamide; N-[(2S,3R)-2-methyl-1-azabicyclo[2.2.2]oct-3-yl]-4-(6-chloropyridin-2-yloxy)-benzamide; N-[(2S,3R)-2-methyl-1-azabicyclo[2.2.2]oct-3-yl]-4-(6-methoxypyridin-2-yloxy)-benzamide; N-[(2S,3R)-2-methyl-1-azabicyclo[2.2.2]oct-3-yl]-4-(6-trifluoromethylpyrrolridin-2-yloxy)-benzamide; N-[(2S,3R)-2-methyl-1-azabicyclo[2.2 .2oct-3-yl]-4-(6-acetylpyridin-2-yloxy)-benzamide; N-[(2S,3R)-2-methyl-1-azabicyclo[2.2.2]oct-3yI]-4-(6-acetaminopyridin-2-yloxy)-benzamide; N -[(2S,3R)-2-methyl -1-azabicyclo[2.2.2]oct-3-yl]-4-(6-c yano-pyridin-2-yloxy) -benzamide; N-[(2S,3R)-2-methyl-1-azabicyclo[2.2.2]oct-3-yl]-4-(6-morpholin-4yl -pyridin-2-yloxy)-benzamide; N-[(2S,3R)-2-methyl-1-azabicyclo[2.2.2]oct-3-yl]-4-(5-methylpyrrolridin-3-yloxy)-benzamide; N-[(2S,3R)-2-methyl-1-azabicyclo[2.2.2]oct-3-yl]-4-(5-chloropyridin-3-yloxy)-benzamide; N-[(2S,3R)-2-methyl-1-azabicyclo[2.2.2]oct-3-yl]-4-(5methoxypyridin-3-yloxy)-benzamide; N-[(2S,3R)-2-methyl-1-azabicyclo[2.2.2]oct-3-yl]-4-(5trifluoromethylpyrrolridin-3-yloxy)-benzamide; N-[(2S,3R)-2-methyl-1-azabicyclo[2.2.2]oct-3-yl]-4-(5-acetylpyridin-3-yloxy) -benzamide; N-[(2S,3R)-2-methyl I-azabicyclo[2.2.2]oct-3-yl]-4-(5-acetaminopyridin-3-yloxy)-benzamide; N-[(2S,3R)-2-methyl-1-azabicyclo[2.2.2]oct -3-yl]-4-(5cyanopyridin-3-yloxy)-benzamide; N-[(2S,3R)-2-methyl-1-azabicyclo[2.2.2]oct-3-yl]-4-(5morpholin-4ylpyridin-3-yloxy)-benzamide; N -[(2S,3R)-2-methyl-1-azabicyclo[2.2.2]oct-3-yl]-4-(2--chloropyridin-3-yloxy) -benzamide; N-[(2S,3R)-2-methyl-1-azabicyclo[2.2.2]oct-3-yl]-4-(4-chloropyridin-3-yloxy)-benzamide; N-[(2S,3R)-2-methyl-1-azabicyclo[2.2.2]oct-3-yl]-4-(3--chloropyridin-4yloxy)-benzamide; N-[(2S,3R)-2-methyl-1-azabicyclo[2.2.2]oct-3-yl]-4-(3-chloropyridin-2-yloxy)-benzamide; N-[(2S,3R)-2-methyl-1-azabicyclo[2.2.2]oct-3-yl]-4-(6-methylpyrrolridin-3-ylsulfanyl)-benzamide; N-[(2S,3R) -2-methyl-1-azabicyclo[2.2.2]oct-3-yl]-4-(6--chloropyridin-3-ylsulfanyl)-benzamide; N-[(2S,3R)-2-methyl-1-azabicyclo[2.2.2]oct-3-yl]-4-(6-methoxypyridin-3-ylsulfanyl) -benzamide; N-[(2S,3R)-2-methyl-1-azabicyclo[2.2.2]oct-3-yl]-4-(6-trifluoromethylpyrrolridin-3-ylsulfanyl)-benzamide; N-[(2S,3R)-2-methyl-1-azabicyclo[2.2.2]oct-3-yl]-4-(6-acetylpyridin-3-ylsulfanyl)-benzamide; N-[(2S,3R)-2-methyl-1-azabicyclo[2.2.2]oct-3-yl]-4-(6-acetanino-pyridin-3-ylsulfanyl)-benzamide; N-[(2S,3R)-2-methyl-1-azabicyclo[2.2.2]oct-3-yl]-4-(6-cyanopyridin-3-ylsulfanyl) -benzamide; N-[(2S,3R)-2-methyl-1-azabicyclo[2.2.2]oct-3-yl]-4-(6-morpholin-4yl -pyridin-3-ylsulfanyl)-benzamide; N-[(2S,3R)-2-methyl-1-azabicyclo[2.2.2]oct-3-yl]-4-(2-methylpyrrolridin-4-ylsulfanyl)-benzamide; N-[(2S,3R)-2-methyl-1-azabicyclo[2.2.2]oct-3-yl]-4-(2--chloropyridin-4-ylsulfanyl)-benzanide; N-[(2S,3R) -2-methyl-1-azabicyclo[2.2.2]oct-3-yl]-4-(2-methoxypyridin-4-ylsulfanyl)-benzamide; N-[(2S,3R)-2-methyl-1-azabicyclo[2.2.2]oct-3-yl]-4-(2-trifluoromethylpyrrolridin-4-ylsulfanyl)-benzamide; N-[(2S,3R)-2-methyl-1-azabicyclo[2.2.2]oct-3-yl]-4-(2-acetylpyridin-4-ylsulfanyl)-benzamide; N-[(2S,3R)-2-methyl-1-azabicyclo[2.2.2]oct -3-yl]-4-(2-acetaminopyridin-4-ylsulfanyl)-benzamide; N-[(2S,3R)-2-methyl-1-azabicyclo[2.2.2]oct-3-yl]-4-(2-cyanopyridin-4-ylsulfanyl)-benzamide; N-[(2S,3R)-2-methyl-1-azabicyclo[2.2.2]oct-3-yl]-4-(2-morpholin-4ylpyridin-4-ylsulfanyl) -benzamide; N-[(2S,3R)-2-methyl-1-azabicyclo[2.2.2]oct-3-yl]-4-(5methylpyrrolridin-2-ylsulfanyl)-benzamide; N-[(2S,3R)-2-methyl-1-azabicyclo[2.2.2]oct-3-yl]-4-(5--chloropyridin-2-ylsulfanyl)-benzamide; N-[(2S,3R)-2-methyl-1-azabicyclo[2.2.2]oct -3-yl]-4-(5methoxypyridin-2-ylsulfanyl)-benzamide; N-[(2S,3R)-2-methyl-1-azabicyclo[2.2.2]oct-3-yl]-4-(5trifluoromethylpyrrolridin-2-ylsulfanyl)-benzamide; N -[(2S,3R)-2-methyl-1-azabicyclo[2.2.2]oct-3-yl]-4-(5-acetylpyridin-2-ylsulfanyl) -benzamide; N-[(2S,3R)-2-methyl-1-azabicyclo[2.2.2]oct-3-yl]-4-(5-acetaminopyridin-2-ylsulfanyl)-benzamide; N-[(2S,3R)-2-methyl-1-azabicyclo[2.2.2]oct-3-yl]-4-(5cyanopyridin-2-ylsulfanyl)-benzamide; N-[(2S,3R)-2-methyl-1-azabicyclo[2.2.2]oct-3-yl]-4-(5morpholin-4ylpyridin-2-ylsulfanyl) -benzamide; N-[(2S,3R)-2-methyl-1-azabicyclo[2.2.2]oct-3-yl]-4-(4methylpyrrolridin-2-ylsulfanyl)-benzamide; N-[(2S,3R)-2-methyl-1-azabicyclo[2.2.2]oct-3-yl]-4-(4--chloropyridin-2-ylsulfanyl)-benzamide; N-[(2S,3R)-2-methyl-1-azabicyclo[2.2.2]oct -3-yl]-4-(4methoxypyridin-2-ylsulfanyl)-benzamide; N-[(2S,3R)-2-methyl-1-azabicyclo[2.2.2]oct-3-yl]-4-(4trifluoromethylpyrrolridin-2-ylsulfanyl)-benzamide; N -[(2S,3R)-2-methyl-1-azabicyclo[2.2.2]oct-3-yl]-4-(4-acetylpyridin-2-ylsulfanyl) -benzamide; N-[(2S,3R)-2- methyl-1-azabicyclo[2.2.2]oct-3-yl]-4-(4-acetaminopyridin-2-ylsulfanyl)-benzamide; N-[(2S,3R)-2-methyl-1-azabicyclo[2.2.2]oct-3-yl]-4-(4cyanopyridin-2-ylsulfanyl)-benzamide; N-[(2S,3R)-2-methyl-1-azabicyclo[2.2.2]oct-3-yl]-4-(4morpholin-4ylpyridin-2-ylsulfanyl)-benzamide; N-[(2S,3R)-2-methyl-1-azabicyclo[2.2.2]oct-3-yl]-4-(6-methylpyrrolridin-2-ylsulfanyl)-benzamide; N-[(2S,3R)-2-methyl-1-azabicyclo[2.2.2]oct-3-yl]-4-(6--chloropyridin-2-ylsulfanyl)-benzamide; N-[(2S,3R)-2-methyl-1-azabicyclo[2.2.2]oct -3-yl]-4-(6-methoxypyridin-2-ylsulfanyl)-benzamide; N-[(2S,3R)-2-methyl-1-azabicyclo[2.2.2]oct-3-yl]-4-(6-trifluoromethylpyrrolridin-2-ylsulfanyl)-benzamide; N -[(2S,3R)-2-methyl-1-azabicyclo[2.2.2]oct-3-yl]-4-(6-acetylpyridin-2-ylsulfanyl)-benzamide; N-[(2S,3R)-2-methyl-1-azabicyclo[2.2.2]oct-3-yl]-4-(6-acetaminopyridin-2-ylsulfanyl)-benzamide; N-[(2S,3R)-2-methyl-1-azabicyclo[2.2.2]oct-3-yl]-4-(6-cyanopyridin-2-ylsulfanyl)-benzamide; N-[(2S,3R)-2-methyl-1-azabicyclo[2.2.2]oct-3-yl]-4-(6-morpholin-4ylpyridin-2-ylsulfanyl) -benzamide; N-[(2S,3R)-2-methyl-1-azabicyclo[2.2.2]oct-3-yl]-4-(5methylpyrrolridin-3-ylsulfanyl)-benzamide; N-[(2S,3R)-2-methyl-1-azabicyclo[2.2.2]oct-3-yl]-4-(5--chloropyridin-3-ylsulfa nyl)-benzamide; N-[(2S,3R)-2-methyl-1-azabicyclo[2.2.2]oct -3-yl]-4-(5methoxypyridin-3-ylsulfanyl)-benzamide; N-[(2S,3R)-2-methyl -1-azabicyclo[2.2.2]oct-3-yl]-4-(5trifluoromethylpyrrolridin-3-ylsulfanyl)-benzamide; N -[(2S,3R)-2-methyl-1-azabicyclo[2.2.2]oct-3-yl]-4-(5-acetylpyridin-3-ylsulfanyl) -benzamide; N-[(2S,3R)-2-methyl-1-azabicyclo[2.2.2]oct-3-yl]-4-(5-acetaminopyridin-3-ylsulfanyl)-benzamide; N-[(2S,3R)-2-methyl-1-azabicyclo[2.2.2]oct-3-yl]-4-(5cyanopyridin-3-ylsulfanyl)-benzamide; N-[(2S,3R)-2-methyl-1-azabicyclo-[2.2.2]oct-3-yl]-4-(5morpholin-4ylpyridin-3-ylsulfanyl)-benzamide; N-[(2S,3R)-2-methyl-1-azabicyclo[2.2.2]oct-3-yl]-4-(2--chloropyridin-3-ylsulfanyl)-benzarmide; N-[(2S,3R)-2-methyl-1-azabicyclo[2.2.2]oct-3-yl]-4-(4--chloropyridin-3-ylsulfanyl)-benzamide; N-[(2S,3R)-2-methyl-1-azabicyclo[2.2.2]oct -3-yl]-4-(3-chloropyridin-4-ylsulfanyl)-benzamide; N-[(2S,3R)-2-methyl-1-azabicyclo[2.2.2]oct-3-yl]-4-(3-chloropyridin-2-ylsulfanyl)-benzamide; or pharmaceutically acceptable salts thereof.

Materials and Methods for identifying binding constants:

Membrane Preparation. Male Sprague-Dawley rats (300–350 g) are sacrificed by decapitation and the brains (whole brain minus cerebellum) are dissected quickly, weighed and homogenized in 9 volumes/g wet weight of ice-cold 0.32 M sucrose using a rotating pestle on setting 50 (10 up and down strokes). The homogenate is centrifuged at 1,000×g for 10 minutes at 4° C. The supernatant is collected and centrifuged at 20,000×g for 20 minutes at 4° C. The resulting pellet is resuspended to a protein concentration of 1–8 mg/mL. Aliquots of 5 mL homogenate are frozen at −80° C. until needed for the assay. On the day of the assay, aliquots are thawed at room temperature and diluted with Kreb's −20 mM Hepes buffer pH 7.0 (at room temperature) containing 4.16 mM $NaHCO_3$, 0.44 mM $KH_2PO_4$, 127 mM NaCl, 5.36 mM KCl, 1.26 mM $CaCl_2$, and 0.98 mM $MgCl_2$, so that 25–150 μg protein are added per test tube. Proteins are determined by the Bradford method (Bradford, M. M., Anal. Biochem., 72, 248–254, 1976) using bovine serum albumin as the standard.

Binding Assay. For saturation studies, 0.4 mL homogenate are added to test tubes containing buffer and various concentrations of radioligand, and are incubated in a final volume of 0.5 mL for 1 hour at 25° C. Nonspecific binding was determined in tissues incubated in parallel in the presence of 0.05 ml -MLA for a final concentration of 1 μM -MLA, added before the radioligand. In competition studies, drugs are added in increasing concentrations to the test tubes before addition of 0.05 ml [$^3$H]--MLA for a final concentration of 3.0 to 4.0 nM [$^3$H]--MLA. The incubations are terminated by rapid vacuum filtration through Whatman GF/B glass filter paper mounted on a 48 well Brandel cell harvester. Filters are pre-soaked in 50 mM Tris HCl pH 7.0–0.05% polyethylenimine. The filters are rapidly washed two times with 5 mL aliquots of cold 0.9% saline and then counted for radioactivity by liquid scintillation spectrometry.

Data Analysis. In competition binding studies, the inhibition constant (Ki) was calculated from the concentration dependent inhibition of [$^3$H]--MLA binding obtained from non-linear regression fitting program according to the Cheng-Prusoff equation (Cheng, Y. C. and Prussoff, W. H., Biochem. Phamacol., 22, p. 3099–3108, 1973). Hill coefficients were obtained using non-linear regression (GraphPad Prism sigmoidal dose-response with variable slope).

The aforementioned examples have the provided Ki values:

| Example # | Ki (nM) |
|---|---|
| 1 | 278 |
| 2 | 270 |
| 3 | 847 |
| 5 | 98 |
| 7 | 1577 |
| 8 | 910 |
| 12 | 1592 |
| 13 | 1240 |
| 15 | 835 |
| 16 | 414 |
| 17 | 170 |
| 23 | 1655–1980 |

What is claimed:

1. A method for treating a disease or condition in a mammal in need thereof, wherein the α7 nicotinic acetylcholine receptor is implicated, wherein the disease or condition is any one of or combination of attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulimia and anorexia nervosa, withdrawal symptoms associated with smoking cessation and dependant drug cessation, Gilles de la Tourette's Syndrome, glaucoma, neurodegeneration associated with glaucoma, or symptoms associated with pain comprising administering to the mammal a therapeutically effective amount of a compound of the Formula I:

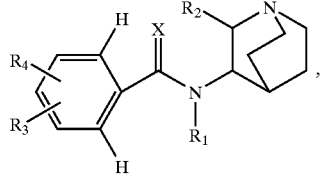

Formula I or pharmaceutically acceptable salts thereof, wherein X is O or S;

$R_1$ is independently selected from the group consisting of —H, alkyl, cycloalkyl, halogenated alkyl, and aryl;

Alkyl is both straight- and branched-chain moieties having from 1–6 carbon atoms;

Halogenated alkyl is an alkyl moiety having from 1–6 carbon atoms and having 1 to (2n+1) substituent(s) independently selected from —F, —Cl, —Br, or —I where n is the maximum number of carbon atoms in the moiety;

Cycloalkyl is a cyclic alkyl moiety having from 3–6 carbon atoms;

Aryl is phenyl, substituted phenyl, naphthyl, or substituted naphthyl;

Substituted phenyl is a phenyl either having 1–4 substituents independently selected from —F, —Cl, —Br, or —I, or having 1 substituent selected from —$R_{12}$ and 0–3 substituents independently selected from —F, —Cl, —Br, or —I;

Substituted naphthyl is a naphthalene moiety either having 1–4 substituents independently selected from —F, —Cl, —Br, or —I, or having 1 substituent selected from —$R_{12}$ and 0–3 substituents independently selected from —F, —Cl, —Br, or —I, where the substitution can be independently on either only one ring or both rings of said naphthalene moiety;

$R_2$ is —H, alkyl, halogenated alkyl, substituted alkyl, cycloalkyl, benzyl, substituted benzyl, or aryl;

Substituted alkyl is an alkyl moiety from 1–6 carbon atoms and having 0–3 substituents independently selected from —F, —Cl, —Br, or —I and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$S(O)_2NR_{10}R_{10}$, —$NR_{10}S(O)_2R_{10}$, —$NO_2$, —$R_7$, —$R_9$, phenyl, or substituted phenyl;

Substituted benzyl is a benzyl either having 1–4 substituents independently selected from —F, —Cl, —Br, or —I, or having 1 substituent selected from —$R_{12}$ and 0–3 substituents independently selected from —F, —Cl, —Br, or —I, provided that all substitution is on the phenyl ring of the benzyl;

$R_3$ is selected from the group consisting of —H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, aryl, —$R_7$, —$R_9$, —$OR_8$, —$SR_8$, —F, —Cl, —Br, —I, —$NR_8R_8$, —$C(O)R_8$, —CN, —$C(O)NR_8R_8$, —$NR_8C(O)R_8$, —$S(O)R_8$, —$OS(O)_2R_8$, —$NR_8S(O)_2R_8$, —$NO_2$, and —$N(H)C(O)N(H)R_8$;

Alkenyl is straight- and branched-chain moieties having from 2–6 carbon atoms and having at least one carbon-carbon double bond;

Halogenated alkenyl is an unsaturated alkenyl moiety having from 2–6 carbon atoms and having 1 to (2n–1) substituent(s) independently selected from —F, —Cl, —Br, or —I where n is the maximum number of carbon atoms in the moiety;

Substituted alkenyl is an unsaturated alkenyl moiety having from 2–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —$C(O)NR_{10}R_{10}$, —$NR_{10}C(O)R_{10}$, —$S(O)_2NR_{10}R_{10}$, —$NR_{10}S(O)_2R_{10}$, —CN, phenyl, or substituted phenyl;

Alkynyl is straight- and branched-chained moieties having from 2–6 carbon atoms and having at least one carbon-carbon triple bond;

Halogenated alkynyl is an unsaturated alkynyl moiety having from 3–6 carbon atoms and having 1 to (2n–3) substituent(s) independently selected from —F, —Cl, —Br, or —I where n is the maximum number of carbon atoms in the moiety;

Substituted alkynyl is an unsaturated alkynyl moiety having from 3–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —$C(O)NR_{10}R_{10}$, —$NR_{10}C(O)R_{10}$, —$S(O)_2NR_{10}R_{10}$, —$NR_{10}S(O)_2R_{10}$, —CN, phenyl, or substituted phenyl;

Halogenated cycloalkyl is a cyclic moiety having from 3–6 carbon atoms and having 1–4 substituents independently selected from —F, or —Cl;

Substituted cycloalkyl is a cyclic moiety having from 3–6 carbon atoms and having 0–3 substituents independently selected from —F, or —Cl, and further having 1 substituent selected from —$OR_{10}$, —$SR_{10}$, —$NR_{10}R_{10}$, —$C(O)R_{10}$, —CN, —$C(O)NR_{10}R_{10}$, —$NR_{10}C(O)R_{10}$, —$S(O)_2NR_{10}R_{10}$, —$NR_{10}S(O)_2R_{10}$, —$NO_2$, phenyl, or substituted phenyl;

Heterocycloalkyl is a cyclic moiety having 4–7 atoms with 1–2 atoms within the ring being —S—, —N($R_3$)—, or —O—;

Halogenated heterocycloalkyl is a cyclic moiety having from 4–7 atoms with 1–2 atoms within the ring being —S—, —N($R_3$)—, or —O—, and having 1–4 substituents independently selected from —F, or —Cl;

Substituted heterocycloalkyl is a cyclic moiety having from 4–7 atoms with 1–2 atoms within the ring being —S—, —N($R_3$)—, or —O— and having 0–3 substituents independently selected from —F, or —Cl, and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$NO_2$, —$S(O)_2NR_{10}R_{10}$, —$NR_{10}S(O)_2R_{10}$, phenyl, or substituted phenyl;

$R_4$ is selected from the group consisting of —O—$R_5$, —S—$R_5$, —S(O)—$R_5$, —C(O)—$R_5$, and alkyl substituted on the ω carbon with $R_5$ where said ω carbon is determined by counting the longest carbon chain of the alkyl moiety with the C-1 carbon being the carbon attached to the phenyl ring of the core molecule and the ω carbon being the carbon furthest from said C-1 carbon;

$R_5$ is selected from aryl, $R_7$, or $R_9$;

$R_7$ is 5-membered heteroaromatic mono-cyclic moieties containing within the ring 1–3 heteroatoms independently selected from the group consisting of —O—, =N—, —N($R_{14}$)—, and —S—, and having 0–1 substituent selected from —$R_{12}$ and 0–3 substituents independently selected from —F, —Cl, —Br, or —I, or $R_7$ is a 9-membered fused-ring moiety having a 6-membered ring fused to a 5-membered ring and having the formula

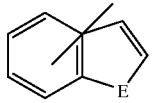

wherein E is O, S, or $NR_{14}$,

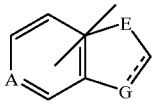

wherein E and G are independently selected from $CR_{18}$, O, S, or $NR_{14}$, and A is $CR_{18}$ or N, or

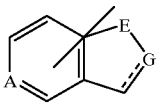

wherein E and G are independently selected from $CR_{18}$, O, S, or $NR_{14}$, and A is $CR_{18}$ or N, each 9-membered fused-ring moiety having 0–1 substituent selected from —$R_{12}$ and 0–3 substituent(s) independently selected from —F, —Cl, —Br, or —I, and having a bond directly or indirectly attached to the core molecule where valency allows in either the 6-membered or the 5-membered ring of the fused-ring moiety;

Each $R_8$ is independently selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from —$R_{12}$ and 0–3 substituent(s) independently selected from —F, —Cl, —Br, or —I, or 10-membered heteroaromatic bi-cyclic moieties containing within one or both rings 1–3 heteroatoms selected from =N—, including quinolinyl or isoquinolinyl, each 10-membered fused-ring moiety having 0–1 substituent selected from —$R_{12}$ and 0–3 substituent(s) independently selected from —F, —Cl, —Br, or —I and having a bond directly or indirectly attached to the core molecule where valency allows;

Each $R_{10}$ is independently selected from —H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or substituted phenyl;

Each $R_{11}$ is independently selected from —H, alkyl, cycloalkyl, heterocycloalkyl, halogenated alkyl, halogenated cycloalkyl, or halogenated heterocycloalkyl;

$R_{12}$ is selected from —$OR_{11}$, —$SR_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$;

$R_{13}$ is selected from —$OR_{11}$, —$SR_{11}$, —$NR_{11}R_{11}$, —$C(O)R_{11}$, —$C(O)NR_{11}R_{11}$, —CN, —$CF_3$, —$NR_{11}C(O)R_{11}$, —$S(O)_2NR_{11}R_{11}$, —$NR_{11}S(O)_2R_{11}$, or —$NO_2$;

$R_{14}$ is selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, phenyl, or substituted phenyl;

Each $R_{15}$ is independently selected from alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

Each $R_{16}$ is independently selected from cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_{17}$ is selected from cycloalkyl, halogenated cycloalkyl, substituted cycloalkyl, heterocycloalkyl, halogenated heterocycloalkyl, or substituted heterocycloalkyl; and Each $R_{18}$ is independently selected from —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, —F, —Cl, —Br, or —I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring moiety has 0–3 substituent(s) selected from —F, —Cl, —Br, or —I.

2. The method according to claim 1, wherein said compound(s) is(are) administered rectally, topically, orally, sublingually, or parenterally.

3. The method according to claim 1, wherein said compound(s) is(are) administered from about 0.001 to about 100 mg/kg of body weight of said mammal per day.

4. The method according to claim 1, wherein said compound(s) is(are) administered from about 0.1 to about 50 mg/kg of body weight of said mammal per day.

5. The method according to claim 1, wherein X is O; $R_1$ and $R_2$ are both H; and $R_3$ is selected from the group consisting of alkenyl, alkynyl, cycloalkyl, heterocycloalkyl, halogenated alkenyl, halogenated alkynyl, halogenated cycloalkyl, halogenated heterocycloalkyl, substituted alkenyl, substituted alkynyl, substituted cycloalkyl, substituted heterocycloalkyl, aryl, —$R_7$, —$R_9$, —$OR_{17}$, —$SR_8$, —$NR_{16}R_{16}$, —$C(O)R_{16}$, —CN, —$C(O)NR_{15}R_{15}$, —$NR_8C(O)R_8$, —$S(O)R_8$, —$OS(O)_2R_8$, —$NR_8S(O)_2R_8$, —$NO_2$, and —N(H)C(O)N(H)$R_8$.

6. The method according to claim 5, wherein said compound(s) is(are) administered rectally, topically, orally, sublingually, or parenterally.

7. The method according to claim 5, wherein said compound(s) is(are) administered from about 0.001 to about 100 mg/kg of body weight of said mammal per day.

8. The method according to claim 5, wherein said compound(s) is(are) administered from about 0.1 to about 50 mg/kg of body weight of said mammal per day.

9. The method according to claim 1, wherein the compound is the R stereoisomer at the C3 position of the quinuclidine of Formula I:

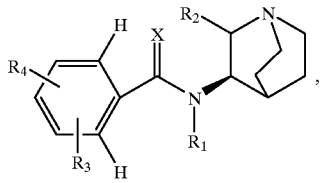

or a pharmaceutically acceptable salt thereof.

10. The method according to claim 9, wherein said compound(s) is(are) administered rectally, topically, orally, sublingually, or parenterally.

11. The method according to claim 9, wherein said compound(s) is(are) administered from about 0.001 to about 100 mg/kg of body weight of said mammal per day.

12. The method according to claim 9, wherein said compound(s) is(are) administered from about 0.1 to about 50 mg/kg of body weight of said mammal per day.

13. The method according to claim 9, wherein X is O.

14. The method according to claim 13, wherein said compound(s) is(are) administered rectally, topically, orally, sublingually, or parenterally.

15. The method according to claim 13, wherein said compound(s) is(are) administered from about 0.001 to about 100 mg/kg of body weight of said mammal per day.

16. The method according to claim 13, wherein said compound(s) is(are) administered from about 0.1 to about 50 mg/kg of body weight of said mammal per day.

17. The method according to claim 13, wherein $R_2$ is alkyl, halogenated alkyl, substituted alkyl, cycloalkyl, benzyl, substituted benzyl, or aryl.

18. The method according to claim 17, wherein said compound(s) is(are) administered rectally, topically, orally, sublingually, or parenterally.

19. The method according to claim 17, wherein said compound(s) is(are) administered from about 0.001 to about 100 mg/kg of body weight of said mammal per day.

20. The method according to claim 17, wherein said compound(s) is(are) administered from about 0.1 to about 50 mg/kg of body weight of said mammal per day.

21. The method according to claim 17, wherein $R_2$ is alkyl, cycloalkyl, or aryl.

22. The method according to claim 21, wherein said compound(s) is(are) administered rectally, topically, orally, sublingually, or parenterally.

23. The method according to claim 21, wherein said compound(s) is(are) administered from about 0.001 to about 100 mg/kg of body weight of said mammal per day.

24. The method according to claim 21, wherein said compound(s) is(are) administered from about 0.1 to about 50 mg/kg of body weight of said mammal per day.

25. The method according to claim 13, wherein $R_1$ and $R_2$ are both H.

26. The method according to claim 25, wherein said compound(s) is(are) administered rectally, topically, orally, sublingually, or parenterally.

27. The method according to claim 25, wherein said compound(s) is(are) administered from about 0.001 to about 100 mg/kg of body weight of said mammal per day.

28. The method according to claim 25, wherein said compound(s) is(are) administered from about 0.1 to about 50 mg/kg of body weight of said mammal per day.

29. The method according to claim 25, wherein $R_4$ is located at the C4 position of the phenyl ring.

30. The method according to claim 29, wherein said compound(s) is(are) administered rectally, topically, orally, sublingually, or parenterally.

31. The method according to claim 29, wherein said compound(s) is(are) administered from about 0.001 to about 100 mg/kg of body weight of said mammal per day.

32. The method according to claim 29, wherein said compound(s) is(are) administered from about 0.1 to about 50 mg/kg of body weight of said mammal per day.

33. The method according to claim 29, wherein $R_4$ is —O—$R_5$.

34. The method according to claim 33, wherein said compound(s) is(are) administered rectally, topically, orally, sublingually, or parenterally.

35. The method according to claim 33, wherein said compound(s) is(are) administered from about 0.001 to about 100 mg/kg of body weight of said mammal per day.

36. The method according to claim 33, wherein said compound(s) is(are) administered from about 0.1 to about 50 mg/kg of body weight of said mammal per day.

37. The method according to claim 29, wherein $R_4$ is —S—$R_5$.

38. The method according to claim 37, wherein said compound(s) is(are) administered rectally, topically, orally, sublingually, or parenterally.

39. The method according to claim 37, wherein said compound(s) is(are) administered from about 0.001 to about 100 mg/kg of body weight of said mammal per day.

40. The method according to claim 37, wherein said compound(s) is(are) administered from about 0.1 to about 50 mg/kg of body weight of said mammal per day.

41. The method according to claim 29, wherein $R_4$ is —S(O)—$R_5$.

42. The method according to claim 41, wherein said compound(s) is(are) administered rectally, topically, orally, sublingually, or parenterally.

43. The method according to claim 41, wherein said compound(s) is(are) administered from about 0.001 to about 100 mg/kg of body weight of said mammal per day.

44. The method according to claim 41, wherein said compound(s) is(are) administered from about 0.1 to about 50 mg/kg of body weight of said mammal per day.

45. The method according to claim 29, wherein $R_4$ is —C(O)—$R_5$.

46. The method according to claim 45, wherein said compound(s) is(are) administered rectally, topically, orally, sublingually, or parenterally.

47. The method according to claim 45, wherein said compound(s) is(are) administered from about 0.001 to about 100 mg/kg of body weight of said mammal per day.

48. The method according to claim 45, wherein said compound(s) is(are) administered from about 0.1 to about 50 mg/kg of body weight of said mammal per day.

49. The method according to claim 29, wherein $R_4$ is alkyl substituted on the ω carbon with $R_5$.

50. The method according to claim 49, wherein said compound(s) is(are) administered rectally, topically, orally, sublingually, or parenterally.

51. The method according to claim 49, wherein said compound(s) is(are) administered from about 0.001 to about 100 mg/kg of body weight of said mammal per day.

52. The method according to claim 49, wherein said compound(s) is(are) administered from about 0.1 to about 50 mg/kg of body weight of said mammal per day.

53. The method according to claim 9, wherein the compound is selected from the group consisting of:

N-[(3R)-1-azabicyclo[2.2.2]oct-3-yl]-4-(4-hydroxyphenoxy)benzamide;
N-[(3R)-1-azabicyclo[2.2.2]oct-3-yl]-4-(4-acetamidophenoxy)benzamide;
N-](3R)-1-azabicyclo[2.2.2]oct-3-yl]-4-phenoxybenzamide;
N-[(3R)-1-azabicyclo[2.2.2]oct-3-yl]-4-benzylbenzamide;
N-[(3R)-1-azabicyclo[2.2.2]oct-3-yl]-4-(phenylsulfanyl)benzamide;
N-[(3R)-1-azabicyclo[2.2.2]oct-3-yl]-3-phenoxybenzamide;
N-[(3R)-1-azabicyclo[2.2.2]oct-3-yl]-4-benzoylbenzamide;
N-[(3R)-1-azabicyclo[2.2.2]oct-3-yl]-4-(4-fluorophenoxy)benzamide;
N-[(3R)-1-azabicyclo[2.2.2]oct-3-yl]-4-(2-fluorophenoxy)benzamide;
N-[(3R)-1-azabicyclo[2.2.2]oct-3-yl]-4-(3-fluorophenoxy)benzamide;
N-[(3R)-1-azabicyclo[2.2.2]oct-3-yl]-4-(2-chlorophenoxy)benzamide;
N-[(3R)-1-azabicyclo[2.2.2]oct-3-yl]-4-(3-chlorophenoxy)benzamide;
N-[(3R)-1-azabicyclo[2.2.2]oct-3-yl]-4-(4-chlorophenoxy)benzamide;
N-[(3R)-1-azabicyclo[2.2.2]oct-3-yl]-4-(2-methoxyphenoxy)benzamide;
N-[(3R)-1-azabicyclo[2.2.2]oct-3-yl]-4-(3-methoxyphenoxy)benzamide;
N-[(3R)-1-azabicyclo[2.2.2]oct-3-yl]-4-(4-methoxyphenoxy)benzamide;
N-[(3R)-1-azabicyclo[2.2.2]oct-3-yl]-4-(3-chlorophenylsulfanyl)benzamide;
N-[(3R)-1-azabicyclo[2.2.2]oct-3-yl]-4-(4-chlorophenylsulfanyl)benzamide;
N-[(3R)-1-azabicyclo[2.2.2]oct-3-yl]-4-(2-chlorophenylsulfanyl)benzamide;
N-[(3R)-1-azabicyclo[2.2.2]oct-3-yl]-4-(4-methoxyphenylsulfanyl)-benzamide;
N-[(3R)-1-azabicyclo[2.2.2]oct-3-yl]-4-(3-methoxyphenylsulfanyl)-benzamide;
N-[(3R)-1-azabicyclo[2.2.2]oct-3-yl]-4-(2-methoxyphenylsulfanyl)-benzamide;
N-(2-methyl1-azabicyclo[2.2.2]oct-3-yl)-4-phenoxybenzamide;

and a pharmaceutically acceptable salt thereof.

54. The method according to claim 53, wherein said compound(s) is(are) administered rectally, topically, orally, sublingually, or parenterally.

55. The method according to claim 53, wherein said compound(s) is(are) administered from about 0.001 to about 100 mg/kg of body weight of said mammal per day.

56. The method according to claim 53, wherein said compound(s) is(are) administered from about 0.1 to about 50 mg/kg of body weight of said mammal per day.

57. The method according to claim 9, wherein anyone of or combination of the compounds including:

N-[(2S,3R)-2-methyl-1-azabicyclo[2.2.2]oct-3-yl]-4-(4-hydroxyphenoxy)benzamide;
N-[(2S,3R)-2-methyl-1-azabicyclo[2.2.2]oct-3-yl]-4-(4-acetamidophenoxy)benzamide;
N-[(2S,3R)-2-methyl-1-azabicyclo[2.2.2]oct-3-yl]-4-phenoxybenzamide;
N-[(2S,3R)-2-methyl-1-azabicyclo[2.2.2]oct-3-yl]-4-benzylbenzamide;
N-[(2S,3R)-2-methyl-1-azabicyclo[2.2.2]oct-3-yl]-4-(phenylsulfanyl)benzamide;
N-[(2S,3R)-2-methyl-1-azabicyclo[2.2.2]oct-3-yl]-3-phenoxybenzamide;
N-[(2S,3R)-2-methyl-1-azabicyclo[2.2.2]oct-3-yl]-4-benzoylbenzamide;
N-[(2S,3R)-2-methyl-1-azabicyclo[2.2.2]oct-3-yl]-4-(4-fluorophenoxy)benzamide;
N-[(2S,3R)-2-methyl-1-azabicyclo[2.2.2]oct-3-yl]-4-(2-fluorophenoxy)benzamide;
N-[(2S,3R)-2-methyl-1-azabicyclo[2.2.2]oct-3-yl]-4-(3-fluorophenoxy)benzamide;
N-[(2S,3R)-2-methyl-1-azabicyclo[2.2.2]oct-3-yl]-4-(2-chlorophenoxy)benzamide;
N-[(2S,3R)-2-methyl-1-azabicyclo[2.2.2]oct-3-yl]-4-(3-chlorophenoxy)benzamide;
N-[(2S,3R)-2-methyl-1-azabicyclo[2.2.2]oct-3-yl]-4-(4-chlorophenoxy)benzamide;
N-[(2S,3R)-2-methyl-1-azabicyclo[2.2.2]oct-3-yl]-4-(2-methoxyphenoxy)benzamide;
N-[(2S,3R)-2-methyl-1-azabicyclo[2.2.2]oct-3-yl]-4-(3-methoxyphenoxy)benzamide;
N-[(2S,3R)-2-methyl-1-azabicyclo[2.2.2]oct-3-yl]-4-(4-methoxyphenoxy)benzamide;
N-[(2S,3R)-2-methyl-1-azabicyclo[2.2.2]oct-3-yl]-4-(3-chlorophenylsulfanyl)benzamide;
N-[(2S,3R)-2-methyl-1-azabicyclo[2.2.2]oct-3-yl]-4-(4-chlorophenylsulfanyl)benzamide;
N-[(2S,3R)-2-methyl-1-azabicyclo[2.2.2]oct-3-yl]-4-(2-chlorophenylsulfanyl)benzamide;
N-[(2S,3R)-2-methyl-1-azabicyclo[2.2.2]oct-3-yl]-4-(4-methoxyphenylsulfanyl)-benzamide;
N-[(2S,3R)-2-methyl-1-azabicyclo[2.2.2]oct-3-yl]-4-(3-methoxyphenylsulfanyl)-benzamide;
N-[(2S,3R)-2-methyl-1-azabicyclo[2.2.2]oct-3-yl]-4-(2-methoxyphenylsulfanyl)-benzamide;
N-[(2S,3R)-2-methyl-1-azabicyclo[2.2.2]oct-3-yl]-4-phenoxybenzamide;
N-[(3R)-1-azabicyclo[2.2.2]oct-3-yl]-4-(4-aminophenoxy)-benzamide;
N-[(3R)-1-azabicyclo[2.2.2]oct-3-yl]-4-(3-aminophenoxy)-benzamide;
N-[(3R)-1-azabicyclo[2.2.2]oct-3-yl]-4-(2-aminophenoxy)-benzamide;
N-[(3R)-1-azabicyclo[2.2.2]oct-3-yl]-4-(4-methanesulfonylamino-phenoxy)-benzamide;
N-[(3R)-1-azabicyclo[2.2.2]oct-3-yl]-4-(3-methanesulfonylamino-phenoxy)-benzamide;
N-[(3R)-1-azabicyclo[2.2.2]oct-3-yl]-4-(2-methanesulfonylamino-phenoxy)-benzamide;
N-[(3R)-1-azabicyclo[2.2.2]oct-3-yl]-4-(4-acetoxyphenoxy)-benzamide;
N-[(3R)-1-azabicyclo[2.2.2]oct-3-yl]-4-(3-acetoxyphenoxy)-benzamide;
N-[(3R)-1-azabicyclo[2.2.2]oct-3-yl]-4-(2-acetoxyphenoxy)-benzamide;
N-[(3R)-1-azabicyclo[2.2.2]oct-3-yl]-4-(4-acetylphenoxy)-benzamide;
N-[(3R)-1-azabicyclo[2.2.2]oct-3-yl]-4-(3-acetylphenoxy)-benzamide;
N-[(3R)-1-azabicyclo[2.2.2]oct-3-yl]-4-(2-acetylphenoxy)-benzamide;
N-[(3R)-1-azabicyclo[2.2.2]oct-3-yl]-4-(4-carbamoylphenoxy)-benzamide;
N-[(3R)-1-azabicyclo[2.2.2]oct-3-yl]-4-(3-carbamoylphenoxy)-benzamide;
N-[(3R)-1-azabicyclo[2.2.2]oct-3-yl]-4-(2-carbamoylphenoxy)-benzamide;
N-[(3R)-1-azabicyclo[2.2.2]oct-3-yl]-4-(4-cyanophenoxy)-benzamide;
N-[(3R)-1-azabicyclo[2.2.2]oct-3-yl]-4-(3-cyanophenoxy)-benzamide;
N-[(3R)-1-azabicyclo[2.2.2]oct-3-yl]-4-(2-cyanophenoxy)-benzamide;
N-[(3R)-1-azabicyclo[2.2.2]oct-3-yl]-4-(4-sulfamoylphenoxy)-benzamide;

N-[(3R)-1-azabicyclo[2.2.2]oct-3-yl]-4-(3-sulfamoylphenoxy)-benzamide; N-[(3R)-1-azabicyclo[2.2.2]oct-3-yl]-4-(2-sulfamoylphenoxy)-benzamide; N-[(3R)-1-azabicyclo[2.2.2]oct-3-yl]-4-(thiophen-2-yloxy)-benzamide; N-[(3R)-1-azabicyclo[2.2.2]oct-3-yl]-4-(5-methy-thiophen-2-yloxy)-benzamide; N-[(3R)-1-azabicyclo[2.2.2]oct-3-yl]-4-(5-chlorothiophen-2-yloxy)-benzamide; N-[(3R)-1-azabicyclo[2.2.2]oct-3-yl]-4-(5-methoxythiophen-2-yloxy)-benzamide; N-[(3R)-1-azabicyclo[2.2.2]oct-3-yl]-4-(5-trifluoromethy-thiophen-2-yloxy)-benzamide; N-[(3R)-1-azabicyclo[2.2.2]oct-3-yl]-4-(5-acety-thiophen-2-yloxy)-benzamide; N-[(3R)-1-azabicyclo[2.2.2]oct-3-yl]-4-(5-acetaminothiophen-2-yloxy)-benzamide; N-[(3R)-1-azabicyclo[2.2.2]oct-3-yl]-4-(5-cyanothiophen-2-yloxy)-benzamide; N-[(3R)-1-azabicyclo[2.2.2]oct-3-yl]-4-(5-morpholin-4-yl-thiophen-2-yloxy)-benzamide; N-[(3R)-1-azabicyclo[2.2.2]oct-3-yl]-4-(4-methy-thiophen-2-yloxy)-benzamide; N-[(3R)-1-azabicyclo[2.2.2]oct-3-yl]-4-(4-chlorothiophen-2-yloxy)-benzamide; N-[(3R)-1-azabicyclo[2.2.2]oct-3-yl]-4-(4-methoxythiophen-2-yloxy)-benzamide; N-[(3R)-1-azabicyclo[2.2.2]oct-3-yl]-4-(4-trifluoromethy-thiophen-2-yloxy)-benzamide; N-[(3R)-1-azabicyclo[2.2.2]oct-3-yl]-4-(4-acety-thiophen-2-yloxy)-benzamide; N-[(3R)-1-azabicyclo[2.2.2]oct-3-yl]-4-(4-acetaminothiophen-2-yloxy)-benzamide; N-[(3R)-1-azabicyclo[2.2.2]oct-3-yl]-4-(4-cyanothiophen-2-yloxy)-benzamide; N-[(3R)-1-azabicyclo[2.2.2]oct-3-yl]-4-(4-morpholin-4-yl-thiophen-2-yloxy)-benzamide; N-[(3R)-1-azabicyclo[2.2.2]oct-3-yl]-4-(furan-2-yloxy)-benzamide; N-[(3R)-1-azabicyclo[2.2.2]oct-3-yl]-4-(5-methylfuran-2-yloxy)-benzamide; N-[(3R)-1-azabicyclo[2.2.2]oct-3-yl]-4-(5-chlorofuran-2-yloxy)-benzamide; N-[(3R)-1-azabicyclo[2.2.2]oct-3-yl]-4-(5-methoxyfuran-2-yloxy)-benzamide; N-[(3R)-1-azabicyclo[2.2.2]oct-3-yl]-4-(5-trifluoromethylfuran-2-yloxy)-benzamide; N-[(3R)-1-azabicyclo[2.2.2]oct-3-yl]-4-(5-acetylfuran-2-yloxy)-benzamide; N-[(3R)-1-azabicyclo[2.2.2]oct-3-yl]-4-(5-acetaminofuran-2-yloxy)-benzamide; N-[(3R)-1-azabicyclo[2.2.2]oct-3-yl]-4-(5-cyanofuran-2-yloxy)-benzamide; N-[(3R)-1-azabicyclo[2.2.2]oct-3-yl]-4-(5-morpholin-4-yl-furan-2-yloxy)-benzamide; N-[(3R)-1-azabicyclo[2.2.2]oct-3-yl]-4-(4-methylfuran-2-yloxy)-benzamide; N-[(3R)-1-azabicyclo[2.2.2]oct-3-yl]-4-(4-chlorofuran-2-yloxy)-benzamide; N-[(3R)-1-azabicyclo[2.2.2]oct-3-yl]-4-(4-methoxyfuran-2-yloxy)-benzamide; N-[(3R)-1-azabicyclo[2.2.2]oct-3-yl]-4-(4-trifluoromethylfuran-2-yloxy)-benzamide; N-[(3R)-1-azabicyclo[2.2.2]oct-3-yl]-4-(4-acetylfuran-2-yloxy)-benzamide; N-[(3R)-1-azabicyclo[2.2.2]oct-3-yl]-4-(4-acetaminofuran-2-yloxy)-benzamide; N-[(3R)-1-azabicyclo[2.2.2]oct-3-yl]-4-(4-cyanofuran-2-yloxy)-benzamide; N-[(3R)-1-azabicyclo[2.2.2]oct-3-yl]-4-(4-morpholin-4-yl-furan-2-yloxy)-benzamide; N-[(3R)-1-azabicyclo[2.2.2]oct-3-yl]-4-(oxazol-2-yloxy)-benzamide; N-[(3R)-1-azabicyclo[2.2.2]oct-3-yl]-4-(5-methyloxazol-2-yloxy)-benzamide; N-[(3R)-1-azabicyclo[2.2.2]oct-3-yl]-4-(5-chlorooxazol-2-yloxy)-benzamide; N-[(3R)-1-azabicyclo[2.2.2]oct-3-yl]-4-(5-methoxyoxazol-2-yloxy)-benzamide; N-[(3R)-1-azabicyclo[2.2.2]oct-3-yl]-4-(5-trifluoromethyloxazol-2-yloxy)-benzamide; N-[(3R)-1-azabicyclo[2.2.2]oct-3-yl]-4-(5-acetyloxazol-2-yloxy)-benzamide; N-[(3R)-1-azabicyclo[2.2.2]oct-3-yl]-4-(5-acetaminooxazol-2-yloxy)-benzamide; N-[(3R)-1-azabicyclo[2.2.2]oct-3-yl]-4-(5-cyanooxazol-2-yloxy)-benzamide; N-[(3R)-1-azabicyclo[2.2.2]oct-3-yl]-4-(5-morpholin-4-yl-oxazol-2-yloxy)-benzamide; N-[(3R)-1-azabicyclo[2.2.2]oct-3-yl]-4-(oxazol-2-yloxy)-benzamide; N-[(3R)-1-azabicyclo[2.2.2]oct-3-yl]-4-(4-methyloxazol-2-yloxy)-benzamide; N-[(3R)-1-azabicyclo[2.2.2]oct-3-yl]-4-(4-chlorooxazol-2-yloxy)-benzamide; N-[(3R)-1-azabicyclo[2.2.2]oct-3-yl]-4-(4-methoxyoxazol-2-yloxy)-benzamide; N-[(3R)-1-azabicyclo[2.2.2]oct-3-yl]-4-(4-trifluoromethyloxazol-2-yloxy)-benzamide; N-[(3R)-1-azabicyclo[2.2.2]oct-3-yl]-4-(4-acetyloxazol-2-yloxy)-benzamide; N-[(3R)-1-azabicyclo[2.2.2]oct-3-yl]-4-(4-acetaminooxazol-2-yloxy)-benzamide; N-[(3R)-1-azabicyclo[2.2.2]oct-3-yl]-4-(4-cyanooxazol-2-yloxy)-benzamide; N-[(3R)-1-azabicyclo[2.2.2]oct-3-yl]-4-(4-morpholin-4-yl-oxazol-2-yloxy)-benzamide; N-[(3R)-1-azabicyclo[2.2.2]oct-3-yl]-4-(oxazol-5-yloxy)-benzamide; N-[(3R)-1-azabicyclo[2.2.2]oct-3-yl]-4-(2-methyloxazol-5-yloxy)-benzamide; N-[(3R)-1-azabicyclo[2.2.2]oct-3-yl]-4-(2-chlorooxazol-5-yloxy)-benzamide; N-[(3R)-1-azabicyclo[2.2.2]oct-3-yl]-4-(2-methoxyoxazol-5-yloxy)-benzamide; N-[(3R)-1-azabicyclo[2.2.2]oct-3-yl]-4-(2-trifluoromethyloxazol-5-yloxy)-benzamide; N-[(3R)-1-azabicyclo[2.2.2]oct-3-yl]-4-(2-acetyloxazol-5-yloxy)-benzamide; N-[(3R)-1-azabicyclo[2.2.2]oct-3-yl]-4-(2-acetaminooxazol-5-yloxy)-benzamide; N-[(3R)-1-azabicyclo[2.2.2]oct-3-yl]-4-(2-cyanooxazol-5-yloxy)-benzamide; N-[(3R)-1-azabicyclo[2.2.2]oct-3-yl]-4-(2-morpholin-4-yl-oxazol-5-yloxy)-benzamide; N-[(3R)-1-azabicyclo[2.2.2]oct-3-yl]-4-(thiazol-2-yloxy)-benzamide; N-[(3R)-1-azabicyclo[2.2.2]oct-3-yl]-4-(5-methylthiazol-2-yloxy)-benzamide; N-[(3R)-1-azabicyclo[2.2.2]oct-3-yl]-4-(5-chlorothiazol-2-yloxy)-benzamide; N-[(3R)-1-azabicyclo[2.2.2]oct-3-yl]-4-(5-methoxythiazol-2-yloxy)-benzamide; N-[(3R)-1-azabicyclo[2.2.2]oct-3-yl]-4-(5-trifluoromethylthiazol-2-yloxy)-benzamide; N-[(3R)-1-azabicyclo[2.2.2]oct-3-yl]-4-(5-acetylthiazol-2-yloxy)-benzamide; N-[(3R)-1-azabicyclo[2.2.2]oct-3-yl]-4-(5-acetaminothiazol-2-yloxy)-benzamide; N-[(3R)-1-azabicyclo[2.2.2]oct-3-yl]-4-(5-cyanothiazol-2-yloxy)-benzamide; N-[(3R)-1-azabicyclo[2.2.2]oct-3-yl]-4-(5-morpholin-4-yl-thiazol-2-yloxy)-benzamide; N-[(3R)-1-azabicyclo[2.2.2]oct-3-yl]-4-(thiazol-2-yloxy)-benzamide; N-[(3R)-1-azabicyclo[2.2.2]oct-3-yl]-4-(4-methylthiazol-2-yloxy)-benzamide; N-[(3R)-1-azabicyclo[2.2.2]oct-3-yl]-4-(4-chlorothiazol-2-yloxy)-benzamide; N-[(3R)-1-azabicyclo[2.2.2]oct-3-yl]-4-(4-methoxythiazol-2-yloxy)-benzamide; N-[(3R)-1-azabicyclo[2.2.2]oct-3-yl]-4-(4-trifluoromethylthiazol-2-yloxy)-benzamide; N-[(3R)-1-azabicyclo[2.2.2]oct-3-yl]-4-(4-acetylthiazol-2-yloxy)-benzamide; N-[(3R)-1-azabicyclo[2.2.2]oct-3-yl]-4-(4-acetaminothiazol-2-yloxy)-benzamide; N-[(3R)-1-azabicyclo[2.2.2]oct-3-yl]-4-(4-cyanothiazol-2-yloxy)-benzamide; N-[(3R)-1-azabicyclo[2.2.2]oct-3-yl]-4-(4-morpholin-4-yl-thiazol-2-yloxy)-benzamide; N-[(3R)-1-azabicyclo[2.2.2]oct-3-yl]-4-(thiazol-5-yloxy)-benzamide; N-[(3R)-1-azabicyclo[2.2.2]oct-3-yl]-4-(2- methylthiazol-5-yloxy)-benzamide; N-[(3R)-1-azabicyclo[2.2.2]oct-3-yl]-4-(2-chlorothiazol-5-yloxy)-benzamide; N-[(3R)-1-azabicyclo[2.2.2]oct-3-yl]-4-(2-methoxythiazol-5-yloxy)-benzamide; N-[(3R)-1-azabicyclo[2.2.2]oct-3-yl]-4-(2-trifluoromethylthiazol-5-yloxy)-benzamide; N-[(3R)-1-azabicyclo[2.2.2]oct-3-yl]-4-(2-acetylthiazol-5-yloxy)-benzamide; N-[(3R)-1-azabicyclo[2.2.2]oct-3-yl]-4-(2-acetaminothiazol-5-yloxy)-benzamide; N-[(3R)-1-azabicyclo[2.2.2]oct-3-yl]-4-(2-cyanothiazol-5-yloxy)-benzamide; N-[(3R)-1-azabicyclo[2.2.2]oct-3-yl]-4-(2-morpholin-4-yl-thiazol-5-yloxy)-benzamide; N-[(3R)-1-azabicyclo[2.2.2]oct-3-yl]-4-([1,3,4]oxadiazol-2-yloxy)-benzamide; N-[(3R)-1-azabicyclo[2.2.2]oct-3-yl]-4-(5-methyl[1,3,4]oxadiazol-2-yloxy)-benzamide; N-[(3R)-1-azabicyclo[2.2.2]oct-3-yl]-4-(5-chloro[1,3,4]oxadiazol-2-yloxy)-benzamide; N-[(3R)-1-azabicyclo[2.2.2]oct-3-yl]-4-(5-methoxy[1,3,4]oxadiazol-2-yloxy)-benzamide; N-[(3R)-1-azabicyclo[2.2.2]oct-3-yl]-4-(5-trifluoromethyl[1,3,4]oxadiazol-2-yloxy)-benzamide; N-[(3R)-1-azabicyclo[2.2.2]oct-3-yl]-4-(5-acetyl[1,3,4]oxadiazol-2-yloxy)-benzamide; N-[(3R)-1-azabicyclo[2.2.2]oct-3-yl]-4-(5-acetamino[1,3,4]oxadiazol-2-yloxy)-benzamide; N-[(3R)-1-azabicyclo[2.2.2]oct-3-yl]-4-(5-cyano[1,3,4]oxadiazol-2-yloxy)-benzamide; N-[(3R)-1-azabicyclo[2.2.2]oct-3-yl]-4-(5-morpholin-4-yl-[1,3,4]oxadiazol-2-yloxy)-benzamide; N-[(3R)-1-azabicyclo[2.2.2]oct-3-yl]-4-([1,3,4]thiadiazol-2-yloxy)-benzamide; N-[(3R)-1-azabicyclo[2.2.2]oct-3-yl]-4-(5-methyl[1,3,4]thiadiazol-2-yloxy)-benzamide; N-[(3R)-1-azabicyclo[2.2.2]oct-3-yl]-4-(5-chloro[1,3,4]thiadiazol-2-yloxy)-benzamide; N-[(3R)-1-azabicyclo[2.2.2]oct-3-yl]-4-(5-methoxy[1,3,4]thiadiazol-2-yloxy)-benzamide; N-[(3R)-1-azabicyclo[2.2.2]oct-3-yl]-4-(5-trifluoromethyl[1,3,4]thiadiazol-2-yloxy)-benzamide; N-[(3R)-1-azabicyclo[2.2.2]oct-3-yl]-4-(5-acetyl[1,3,4]thiadiazol-2-yloxy)-benzamide; N-[(3R)-1-azabicyclo[2.2.2]oct-3-yl]-4-(5-acetamino[1,3,4]thiadiazol-2-yloxy)-benzamide; N-[(3R)-1-azabicyclo[2.2.2]oct-3-yl]-4-(5-cyano[1,3,4]thiadiazol-2-yloxy)-benzamide; N-[(3R)-1-azabicyclo[2.2.2]oct-3-yl]-4-(5-morpholin-4-yl-[1,3,4]thiadiazol-2-yloxy)-benzamide; N-[(3R)-1-azabicyclo[2.2.2]oct-3-yl]-4-(4-aminophenylsulfanyl)-benzamide; N-[(3R)-1-azabicyclo[2.2.2]oct-3-yl]-4-(3-aminophenylsulfanyl)-benzamide; N-[(3R)-1-azabicyclo[2.2.2]oct-3-yl]-4-(2-aminophenylsulfanyl)-benzamide; N-[(3R)-1-azabicyclo[2.2.2]oct-3-yl]-4-(4-methanesulfonylamino-phenylsulfanyl)-benzamide; N-[(3R)-1-azabicyclo[2.2.2]oct-3-yl]-4-(3-methanesulfonylamino-phenylsulfanyl)-benzamide; N-[(3R)-1-azabicyclo[2.2.2]oct-3-yl]-4-(2-methanesulfonylamino-phenylsulfanyl)-benzamide; N-[(3R)-1-azabicyclo[2.2.2]oct-3-yl]-4-(4-acetoxyphenylsulfanyl)-benzamide; N-[(3R)-1-azabicyclo[2.2.2]oct-3-yl]-4-(3-acetoxyphenylsulfanyl)-benzamide; N-[(3R)-1-azabicyclo[2.2.2]oct-3-yl]-4-(2-acetoxyphenylsulfanyl)-benzamide; N-[(3R)-1-azabicyclo[2.2.2]oct-3-yl]-4-(4-acetylphenylsulfanyl)-benzamide; N-[(3R)-1-azabicyclo[2.2.2]oct-3-yl]-4-(3-acetylphenylsulfanyl)-benzamide; N-[(3R)-1-azabicyclo[2.2.2]oct-3-yl]-4-(2-acetylphenylsulfanyl)-benzamide; N-[(3R)-1-azabicyclo[2.2.2]oct-3-yl]-4-(4-carbamoylphenylsulfanyl)-benzamide; N-[(3R)-1-azabicyclo[2.2.2]oct-3-yl]-4-(3-carbamoylphenylsulfanyl)-benzamide; N-[(3R)-1-azabicyclo[2.2.2]oct-3-yl]-4-(2-carbamoylphenylsulfanyl)-benzamide; N-[(3R)-1-azabicyclo[2.2.2]oct-3-yl]-4-(4-cyanophenylsulfanyl)-benzamide; N-[(3R)-1-azabicyclo[2.2.2]oct-3-yl]-4-(3-cyanophenylsulfanyl)-benzamide; N-[(3R)-1-azabicyclo[2.2.2]oct-3-yl]-4-(2-cyanophenylsulfanyl)-benzamide; N-[(3R)-1-azabicyclo[2.2.2]oct-3-yl]-4-(4-sulfamoylphenylsulfanyl)-benzamide; N-[(3R)-1-azabicyclo[2.2.2]oct-3-yl]-4-(3-sulfamoylphenylsulfanyl)-benzamide; N-[(3R)-1-azabicyclo[2.2.2]oct-3-yl]-4-(2-sulfamoylphenylsulfanyl)-benzamide; N-[(3R)-1-azabicyclo[2.2.2]oct-3-yl]-4-(4-hydroxyphenylsulfanyl)-benzamide; N-[(3R)-1-azabicyclo[2.2.2]oct-3-yl]-4-(3-hydroxyphenylsulfanyl)-benzamide; N-[(3R)-1-azabicyclo[2.2.2]oct-3-yl]-4-(2-hydroxyphenylsulfanyl)-benzamide; N-[(3R)-1-azabicyclo[2.2.2]oct-3-yl]-4-(4-acetamidophenylsulfanyl)-benzamide; N-[(3R)-1-azabicyclo[2.2.2]oct-3-yl]-4-(3-acetamidophenylsulfanyl)-benzamide; N-[(3R)-1-azabicyclo[2.2.2]oct-3-yl]-4-(2-acetamidophenylsulfanyl)-benzamide; N-[(3R)-1-azabicyclo[2.2.2]oct-3-yl]-4-(thiophen-2-ylsulfanyl)-benzamide; N-[(3R)-1-azabicyclo[2.2.2]oct-3-yl]-4-(5-methy-thiophen-2-ylsulfanyl)-benzamide; N-[(3R)-1-azabicyclo[2.2.2]oct-3-yl]-4-(5-chlorothiophen-2-ylsulfanyl)-benzamide; N-[(3R)-1-azabicyclo[2.2.2]oct-3-yl]-4-(5-methoxythiophen-2-ylsulfanyl)-benzamide; N-[(3R)-1-azabicyclo[2.2.2]oct-3-yl]-4-(5-trifluoromethy-thiophen-2-ylsulfanyl)-benzamide; N-[(3R)-1-azabicyclo[2.2.2]oct-3-yl]-4-(5-acety-thiophen-2-ylsulfanyl)-benzamide; N-[(3R)-1-azabicyclo[2.2.2]oct-3-yl]-4-(5-acetaminothiophen-2-ylsulfanyl)-benzamide; N-[(3R)-1-azabicyclo[2.2.2]oct-3-yl]-4-(5-cyanothiophen-2-ylsulfanyl)-benzamide; N-[(3R)-1-azabicyclo[2.2.2]oct-3-yl]-4-(5-morpholin-4-yl-thiophen-2-ylsulfanyl)-benzamide; N-[(3R)-1-azabicyclo[2.2.2]oct-3-yl]-4-(4-methy-thiophen-2-ylsulfanyl)-benzamide; N-[(3R)-1-azabicyclo[2.2.2]oct-3-yl]-4-(4-chlorothiophen-2-ylsulfanyl)-benzamide; N-[(3R)-1-azabicyclo[2.2.2]oct-3-yl]-4-(4-methoxythiophen-2-ylsulfanyl)-benzamide; N-[(3R)-1-azabicyclo[2.2.2]oct-3-yl]-4-(4-trifluoromethy-thiophen-2-ylsulfanyl)-benzamide; N-[(3R)-1-azabicyclo[2.2.2]oct-3-yl]-4-(4-acety-thiophen-2-ylsulfanyl)-benzamide; N-[(3R)-1-azabicyclo[2.2.2]oct-3-yl]-4-(4-acetaminothiophen-2-ylsulfanyl)-benzamide; N-[(3R)-1-azabicyclo[2.2.2]oct-3-yl]-4-(4-cyanothiophen-2-ylsulfanyl)-benzamide; N-[(3R)-1-azabicyclo[2.2.2]oct-3-yl]-4-(4-morpholin-4-yl-thiophen-2-ylsulfanyl)-benzamide; N-[(3R)-1-azabicyclo[2.2.2]oct-3-yl]-4-(furan-2-ylsulfanyl)-benzamide; N-[(3R)-1-azabicyclo[2.2.2]oct-3-yl]-4-(5-methylfuran-2-ylsulfanyl)-benzamide; N-[(3R)-1-azabicyclo[2.2.2]oct-3-yl]-4-(5-chlorofuran-2-ylsulfanyl)-benzamide; N-[(3R)-1-azabicyclo[2.2.2]oct-3-yl]-4-(5-methoxyfuran-2-ylsulfanyl)-benzamide; N-[(3R)-1-azabicyclo[2.2.2]oct-3-yl]-4-(5-trifluoromethylfuran-2-ylsulfanyl)-benzamide; N-[(3R)-1-azabicyclo[2.2.2]oct-3-yl]-4-(5-acetylfuran-2-ylsulfanyl)-benzamide; N-[(3R)-1-azabicyclo[2.2.2]oct-3-yl]-4-(5-acetaminofuran-2-ylsulfanyl)-benzamide; N-[(3R)-1-azabicyclo[2.2.2]oct-3-yl]-4-(5-cyanofuran-2-ylsulfanyl)-benzamide;

N-[(3R)-1-azabicyclo[2.2.2]oct-3-yl]-4-(5-morpholin-4-yl-furan-2-ylsulfanyl)-benzamide; N-[(3R)-1-azabicyclo[2.2.2]oct-3-yl]-4-(4-methylfuran-2-ylsulfanyl)-benzamide; N-[(3R)-1-azabicyclo[2.2.2]oct-3-yl]-4-(4-chlorofuran-2-ylsulfanyl)-benzamide; N-[(3R)-1-azabicyclo[2.2.2]oct-3-yl]-4-(4-methoxyfuran-2-ylsulfanyl)-benzamide; N-[(3R)-1-azabicyclo[2.2.2]oct-3-yl]-4-(4-trifluoromethylfuran-2-ylsulfanyl)-benzamide; N-[(3R)-1-azabicyclo[2.2.2]oct-3-yl]-4-(4-acetylfuran-2-ylsulfanyl)-benzamide; N-[(3R)-1-azabicyclo[2.2.2]oct-3-yl]-4-(4-acetaminofuran-2-ylsulfanyl)-benzamide; N-[(3R)-1-azabicyclo[2.2.2]oct-3-yl]-4-(4-cyanofuran-2-ylsulfanyl)-benzamide; N-[(3R)-1-azabicyclo[2.2.2]oct-3-yl]-4-(4-morpholin-4-yl-furan-2-ylsulfanyl)-benzamide; N-[(3R)-1-azabicyclo[2.2.2]oct-3-yl]-4-(oxazol-2-ylsulfanyl)-benzamide; N-[(3R)-1-azabicyclo[2.2.2]oct-3-yl]-4-(5-methyloxazol-2-ylsulfanyl)-benzamide; N-[(3R)-1-azabicyclo[2.2.2]oct-3-yl]-4-(5-chlorooxazol-2-ylsulfanyl)-benzamide; N-[(3R)-1-azabicyclo[2.2.2]oct-3-yl]-4-(5-methoxyoxazol-2-ylsulfanyl)-benzamide; N-[(3R)-1-azabicyclo[2.2.2]oct-3-yl]-4-(5-trifluoromethyloxazol-2-ylsulfanyl)-benzamide; N-[(3R)-1-azabicyclo[2.2.2]oct-3-yl]-4-(5-acetyloxazol-2-ylsulfanyl)-benzamide; N-[(3R)-1-azabicyclo[2.2.2]oct-3-yl]-4-(5-acetaminooxazol-2-ylsulfanyl)-benzamide; N-[(3R)-1-azabicyclo[2.2.2]oct-3-yl]-4-(5-cyanooxazol-2-ylsulfanyl)-benzamide; N-[(3R)-1-azabicyclo[2.2.2]oct-3-yl]-4-(5-morpholin-4-yl-oxazol-2-ylsulfanyl)-benzamide; N-[(3R)-1-azabicyclo[2.2.2]oct-3-yl]-4-(oxazol-2-ylsulfanyl)-benzamide; N-[(3R)-1-azabicyclo[2.2.2]oct-3-yl]-4-(4-methyloxazol-2-ylsulfanyl)-benzamide; N-[(3R)-1-azabicyclo[2.2.2]oct-3-yl]-4-(4-chlorooxazol-2-ylsulfanyl)-benzamide; N-[(3R)-1-azabicyclo[2.2.2]oct-3-yl]-4-(4-methoxyoxazol-2-ylsulfanyl)-benzamide; N-[(3R)-1-azabicyclo[2.2.2]oct-3-yl]-4-(4-trifluoromethyloxazol-2-ylsulfanyl)-benzamide; N-[(3R)-1-azabicyclo[2.2.2]oct-3-yl]-4-(4-acetyloxazol-2-ylsulfanyl)-benzamide; N-[(3R)-1-azabicyclo[2.2.2]oct-3-yl]-4-(4-acetaminooxazol-2-ylsulfanyl)-benzamide; N-[(3R)-1-azabicyclo[2.2.2]oct-3-yl]-4-(4-cyanooxazol-2-ylsulfanyl)-benzamide; N-[(3R)-1-azabicyclo[2.2.2]oct-3-yl]-4-(4-morpholin-4-yl-oxazol-2-ylsulfanyl)-benzamide; N-[(3R)-1-azabicyclo[2.2.2]oct-3-yl]-4-(oxazol-5-ylsulfanyl)-benzamide; N-[(3R)-1-azabicyclo[2.2.2]oct-3-yl]-4-(2-methyloxazol-5-ylsulfanyl)-benzamide; N-[(3R)-1-azabicyclo[2.2.2]oct-3-yl]-4-(2-chlorooxazol-5-ylsulfanyl)-benzamide; N-[(3R)-1-azabicyclo[2.2.2]oct-3-yl]-4-(2-methoxyoxazol-5-ylsulfanyl)-benzamide; N-[(3R)-1-azabicyclo[2.2.2]oct-3-yl]-4-(2-trifluoromethyloxazol-5-ylsulfanyl)-benzamide; N-[(3R)-1-azabicyclo[2.2.2]oct-3-yl]-4-(2-acetyloxazol-5-ylsulfanyl)-benzamide; N-[(3R)-1-azabicyclo[2.2.2]oct-3-yl]-4-(2-acetaminooxazol-5-ylsulfanyl)-benzamide; N-[(3R)-1-azabicyclo[2.2.2]oct-3-yl]-4-(2-cyanooxazol-5-ylsulfanyl)-benzamide; N-[(3R)-1-azabicyclo[2.2.2]oct-3-yl]-4-(2-morpholin-4-yl-oxazol-5-ylsulfanyl)-benzamide; N-[(3R)-1-azabicyclo[2.2.2]oct-3-yl]-4-(thiazol-2-ylsulfanyl)-benzamide; N-[(3R)-1-azabicyclo[2.2.2]oct-3-yl]-4-(5-methylthiazol-2-ylsulfanyl)-benzamide; N-[(3R)-1-azabicyclo[2.2.2]oct-3-yl]-4-(5-chlorothiazol-2-ylsulfanyl)-benzamide; N-[(3R)-1-azabicyclo[2.2.2]oct-3-yl]-4-(5-methoxythiazol-2-ylsulfanyl)-benzamide; N-[(3R)-1-azabicyclo[2.2.2]oct-3-yl]-4-(5-trifluoromethylthiazol-2-ylsulfanyl)-benzamide; N-[(3R)-1-azabicyclo[2.2.2]oct-3-yl]-4-(5-acetylthiazol-2-ylsulfanyl)-benzamide; N-[(3R)-1-azabicyclo[2.2.2]oct-3-yl]-4-(5-acetaminothiazol-2-ylsulfanyl)-benzamide; N-[(3R)-1-azabicyclo[2.2.2]oct-3-yl]-4-(5-cyanothiazol-2-ylsulfanyl)-benzamide; N-[(3R)-1-azabicyclo[2.2.2]oct-3-yl]-4-(5-morpholin-4-yl-thiazol-2-ylsulfanyl)-benzamide; N-[(3R)-1-azabicyclo[2.2.2]oct-3-yl]-4-(thiazol-2-ylsulfanyl)-benzamide; N-[(3R)-1-azabicyclo[2.2.2]oct-3-yl]-4-(4-methylthiazol-2-ylsulfanyl)-benzamide; N-[(3R)-1-azabicyclo[2.2.2]oct-3-yl]-4-(4-chlorothiazol-2-ylsulfanyl)-benzamide; N-[(3R)-1-azabicyclo[2.2.2]oct-3-yl]-4-(4-methoxythiazol-2-ylsulfanyl)-benzamide; N-[(3R)-1-azabicyclo[2.2.2]oct-3-yl]-4-(4-trifluoromethylthiazol-2-ylsulfanyl)-benzamide; N-[(3R)-1-azabicyclo[2.2.2]oct-3-yl]-4-(4-acetylthiazol-2-ylsulfanyl)-benzamide; N-[(3R)-1-azabicyclo[2.2.2]oct-3-yl]-4-(4-acetaminothiazol-2-ylsulfanyl)-benzamide; N-[(3R)-1-azabicyclo[2.2.2]oct-3-yl]-4-(4-cyanothiazol-2-ylsulfanyl)-benzamide; N-[(3R)-1-azabicyclo[2.2.2]oct-3-yl]-4-(4-morpholin-4-yl-thiazol-2-ylsulfanyl)-benzamide; N-[(3R)-1-azabicyclo[2.2.2]oct-3-yl]-4-(thiazol-5-ylsulfanyl)-benzamide; N-[(3R)-1-azabicyclo[2.2.2]oct-3-yl]-4-(2-methylthiazol-5-ylsulfanyl)-benzamide; N-[(3R)-1-azabicyclo[2.2.2]oct-3-yl]-4-(2-chlorothiazol-5-ylsulfanyl)-benzamide; N-[(3R)-1-azabicyclo[2.2.2]oct-3-yl]-4-(2-methoxythiazol-5-ylsulfanyl)-benzamide; N-[(3R)-1-azabicyclo[2.2.2]oct-3-yl]-4-(2-trifluoromethylthiazol-5-ylsulfanyl)-benzamide; N-[(3R)-1-azabicyclo[2.2.2]oct-3-yl]-4-(2-acetylthiazol-5-ylsulfanyl )-benzamide; N-[(3R)-1-azabicyclo[2.2.2]oct-3-yl]-4-(2-acetaminothiazol-5-ylsulfanyl)-benzamide; N-[(3R)-1-azabicyclo[2.2.2]oct-3-yl]-4-(2-cyanothiazol-5-ylsulfanyl)-benzamide; N-[(3R)-1-azabicyclo[2.2.2]oct-3-yl]-4-(2-morpholin-4-yl-thiazol-5-ylsulfanyl)-benzamide; N-[(3R)-1-azabicyclo[2.2.2]oct-3-yl]-4-([1,3,4]oxadiazol-2-ylsulfanyl)-benzamide; N-[(3R)-1-azabicyclo[2.2.2]oct-3-yl]-4-(5-methyl[1,3,4]oxadiazol-2-ylsulfanyl)-benzamide; N-[(3R)-1-azabicyclo[2.2.2]oct-3-yl]-4-(5-chloro[1,3,4]oxadiazol-2-ylsulfanyl)-benzamide; N-[(3R)-1-azabicyclo[2.2.2]oct-3-yl]-4-(5-methoxy[1,3,4]oxadiazol-2-ylsulfanyl)-benzamide; N-[(3R)-1-azabicyclo[2.2.2]oct-3-yl]-4-(5-trifluoromethyl[1,3,4]oxadiazol-2-ylsulfanyl)-benzamide; N-[(3R)-1-azabicyclo[2.2.2]oct-3-yl]-4-(5-acetyl[1,3,4]oxadiazol-2-ylsulfanyl)-benzamide; N-[(3R)-1-azabicyclo[2.2.2]oct-3-yl]-4-(5-acetamino[1,3,4]oxadiazol-2-ylsulfanyl)-benzamide; N-[(3R)-1-azabicyclo[2.2.2]oct-3-yl]-4-(5-cyano[1,3,4]oxadiazol-2-ylsulfanyl)-benzamide; N-[(3R)-1-azabicyclo[2.2.2]oct-3-yl]-4-(5-morpholin-4-yl-[1,3,4]oxadiazol-2-ylsulfanyl)-benzamide; N-[(3R)-1-azabicyclo[2.2.2]oct-3-yl]-4-([1,3,4]thiadiazol-2-ylsulfanyl)-benzamide; N-[(3R)-1-azabicyclo[2.2.2]oct-3-yl]-4-(5-methyl[1,3,4]thiadiazol-2-ylsulfanyl)-benzamide; N-[(3R)-1-azabicyclo[2.2.2]oct-3-yl]-4-(5-chloro[1,3,4]thiadiazol-2-ylsulfanyl)-benzamide; N-[(3R)-1-azabicyclo[2.2.2]oct-3-yl]-4-(5-methoxy[1,3,4]thiadiazol-2-ylsulfanyl)-benzamide; N-[(3R)-1-azabicyclo[2.2.2]oct-3-yl]-4-(5-trifluoromethyl[1,3,4]thiadiazol-2-ylsulfanyl)-benzamide; N-[(3R)-1-azabicyclo[2.2.2]oct-3-yl]-4-(5-acetyl[1,3,4]thiadiazol-2-ylsulfanyl)-benzamide; N-[(3R)-1- azabicyclo[2.2.2]oct-3-yl]-4-(5-acetamino[1,3,4]thiadiazol-2-ylsulfanyl)-benzamide; N-[(3R)-1-azabicyclo[2.2.2]oct-3-yl]-4-(5-cyano[1,3,4]thiadiazol-2-ylsulfanyl)-benzamide; N-[(3R)-1-azabicyclo[2.2.2]oct-3-yl]-4-(5-morpholin-4-yl-[1,3,4]thiadiazol-2-ylsulfanyl)-benzamide; N-[(3R)-1-azabicyclo[2.2.2]oct-3-yl]-4-(pyrrol-2-yloxy)-benzamide; N-[(3R)-1-azabicyclo[2.2.2]oct-3-yl]-4-(5-methylpyrrolrrol-2-yloxy)-benzamide; N-[(3R)-1-azabicyclo[2.2.2]oct-3-yl]-4-(5-chloropyrrol-2-yloxy)-benzamide; N-[(3R)-1-azabicyclo[2.2.2]oct-3-yl]-4-(5-methoxypyrrol-2-yloxy)-benzamide; N-[(3R)-1-azabicyclo[2.2.2]oct-3-yl]-4-(5-trifluoromethylpyrrolrrol-2-yloxy)-benzamide; N-[(3R)-1-azabicyclo[2.2.2]oct-3-yl]-4-(5-acetylpyrrol-2-yloxy)-benzamide; N-[(3R)-1-azabicyclo[2.2.2]oct-3-yl]-4-(5-acetaminopyrrol-2-yloxy)-benzamide; N-[(3R)-1-azabicyclo[2.2.2]oct-3-yl]-4-(5-cyanopyrrol-2-yloxy)-benzamide; N-[(3R)-1-azabicyclo[2.2.2]oct-3-yl]-4-(5-morpholin-4-yl-pyrrol-2-yloxy)-benzamide; N-[(3R)-1-azabicyclo[2.2.2]oct-3-yl]-4-(3H-imidazol-4-yloxy)-benzamide; N-[(3R)-1-azabicyclo[2.2.2]oct-3-yl]-4-(2-methyl-3H-imidazol-4-yloxy)-benzamide; N-[(3R)-1-azabicyclo[2.2.2]oct-3-yl]-4-(2-chloro-3H-imidazol-4-yloxy)-benzamide; N-[(3R)-1-azabicyclo[2.2.2]oct-3-yl]-4-(2-methoxy-3H-imidazol-4-yloxy)-benzamide; N-[(3R)-1-azabicyclo[2.2.2]oct-3-yl]-4-(2-trifluoromethyl-3H-imidazol-4-yloxy)-benzamide; N-[(3R)-1-azabicyclo[2.2.2]oct-3-yl]-4-(2-acetyl-3H-imidazol-4-yloxy)-benzamide; N-[(3R)-1-azabicyclo[2.2.2]oct-3-yl]-4-(2-acetamino-3H-imidazol-4-yloxy)-benzamide; N-[(3R)-1-azabicyclo[2.2.2]oct-3-yl]-4-(2-cyano-3H-imidazol-4-yloxy)-benzamide; N-[(3R)-1-azabicyclo[2.2.2]oct-3-yl]-4-(2-morpholin-4-yl-3H-imidazol-4-yloxy)-benzamide; N-[(3R)-1-azabicyclo[2.2.2]oct-3-yl]-4-(isoxazol-2-yloxy)-benzamide; N-[(3R)-1-azabicyclo[2.2.2]oct-3-yl]-4-(5-methylisoxazol-3-yloxy)-benzamide; N-[(3R)-1-azabicyclo[2.2.2]oct-3-yl]-4-(5-chloroisoxazol-3-yloxy)-benzamide; N-[(3R)-1-azabicyclo[2.2.2]oct-3-yl]-4-(5-methoxyisoxazol-3-yloxy)-benzamide; N-[(3R)-1-azabicyclo[2.2.2]oct-3-yl]-4-(5-trifluoromethylisoxazol-3-yloxy)-benzamide; N-[(3R)-1-azabicyclo[2.2.2]oct-3-yl]-4-(5-acetylisoxazol-3-yloxy)-benzamide; N-[(3R)-1-azabicyclo[2.2.2]oct-3-yl]-4-(5-acetaminoisoxazol-3-yloxy)-benzamide; N-[(3R)-1-azabicyclo[2.2.2]oct-3-yl]-4-(5-cyanoisoxazol-3-yloxy)-benzamide; N-[(3R)-1-azabicyclo[2.2.2]oct-3-yl]-4-(5-morpholin-4-yl-isoxazol-3-yloxy)-benzamide; N-[(3R)-1-azabicyclo[2.2.2]oct-3-yl]-4-(isothiazol-2-yloxy)-benzamide; N-[(3R)-1-azabicyclo[2.2.2]oct-3-yl]-4-(5-methyl-isothiazol-3-yloxy)-benzamide; N-[(3R)-1-azabicyclo[2.2.2]oct-3-yl]-4-(5-chloroisothiazol-3-yloxy)-benzamide; N-[(3R)-1-azabicyclo[2.2.2]oct-3-yl]-4-(5-methoxyisothiazol-3-yloxy)-benzamide; N-[(3R)-1-azabicyclo[2.2.2]oct-3-yl]-4-(5-trifluoromethyl-isothiazol-3-yloxy)-benzamide; N-[(3R)-1-azabicyclo[2.2.2]oct-3-yl]-4-(5-acetyl-isothiazol-3-yloxy)-benzamide; N-[(3R)-1-azabicyclo[2.2.2]oct-3-yl]-4-(5-acetaminoisothiazol-3-yloxy)-benzamide; N-[(3R)-1-azabicyclo[2.2.2]oct-3-yl]-4-(5-cyanoisothiazol-3-yloxy)-benzamide; N-[(3R)-1-azabicyclo[2.2.2]oct-3-yl]-4-(5-morpholin-4-yl-isothiazol-3-yloxy)-benzamide; N-[(3R)-1-azabicyclo[2.2.2]oct-3-yl]-4-(pyrrol-2-ylsulfanyl)-benzamide; N-[(3R)-1-azabicyclo[2.2.2]oct-3-yl]-4-(5-methylpyrrolrrol-2-ylsulfanyl)-benzamide; N-[(3R)-1-azabicyclo[2.2.2]oct-3-yl]-4-(5-chloropyrrol-2-ylsulfanyl)-benzamide; N-[(3R)-1-azabicyclo[2.2.2]oct-3-yl]-4-(5-methoxypyrrol-2-ylsulfanyl)-benzamide; N-[(3R)-1-azabicyclo[2.2.2]oct-3-yl]-4-(5-trifluoromethylpyrrolrrol-2-ylsulfanyl)-benzamide; N-[(3R)-1-azabicyclo[2.2.2]oct-3-yl]-4-(5-acetylpyrrol-2-ylsulfanyl)-benzamide; N-[(3R)-1-azabicyclo[2.2.2]oct-3-yl]-4-(5-acetaminopyrrol-2-ylsulfanyl)-benzamide; N-[(3R)-1-azabicyclo[2.2.2]oct-3-yl]-4-(5-cyanopyrrol-2-ylsulfanyl)-benzamide; N-[(3R)-1-azabicyclo[2.2.2]oct-3-yl]-4-(5-morpholin-4-yl-pyrrol-2-ylsulfanyl)-benzamide; N-[(3R)-1-azabicyclo[2.2.2]oct-3-yl]-4-(3H-imidazol-4-ylsulfanyl)-benzamide; N-[(3R)-1-azabicyclo[2.2.2]oct-3-yl]-4-(2-methyl-3H-imidazol-4-ylsulfanyl)-benzamide; N-[(3R)-1-azabicyclo[2.2.2]oct-3-yl]-4-(2-chloro-3H-imidazol-4-ylsulfanyl)-benzamide; N-[(3R)-1-azabicyclo[2.2.2]oct-3-yl]-4-(2-methoxy-3H-imidazol-4-ylsulfanyl)-benzamide; N-[(3R)-1-azabicyclo[2.2.2]oct-3-yl]-4-(2-trifluoromethyl-3H-imidazol-4-ylsulfanyl)-benzamide; N-[(3R)-1-azabicyclo[2.2.2]oct-3-yl]-4-(2-acetyl-3H-imidazol-4-ylsulfanyl)-benzamide; N-[(3R)-1-azabicyclo[2.2.2]oct-3-yl]-4-(2-acetamino-3H-imidazol-4-ylsulfanyl)-benzamide; N-[(3R)-1-azabicyclo[2.2.2]oct-3-yl]-4-(2-cyano-3H-imidazol-4-ylsulfanyl)-benzamide; N-[(3R)-1-azabicyclo[2.2.2]oct-3-yl]-4-(2-morpholin-4-yl-3H-imidazol-4-ylsulfanyl)-benzamide; N-[(3R)-1-azabicyclo[2.2.2]oct-3-yl]-4-(isoxazol-2-ylsulfanyl)-benzamide; N-[(3R)-1-azabicyclo[2.2.2]oct-3-yl]-4-(5-methylisoxazol-3-ylsulfanyl)-benzamide; N-[(3R)-1-azabicyclo[2.2.2]oct-3-yl]-4-(5-chloroisoxazol-3-ylsulfanyl)-benzamide; N-[(3R)-1-azabicyclo[2.2.2]oct-3-yl]-4-(5-methoxyisoxazol-3-ylsulfanyl)-benzamide; N-[(3R)-1-azabicyclo[2.2.2]oct-3-yl]-4-(5-trifluoromethylisoxazol-3-ylsulfanyl)-benzamide; N-[(3R)-1-azabicyclo[2.2.2]oct-3-yl]-4-(5-acetylisoxazol-3-ylsulfanyl)-benzamide; N-[(3R)-1-azabicyclo[2.2.2]oct-3-yl]-4-(5-acetaminoisoxazol-3-ylsulfanyl)-benzamide; N-[(3R)-1-azabicyclo[2.2.2]oct-3-yl]-4-(5-cyanoisoxazol-3-ylsulfanyl)-benzamide; N-[(3R)-1-azabicyclo[2.2.2]oct-3-yl]-4-(5-morpholin-4-yl-isoxazol-3-ylsulfanyl)-benzamide; N-[(3R)-1-azabicyclo[2.2.2]oct-3-yl]-4-(isothiazol-2-ylsulfanyl)-benzamide; N-[(3R)-1-azabicyclo[2.2.2]oct-3-yl]-4-(5-methyl-isothiazol-3-ylsulfanyl)-benzamide; N-[(3R)-1-azabicyclo[2.2.2]oct-3-yl]-4-(5-chloroisothiazol-3-ylsulfanyl)-benzamide; N-[(3R)-1-azabicyclo[2.2.2]oct-3-yl]-4-(5-methoxyisothiazol-3-ylsulfanyl)-benzamide; N-[(3R)-1-azabicyclo[2.2.2]oct-3-yl]-4-(5-trifluoromethyl-isothiazol-3-ylsulfanyl)-benzamide; N-[(3R)-1-azabicyclo[2.2.2]oct-3-yl]-4-(5-acetyl-isothiazol-3-ylsulfanyl)-benzamide; N-[(3R)-1-azabicyclo[2.2.2]oct-3-yl]-4-(5-acetaminoisothiazol-3-ylsulfanyl)-benzamide; N-[(3R)-1-azabicyclo[2.2.2]oct-3-yl]-4-(5-cyanoisothiazol-3-ylsulfanyl)-benzamide; N-[(3R)-1-azabicyclo[2.2.2]oct-3-yl]-4-(5-morpholin-4-yl-isothiazol-3-ylsulfanyl)-benzamide; N-[(3R)-1-azabicyclo[2.2.2]oct-3-yl]-4-(6-methylpyrrolridin-3-yloxy)-benzamide; N-[(3R)-1-azabicyclo[2.2.2]oct-3-yl]-4-(6--chloropyridin-3-yloxy)-benzamide; N-[(3R)-1-azabicyclo[2.2.2]oct-3-yl]-4-(6-methoxypyridin-3-yloxy)-benzamide; N-[(3R)-1-azabicyclo[2.2.2]oct-3-yl]-4-(6-trifluoromethylpyrrolridin-3-yloxy)-benzamide; N-[(3R)-1-azabicyclo[2.2.2]oct-3-yl]-4-(6- acetylpyridin-3-yloxy)-benzamide; N-[(3R)-1-azabicyclo[2.2.2]oct-3-yl]-4-(6-acetaminopyridin-3-yloxy)-benzamide; N-[(3R)-1-azabicyclo[2.2.2]oct-3-yl]-4-(6-cyanopyridin-3-yloxy)-benzamide; N-[(3R)-1-azabicyclo[2.2.2]oct-3-yl]-4-(6-morpholin-4-yl-pyridin-3-yloxy)-benzamide; N-[(3R)-1-azabicyclo[2.2.2]oct-3-yl]-4-(2-methylpyrrolridin-4-yloxy)-benzamide; N-[(3R)-1-azabicyclo[2.2.2]oct-3-yl]-4-(2--chloropyridin-4-yloxy)-benzamide; N-[(3R)-1-azabicyclo[2.2.2]oct-3-yl]-4-(2-methoxypyridin-4-yloxy)-benzamide; N-[(3R)-1-azabicyclo[2.2.2]oct-3-yl]-4-(2-trifluoromethylpyrrolridin-4-yloxy)-benzamide; N-[(3R)-1-azabicyclo[2.2.2]oct-3-yl]-4-(2-acetylpyridin-4-yloxy)-benzamide; N-[(3R)-1-azabicyclo[2.2.2]oct-3-yl]-4-(2-acetaminopyridin-4-yloxy)-benzamide; N-[(3R)-1-azabicyclo[2.2.2]oct-3-yl]-4-(2-cyanopyridin-4-yloxy)-benzamide; N-[(3R)-1-azabicyclo[2.2.2]oct-3-yl]-4-(2-morpholin-4-yl-pyridin-4-yloxy)-benzamide; N-[(3R)-1-azabicyclo[2.2.2]oct-3-yl]-4-(5-methylpyrrolridin-2-yloxy)-benzamide; N-[(3R)-1-azabicyclo[2.2.2]oct-3-yl]-4-(5--chloropyridin-2-yloxy)-benzamide; N-[(3R)-1-azabicyclo[2.2.2]oct-3-yl]-4-(5-methoxypyridin-2-yloxy)-benzamide; N-[(3R)-1-azabicyclo[2.2.2]oct-3-yl]-4-(5-trifluoromethylpyrrolridin-2-yloxy)-benzamide; N-[(3R)-1-azabicyclo[2.2.2]oct-3-yl]-4-(5-acetylpyridin-2-yloxy)-benzamide; N-[(3R)-1-azabicyclo[2.2.2]oct-3-yl]-4-(5-acetaminopyridin-2-yloxy)-benzamide; N-[(3R)-1-azabicyclo[2.2.2]oct-3-yl]-4-(5-cyanopyridin-2-yloxy)-benzamide; N-[(3R)-1-azabicyclo[2.2.2]oct-3-yl]-4-(5-morpholin-4-yl-pyridin-2-yloxy)-benzamide; N-[(3R)-1-azabicyclo[2.2.2]oct-3-yl]-4-(4-methylpyrrolridin-2-yloxy)-benzamide; N-[(3R)-1-azabicyclo[2.2.2]oct-3-yl]-4-(4--chloropyridin-2-yloxy)-benzamide; N-[(3R)-1-azabicyclo[2.2.2]oct-3-yl]-4-(4-methoxypyridin-2-yloxy)-benzamide; N-[(3R)-1-azabicyclo[2.2.2]oct-3-yl]-4-(4-trifluoromethylpyrrolridin-2-yloxy)-benzamide; N-[(3R)-1-azabicyclo[2.2.2]oct-3-yl]-4-(4-acetylpyridin-2-yloxy)-benzamide; N-[(3R)-1-azabicyclo[2.2.2]oct-3-yl]-4-(4-acetaminopyridin-2-yloxy)-benzamide; N-[(3R)-1-azabicyclo[2.2.2]oct-3-yl]-4-(4-cyanopyridin-2-yloxy)-benzamide; N-[(3R)-1-azabicyclo[2.2.2]oct-3-yl]-4-(4-morpholin-4-yl-pyridin-2-yloxy)-benzamide; N-[(3R)-1-azabicyclo[2.2.2]oct-3-yl]-4-(6-methylpyrrolridin-2-yloxy)-benzamide; N-[(3R)-1-azabicyclo[2.2.2]oct-3-yl]-4-(6--chloropyridin-2-yloxy)-benzamide; N-[(3R)-1-azabicyclo[2.2.2]oct-3-yl]-4-(6-methoxypyridin-2-yloxy)-benzamide; N-[(3R)-1-azabicyclo[2.2.2]oct-3-yl]-4-(6-trifluoromethylpyrrolridin-2-yloxy)-benzamide; N-[(3R)-1-azabicyclo[2.2.2]oct-3-yl]-4-(6--acetylpyridin-2-yloxy)-benzamide; N-[(3R)-1-azabicyclo[2.2.2]oct-3-yl]-4-(6-acetaminopyridin-2-yloxy)-benzamide; N-[(3R)-1-azabicyclo[2.2.2]oct-3-yl]-4-(6-cyanopyridin-2-yloxy)-benzamide; N-[(3R)-1-azabicyclo[2.2.2]oct-3-yl]-4-(6-morpholin-4-yl-pyridin-2-yloxy)-benzamide; N-[(3R)-1-azabicyclo[2.2.2]oct-3-yl]-4-(5-methylpyrrolridin-3-yloxy)-benzamide; N-[(3R)-1-azabicyclo[2.2.2]oct-3-yl]-4-(5--chloropyridin-3-yloxy)-benzamide; N-[(3R)-1-azabicyclo[2.2.2]oct-3-yl]-4-(5-methoxypyridin-3-yloxy)-benzamide; N-[(3R)-1-azabicyclo[2.2.2]oct-3-yl]-4-(5-trifluoromethylpyrrolridin-3-yloxy)-benzamide; N-[(3R)-1-azabicyclo[2.2.2]oct-3-yl]-4-(5-acetylpyridin-3-yloxy)-benzamide; N-[(3R)-1-azabicyclo[2.2.2]oct-3-yl]-4-(5-acetaminopyridin-3-yloxy)-benzamide; N-[(3R)-1-azabicyclo[2.2.2]oct-3-yl]-4-(5-cyanopyridin-3-yloxy)-benzamide; N-[(3R)-1-azabicyclo[2.2.2]oct-3-yl]-4-(5-morpholin-4-yl-pyridin-3-yloxy)-benzamide; N-[(3R)-1-azabicyclo[2.2.2]oct-3-yl]-4-(2--chloropyridin-3-yloxy)-benzamide; N-[(3R)-1-azabicyclo[2.2.2]oct-3-yl]-4-(4--chloropyridin-3-yloxy)-benzamide; N-[(3R)-1-azabicyclo[2.2.2]oct-3-yl]-4-(3--chloropyridin-4-yloxy)-benzamide; N-[(3R)-1-azabicyclo[2.2.2]oct-3-yl]-4-(3--chloropyridin-2-yloxy)-benzamide; N-[(3R)-1-azabicyclo[2.2.2]oct-3-yl]-4-(6-methylpyrrolridin-3-ylsulfanyl)-benzamide; N-[(3R)-1-azabicyclo[2.2.2]oct-3-yl]-4-(6--chloropyridin-3-ylsulfanyl)-benzamide; N-[(3R)-1-azabicyclo[2.2.2]oct-3-yl]-4-(6-methoxypyridin-3-ylsulfanyl)-benzamide; N-[(3R)-1-azabicyclo[2.2.2]oct-3-yl]-4-(6-trifluoromethylpyrrolridin-3-ylsulfanyl)-benzamide; N-[(3R)-1-azabicyclo[2.2.2]oct-3-yl]-4-(6-acetylpyridin-3-ylsulfanyl)-benzamide; N-[(3R)-1-azabicyclo[2.2.2]oct-3-yl]-4-(6-acetaminopyridin-3-ylsulfanyl)-benzamide; N-[(3R)-1-azabicyclo[2.2.2]oct-3-yl]-4-(6-cyanopyridin-3-ylsulfanyl)-benzamide; N-[(3R)-1-azabicyclo[2.2.2]oct-3-yl]-4-(6-morpholin-4-yl-pyridin-3-ylsulfanyl)-benzamide; N-[(3R)-1-azabicyclo[2.2.2]oct-3-yl]-4-(2-methylpyrrolridin-4-ylsulfanyl)-benzamide; N-[(3R)-1-azabicyclo[2.2.2]oct-3-yl]-4-(2--chloropyridin-4-ylsulfanyl)-benzamide; N-[(3R)-1-azabicyclo[2.2.2]oct-3-yl]-4-(2-methoxypyridin-4-ylsulfanyl)-benzamide; N-[(3R)-1-azabicyclo[2.2.2]oct-3-yl]-4-(2-trifluoromethylpyrrolridin-4-ylsulfanyl)-benzamide; N-[(3R)-1-azabicyclo[2.2.2]oct-3-yl]-4-(2-acetylpyridin-4-ylsulfanyl)-benzamide; N-[(3R)-1-azabicyclo[2.2.2]oct-3-yl]-4-(2-acetaminopyridin-4-ylsulfanyl)-benzamide; N-[(3R)-1-azabicyclo[2.2.2]oct-3-yl]-4-(2-cyanopyridin-4-ylsulfanyl)-benzamide; N-[(3R)-1-azabicyclo[2.2.2]oct-3-yl]-4-(2-morpholin-4-yl-pyridin-4-ylsulfanyl)-benzamide; N-[(3R)-1-azabicyclo[2.2.2]oct-3-yl]-4-(5-methylpyrrolridin-2-ylsulfanyl)-benzamide; N-[(3R)-1-azabicyclo[2.2.2]oct-3-yl]-4-(5--chloropyridin-2-ylsulfanyl)-benzamide; N-[(3R)-1-azabicyclo[2.2.2]oct-3-yl]-4-(5-methoxypyridin-2-ylsulfanyl)-benzamide; N-[(3R)-1-azabicyclo[2.2.2]oct-3-yl]-4-(5-trifluoromethylpyrrolridin-2-ylsulfanyl)-benzamide; N-[(3R)-1-azabicyclo[2.2.2]oct-3-yl]-4-(5-acetylpyridin-2-ylsulfanyl)-benzamide; N-[(3R)-1-azabicyclo[2.2.2]oct-3-yl]-4-(5-acetaminopyridin-2-ylsulfanyl)-benzamide; N-[(3R)-1-azabicyclo[2.2.2]oct-3-yl]-4-(5-cyanopyridin-2-ylsulfanyl)-benzamide; N-[(3R)-1-azabicyclo[2.2.2]oct-3-yl]-4-(5-morpholin-4-yl-pyridin-2-ylsulfanyl)-benzamide; N-[(3R)-1-azabicyclo[2.2.2]oct-3-yl]-4-(4-methylpyrrolridin-2-ylsulfanyl)-benzamide; N-[(3R)-1-azabicyclo[2.2.2]oct-3-yl]-4-(4--chloropyridin-2-ylsulfanyl)-benzamide; N-[(3R)-1-azabicyclo[2.2.2]oct-3-yl]-4-(4-methoxypyridin-2-ylsulfanyl)-benzamide; N-[(3R)-1-azabicyclo[2.2.2]oct-3-yl]-4-(4-trifluoromethylpyrrolridin-2-ylsulfanyl)-benzamide; N-[(3R)-1-azabicyclo[2.2.2]oct-3-yl]-4-(4-acetylpyridin-2-ylsulfanyl)-benzamide; N-[(3R)-1-azabicyclo[2.2.2]oct-3-yl]-4-(4-acetaminopyridin-2-ylsulfanyl)-benzamide; N-[(3R)-1-azabicyclo[2.2.2]oct-3-yl]-4-(4-cyanopyridin-2-ylsulfanyl)-benzamide; N-[(3R)-1-azabicyclo[2.2.2]oct-3-yl]-4-(4-morpholin-4-yl-pyridin-2-ylsulfanyl)-benzamide; N-[(3R)-1-azabicyclo[2.2.2]oct-3-yl]-4-(6-methylpyrrolridin-2- ylsulfanyl)-benzamide; N-[(3R)-1-azabicyclo[2.2.2]oct-3-yl]-4-(6-chloropyridin-2-ylsulfanyl)-benzamide; N-[(3R)-1-azabicyclo[2.2.2]oct-3-yl]-4-(6-methoxypyridin-2-ylsulfanyl)-benzamide; N-[(3R)-1-azabicyclo[2.2.2]oct-3-yl]-4-(6-trifluoromethylpyrrolridin-2-ylsulfanyl)-benzamide; N-[(3R)-1-azabicyclo[2.2.2]oct-3-yl]-4-(6-acetylpyridin-2-ylsulfanyl)-benzamide; N-[(3R)-1-azabicyclo[2.2.2]oct-3-yl]-4-(6-acetaminopyridin-2-ylsulfanyl)-benzamide; N-[(3R)-1-azabicyclo[2.2.2]oct-3-yl]-4-(6-cyanopyridin-2-ylsulfanyl)-benzamide; N-[(3R)-1-azabicyclo[2.2.2]oct-3-yl]-4-(6-morpholin-4-yl-pyridin-2-ylsulfanyl)-benzamide; N-[(3R)-1-azabicyclo[2.2.2]oct-3-yl]-4-(5-methylpyrrolridin-3-ylsulfanyl)-benzamide; N-[(3R)-1-azabicyclo[2.2.2]oct-3-yl]-4-(5--chloropyridin-3-ylsulfanyl)-benzamide; N-[(3R)-1-azabicyclo[2.2.2]oct-3-yl]-4-(5-methoxypyridin-3-ylsulfanyl)-benzamide; N-[(3R)-1-azabicyclo[2.2.2]oct-3-yl]-4-(5-trifluoromethylpyrrolridin-3-ylsulfanyl)-benzamide; N-[(3R)-1-azabicyclo[2.2.2]oct-3-yl]-4-(5-acetylpyridin-3-ylsulfanyl)-benzamide; N-[(3R)-1-azabicyclo[2.2.2]oct-3-yl]-4-(5-acetaminopyridin-3-ylsulfanyl)-benzamide; N-[(3R)-1-azabicyclo[2.2.2]oct-3-yl]-4-(5-cyanopyridin-3-ylsulfanyl)-benzamide; N-[(3R)-1-azabicyclo[2.2.2]oct-3-yl]-4-(5-morpholin-4-yl-pyridin-3-ylsulfanyl)-benzamide; N-[(3R)-1-azabicyclo[2.2.2]oct-3-yl]-4-(2--chloropyridin-3-ylsulfanyl)-benzamide; N-[(3R)-1-azabicyclo[2.2.2]oct-3-yl]-4-(4--chloropyridin-3-ylsulfanyl)-benzamide; N-[(3R)-1-azabicyclo[2.2.2]oct-3-yl]-4-(3--chloropyridin-4-ylsulfanyl)-benzamide; N-[(3R)-1-azabicyclo[2.2.2]oct-3-yl]-4-(3--chloropyridin-2-ylsulfanyl)-benzamide; N-[(2S,3R)-2-methyl-1-azabicyclo[2.2.2]oct-3-yl]-4-(4-aminophenoxy)-benzamide; N-[(2S,3R)-2-methyl-1-azabicyclo[2.2.2]oct-3-yl]-4-(3-aminophenoxy)-benzamide; N-[(2S,3R)-2-methyl-1-azabicyclo[2.2.2]oct-3-yl]-4-(2-aminophenoxy)-benzamide; N-[(2S,3R)-2-methyl-1-azabicyclo[2.2.2]oct-3-yl]-4-(4-methanesulfonylamino-phenoxy)-benzamide; N-[(2S,3R)-2-methyl-1-azabicyclo[2.2.2]oct-3-yl]-4-(3-methanesulfonylamino-phenoxy)-benzamide; N-[(2S,3R)-2-methyl-1-azabicyclo[2.2.2]oct-3-yl]-4-(2-methanesulfonylamino-phenoxy)-benzamide; N-[(2S,3R)-2-methyl-1-azabicyclo[2.2.2]oct-3-yl]-4-(4-acetoxyphenoxy)-benzamide; N-[(2S,3R)-2-methyl-1-azabicyclo[2.2.2]oct-3-yl]-4-(3-acetoxyphenoxy)-benzamide; N-[(2S,3R)-2-methyl-1-azabicyclo[2.2.2]oct-3-yl]-4-(2-acetoxyphenoxy)-benzamide; N-[(2S,3R)-2-methyl-1-azabicyclo[2.2.2]oct-3-yl]-4-(4-acetylphenoxy)-benzamide; N-[(2S,3R)-2-methyl-1-azabicyclo[2.2.2]oct-3-yl]-4-(3-acetylphenoxy)-benzamide; N-[(2S,3R)-2-methyl-1-azabicyclo[2.2.2]oct-3-yl]-4-(2-acetylphenoxy)-benzamide; N-[(2S,3R)-2-methyl-1-azabicyclo[2.2.2]oct-3-yl]-4-(4-carbamoylphenoxy)-benzamide; N-[(2S,3R)-2-methyl-1-azabicyclo[2.2.2]oct-3-yl]-4-(3-carbamoylphenoxy)-benzamide; N-[(2S,3R)-2-methyl-1-azabicyclo[2.2.2]oct-3-yl]-4-(2-carbamoylphenoxy)-benzamide; N-[(2S,3R)-2-methyl-1-azabicyclo[2.2.2]oct-3-yl]-4-(4-cyanophenoxy)-benzamide; N-[(2S,3R)-2-methyl-1-azabicyclo[2.2.2]oct-3-yl]-4-(3-cyanophenoxy)-benzamide; N-[(2S,3R)-2-methyl-1-azabicyclo[2.2.2]oct-3-yl]-4-(2-cyanophenoxy)-benzamide; N-[(2S,3R)-2-methyl-1-azabicyclo[2.2.2]oct-3-yl]-4-(4-sulfamoylphenoxy)-benzamide; N-[(2S,3R)-2-methyl-1-azabicyclo[2.2.2]oct-3-yl]-4-(3-sulfamoylphenoxy)-benzamide; N-[(2S,3R)-2-methyl-1-azabicyclo[2.2.2]oct-3-yl]-4-(2-sulfamoylphenoxy)-benzamide; N-[(2S,3R)-2-methyl-1-azabicyclo[2.2.2]oct-3-yl]-4-(thiophen-2-yloxy)-benzamide; N-[(2S,3R)-2-methyl-1-azabicyclo[2.2.2]oct-3-yl]-4-(5-methy-thiophen-2-yloxy)-benzamide; N-[(2S,3R)-2-methyl-1-azabicyclo[2.2.2]oct-3-yl]-4-(5-chlorothiophen-2-yloxy)-benzamide; N-[(2S,3R)-2-methyl-1-azabicyclo[2.2.2]oct-3-yl]-4-(5-methoxythiophen-2-yloxy)-benzamide; N-[(2S,3R)-2-methyl-1-azabicyclo[2.2.2]oct-3-yl]-4-(5-trifluoromethy-thiophen-2-yloxy)-benzamide; N-[(2S,3R)-2-methyl-1-azabicyclo[2.2.2]oct-3-yl]-4-(5-acety-thiophen-2-yloxy)-benzamide; N-[(2S,3R)-2-methyl-1-azabicyclo[2.2.2]oct-3-yl]-4-(5-acetaminothiophen-2-yloxy)-benzamide; N-[(2S,3R)-2-methyl-1-azabicyclo[2.2.2]oct-3-yl]-4-(5-cyanothiophen-2-yloxy)-benzamide; N-[(2S,3R)-2-methyl-1-azabicyclo[2.2.2]oct-3-yl]-4-(5-morpholin-4-yl-thiophen-2-yloxy)-benzamide; N-[(2S,3R)-2-methyl-1-azabicyclo[2.2.2]oct-3-yl]-4-(4-methy-thiophen-2-yloxy)-benzamide; N-[(2S,3R)-2-methyl-1-azabicyclo[2.2.2]oct-3-yl]-4-(4-chlorothiophen-2-yloxy)-benzamide; N-[(2S,3R)-2-methyl-1-azabicyclo[2.2.2]oct-3-yl]-4-(4-methoxythiophen-2-yloxy)-benzamide; N-[(2S,3R)-2-methyl-1-azabicyclo[2.2.2]oct-3-yl]-4-(4-trifluoromethy-thiophen-2-yloxy)-benzamide; N-[(2S,3R)-2-methyl-1-azabicyclo[2.2.2]oct-3-yl]-4-(4-acety-thiophen-2-yloxy)-benzamide; N-[(2S,3R)-2-methyl-1-azabicyclo[2.2.2]oct-3-yl]-4-(4-acetaminothiophen-2-yloxy)-benzamide; N-[(2S,3R)-2-methyl-1-azabicyclo[2.2.2]oct-3-yl]-4-(4-cyanothiophen-2-yloxy)-benzamide; N-[(2S,3R)-2-methyl-1-azabicyclo[2.2.2]oct-3-yl]-4-(4-morpholin-4-yl-thiophen-2-yloxy)-benzamide; N-[(2S,3R)-2-methyl-1-azabicyclo[2.2.2]oct-3-yl]-4-(furan-2-yloxy)-benzamide; N-[(2S,3R)-2-methyl-1-azabicyclo[2.2.2]oct-3-yl]-4-(5-methylfuran-2-yloxy)-benzamide; N-[(2S,3R)-2-methyl-1-azabicyclo[2.2.2]oct-3-yl]-4-(5-chlorofuran-2-yloxy)-benzamide; N-[(2S,3R)-2-methyl-1-azabicyclo[2.2.2]oct-3-yl]-4-(5-methoxyfuran-2-yloxy)-benzamide; N-[(2S,3R)-2-methyl-1-azabicyclo[2.2.2]oct-3-yl]-4-(5-trifluoromethylfuran-2-yloxy)-benzamide; N-[(2S,3R)-2-methyl-1-azabicyclo[2.2.2]oct-3-yl]-4-(5-acetylfuran-2-yloxy)-benzamide; N-[(2S,3R)-2-methyl-1-azabicyclo[2.2.2]oct-3-yl]-4-(5-acetaminofuran-2-yloxy)-benzamide; N-[(2S,3R)-2-methyl-1-azabicyclo[2.2.2]oct-3-yl]-4-(5-cyanofuran-2-yloxy)-benzamide; N-[(2S,3R)-2-methyl-1-azabicyclo[2.2.2]oct-3-yl]-4-(5-morpholin-4-yl-furan-2-yloxy)-benzamide; N-[(2S,3R)-2-methyl-1-azabicyclo[2.2.2]oct-3-yl]-4-(4-methylfuran-2-yloxy)-benzamide; N-[(2S,3R)-2-methyl-1-azabicyclo[2.2.2]oct-3-yl]-4-(4-chlorofuran-2-yloxy)-benzamide; N-[(2S,3R)-2-methyl-1-azabicyclo[2.2.2]oct-3-yl]-4-(4-methoxyfuran-2-yloxy)-benzamide; N-[(2S,3R)-2-methyl-1-azabicyclo[2.2.2]oct-3-yl]-4-(4-trifluoromethylfuran-2-yloxy)-benzamide; N-[(2S,3R)-2-methyl-1-azabicyclo[2.2.2]oct-3-yl]-4-(4-acetylfuran-2-yloxy)-benzamide; N-[(2S,3R)-2-methyl-1-azabicyclo[2.2.2]oct-3-yl]-4-(4-acetaminofuran-2-yloxy)-benzamide; N-[(2S,3R)-2-methyl-1-azabicyclo[2.2.2]oct-3-yl]-4-(4-cyanofuran-2-yloxy)-benzamide; N-[(2S,3R)-2-methyl-1-azabicyclo[2.2.2]oct-3-yl]-4-(4-morpholin-4-yl-furan-2-yloxy)-benzamide; N-[(2S,3R)-2-methyl-1- azabicyclo[2.2.2]oct-3-yl]-4-(oxazol-2-yloxy)-benzamide; N-[(2S,3R)-2-methyl-1-azabicyclo[2.2.2]oct-3-yl]-4-(5-methyloxazol-2-yloxy)-benzamide; N-[(2S,3R)-2-methyl-1-azabicyclo[2.2.2]oct-3-yl]-4-(5-chlorooxazol-2-yloxy)-benzamide; N-[(2S,3R)-2-methyl-1-azabicyclo[2.2.2]oct-3-yl]-4-(5-methoxyoxazol-2-yloxy)-benzamide; N-[(2S,3R)-2-methyl-1-azabicyclo[2.2.2]oct-3-yl]-4-(5-trifluoromethyloxazol-2-yloxy)-benzamide; N-[(2S,3R)-2-methyl-1-azabicyclo[2.2.2]oct-3-yl]-4-(5-acetyloxazol-2-yloxy)-benzamide; N-[(2S,3R)-2-methyl-1-azabicyclo[2.2.2]oct-3-yl]-4-(5-acetaminooxazol-2-yloxy)-benzamide; N-[(2S,3R)-2-methyl-1-azabicyclo[2.2.2]oct-3-yl]-4-(5-cyanooxazol-2-yloxy)-benzamide; N-[(2S,3R)-2-methyl-1-azabicyclo[2.2.2]oct-3-yl]-4-(5-morpholin-4-yl-oxazol-2-yloxy)-benzamide; N-[(2S,3R)-2-methyl-1-azabicyclo[2.2.2]oct-3-yl]-4-(oxazol-2-yloxy)-benzamide; N-[(2S,3R)-2-methyl-1-azabicyclo[2.2.2]oct-3-yl]-4-(4-methyloxazol-2-yloxy)-benzamide; N-[(2S,3R)-2-methyl-1-azabicyclo[2.2.2]oct-3-yl]-4-(4-chlorooxazol-2-yloxy)-benzamide; N-[(2S,3R)-2-methyl-1-azabicyclo[2.2.2]oct-3-yl]-4-(4-methoxyoxazol-2-yloxy)-benzamide; N-[(2S,3R)-2-methyl-1-azabicyclo[2.2.2]oct-3-yl]-4-(4-trifluoromethyloxazol-2-yloxy)-benzamide; N-[(2S,3R)-2-methyl-1-azabicyclo[2.2.2]oct-3-yl]-4-(4-acetyloxazol-2-yloxy)-benzamide; N-[(2S,3R)-2-methyl-1-azabicyclo[2.2.2]oct-3-yl]-4-(4-acetaminooxazol-2-yloxy)-benzamide; N-[(2S,3R)-2-methyl-1-azabicyclo[2.2.2]oct-3-yl]-4-(4-cyanooxazol-2-yloxy)-benzamide; N-[(2S,3R)-2-methyl-1-azabicyclo[2.2.2]oct-3-yl]-4-(4-morpholin-4-yl-oxazol-2-yloxy)-benzamide; N-[(2S,3R)-2-methyl-1-azabicyclo[2.2.2]oct-3-yl]-4-(oxazol-5-yloxy)-benzamide; N-[(2S,3R)-2-methyl-1-azabicyclo[2.2.2]oct-3-yl]-4-(2-methyloxazol-5-yloxy)-benzamide; N-[(2S,3R)-2-methyl-1-azabicyclo[2.2.2]oct-3-yl]-4-(2-chlorooxazol-5-yloxy)-benzamide; N-[(2S,3R)-2-methyl-1-azabicyclo[2.2.2]oct-3-yl]-4-(2-methoxyoxazol-5-yloxy)-benzamide; N-[(2S,3R)-2-methyl-1-azabicyclo[2.2.2]oct-3-yl]-4-(2-trifluoromethyloxazol-5-yloxy)-benzamide; N-[(2S,3R)-2-methyl-1-azabicyclo[2.2.2]oct-3-yl]-4-(2-acetyloxazol-5-yloxy)-benzamide; N-[(2S,3R)-2-methyl-1-azabicyclo[2.2.2]oct-3-yl]-4-(2-acetaminooxazol-5-yloxy)-benzamide; N-[(2S,3R)-2-methyl-1-azabicyclo[2.2.2]oct-3-yl]-4-(2-cyanooxazol-5-yloxy)-benzamide; N-[(2S,3R)-2-methyl-1-azabicyclo[2.2.2]oct-3-yl]-4-(2-morpholin-4-yl-oxazol-5-yloxy)-benzamide; N-[(2S,3R)-2-methyl-1-azabicyclo[2.2.2]oct-3-yl]-4-(thiazol-2-yloxy)-benzamide; N-[(2S,3R)-2-methyl-1-azabicyclo[2.2.2]oct-3-yl]-4-(5-methylthiazol-2-yloxy)-benzamide; N-[(2S,3R)-2-methyl-1-azabicyclo[2.2.2]oct-3-yl]-4-(5-chlorothiazol-2-yloxy)-benzamide; N-[(2S,3R)-2-methyl-1-azabicyclo[2.2.2]oct-3-yl]-4-(5-methoxythiazol-2-yloxy)-benzamide; N-[(2S,3R)-2-methyl-1-azabicyclo[2.2.2]oct-3-yl]-4-(5-trifluoromethylthiazol-2-yloxy)-benzamide; N-[(2S,3R)-2-methyl-1-azabicyclo[2.2.2]oct-3-yl]-4-(5-acetylthiazol-2-yloxy)-benzamide; N-[(2S,3R)-2-methyl-1-azabicyclo[2.2.2]oct-3-yl]-4-(5-acetaminothiazol-2-yloxy)-benzamide; N-[(2S,3R)-2-methyl-1-azabicyclo[2.2.2]oct-3-yl]-4-(5-cyanothiazol-2-yloxy)-benzamide; N-[(2S,3R)-2-methyl-1-azabicyclo[2.2.2]oct-3-yl]-4-(5-morpholin-4-yl-thiazol-2-yloxy)-benzamide; N-[(2S,3R)-2-methyl-1-azabicyclo[2.2.2]oct-3-yl]-4-(thiazol-2-yloxy)-benzamide; N-[(2S,3R)-2-methyl-1-azabicyclo[2.2.2]oct-3-yl]-4-(4-methylthiazol-2-yloxy)-benzamide; N-[(2S,3R)-2-methyl-1-azabicyclo[2.2.2]oct-3-yl]-4-(4-chlorothiazol-2-yloxy)-benzamide; N-[(2S,3R)-2-methyl-1-azabicyclo[2.2.2]oct-3-yl]-4-(4-methoxythiazol-2-yloxy)-benzamide; N-[(2S,3R)-2-methyl-1-azabicyclo[2.2.2]oct-3-yl]-4-(4-trifluoromethylthiazol-2-yloxy)-benzamide; N-[(2S,3R)-2-methyl-1-azabicyclo[2.2.2]oct-3-yl]-4-(4-acetylthiazol-2-yloxy)-benzamide; N-[(2S,3R)-2-methyl-1-azabicyclo[2.2.2]oct-3-yl]-4-(4-acetaminothiazol-2-yloxy)-benzamide; N-[(2S,3R)-2-methyl-1-azabicyclo[2.2.2]oct-3-yl]-4-(4-cyanothiazol-2-yloxy)-benzamide; N-[(2S,3R)-2-methyl-1-azabicyclo[2.2.2]oct-3-yl]-4-(4-morpholin-4-yl-thiazol-2-yloxy)-benzamide; N-[(2S,3R)-2-methyl-1-azabicyclo[2.2.2]oct-3-yl]-4-(thiazol-5-yloxy)-benzamide; N-[(2S,3R)-2-methyl-1-azabicyclo[2.2.2]oct-3-yl]-4-(2-methylthiazol-5-yloxy)-benzamide; N-[(2S,3R)-2-methyl-1-azabicyclo[2.2.2]oct-3-yl]-4-(2-chlorothiazol-5-yloxy)-benzamide; N-[(2S,3R)-2-methyl-1-azabicyclo[2.2.2]oct-3-yl]-4-(2-methoxythiazol-5-yloxy)-benzamide; N-[(2S,3R)-2-methyl-1-azabicyclo[2.2.2]oct-3-yl]-4-(2-trifluoromethylthiazol-5-yloxy)-benzamide; N-[(2S,3R)-2-methyl-1-azabicyclo[2.2.2]oct-3-yl]-4-(2-acetylthiazol-5-yloxy)-benzamide; N-[(2S,3R)-2-methyl-1-azabicyclo[2.2.2]oct-3-yl]-4-(2-acetaminothiazol-5-yloxy)-benzamide; N-[(2S,3R)-2-methyl-1-azabicyclo[2.2.2]oct-3-yl]-4-(2-cyanothiazol-5-yloxy)-benzamide; N-[(2S,3R)-2-methyl-1-azabicyclo[2.2.2]oct-3-yl]-4-(2-morpholin-4-yl-thiazol-5-yloxy)-benzamide; N-[(2S,3R)-2-methyl-1-azabicyclo[2.2.2]oct-3-yl]-4-([1,3,4]oxadiazol-2-yloxy)-benzamide; N-[(2S,3R)-2-methyl-1-azabicyclo[2.2.2]oct-3-yl]-4-(5-methyl[1,3,4]oxadiazol-2-yloxy)-benzamide; N-[(2S,3R)-2-methyl-1-azabicyclo[2.2.2]oct-3-yl]-4-(5-chloro[1,3,4]oxadiazol-2-yloxy)-benzamide; N-[(2S,3R)-2-methyl-1-azabicyclo[2.2.2]oct-3-yl]-4-(5-methoxy[1,3,4]oxadiazol-2-yloxy)-benzamide; N-[(2S,3R)-2-methyl-1-azabicyclo[2.2.2]oct-3-yl]-4-(5-trifluoromethyl[1,3,4]oxadiazol-2-yloxy)-benzamide; N-[(2S,3R)-2-methyl-1-azabicyclo[2.2.2]oct-3-yl]-4-(5-acetyl[1,3,4]oxadiazol-2-yloxy)-benzamide; N-[(2S,3R)-2-methyl-1-azabicyclo[2.2.2]oct-3-yl]-4-(5-acetamino[1,3,4]oxadiazol-2-yloxy)-benzamide; N-[(2S,3R)-2-methyl-1-azabicyclo[2.2.2]oct-3-yl]-4-(5-cyano[1,3,4]oxadiazol-2-yloxy)-benzamide; N-[(2S,3R)-2-methyl-1-azabicyclo[2.2.2]oct-3-yl]-4-(5-morpholin-4-yl-[1,3,4]oxadiazol-2-yloxy)-benzamide; N-[(2S,3R)-2-methyl-1-azabicyclo[2.2.2]oct-3-yl]-4-([1,3,4]thiadiazol-2-yloxy)-benzamide; N-[(2S,3R)-2-methyl-1-azabicyclo[2.2.2]oct-3-yl]-4-(5-methyl[1,3,4]thiadiazol-2-yloxy)-benzamide; N-[(2S,3R)-2-methyl-1-azabicyclo[2.2.2]oct-3-yl]-4-(5-chloro[1,3,4]thiadiazol-2-yloxy)-benzamide; N-[(2S,3R)-2-methyl-1-azabicyclo[2.2.2]oct-3-yl]-4-(5-methoxy[1,3,4]thiadiazol-2-yloxy)-benzamide; N-[(2S,3R)-2-methyl-1-azabicyclo[2.2.2]oct-3-yl]-4-(5-trifluoromethyl[1,3,4]thiadiazol-2-yloxy)-benzamide; N-[(2S,3R)-2-methyl-1-azabicyclo[2.2.2]oct-3-yl]-4-(5-acetyl[1,3,4]thiadiazol-2-yloxy)-benzamide; N-[(2S,3R)-2-methyl-1-azabicyclo[2.2.2]oct-3-yl]-4-(5-acetamino[1,3,4]thiadiazol-2-yloxy)-benzamide; N-[(2S,3R)-2-methyl- 1-azabicyclo[2.2.2]oct-3-yl]-4-(5-cyano[1,3,4]thiadiazol-2-yloxy)-benzamide; N-[(2S,3R)-2-methyl-1-azabicyclo[2.2.2]oct-3-yl]-4-(5-morpholin-4-yl-[1,3,4]thiadiazol-2-yloxy)-benzamide; N-[(2S,3R)-2-methyl-1-azabicyclo[2.2.2]oct-3-yl]-4-(4-aminophenylsulfanyl)-benzamide; N-[(2S,3R)-2-methyl-1-azabicyclo[2.2.2]oct-3-yl]-4-(3-aminophenylsulfanyl)-benzamide; N-[(2S,3R)-2-methyl-1-azabicyclo[2.2.2]oct-3-yl]-4-(2-aminophenylsulfanyl)-benzamide; N-[(2S,3R)-2-methyl-1-azabicyclo[2.2.2]oct-3-yl]-4-(4-methanesulfonylamino-phenylsulfanyl)-benzamide; N-[(2S,3R)-2-methyl-1-azabicyclo[2.2.2]oct-3-yl]-4-(3-methanesulfonylamino-phenylsulfanyl)-benzamide; N-[(2S,3R)-2-methyl-1-azabicyclo[2.2.2]oct-3-yl]-4-(2-methanesulfonylamino-phenylsulfanyl)-benzamide; N-[(2S,3R)-2-methyl-1-azabicyclo[2.2.2]oct-3-yl]-4-(4-acetoxyphenylsulfanyl)-benzamide; N-[(2S,3R)-2-methyl-1-azabicyclo[2.2.2]oct-3-yl]-4-(3-acetoxyphenylsulfanyl)-benzamide; N-[(2S,3R)-2-methyl-1-azabicyclo[2.2.2]oct-3-yl]-4-(2-acetoxyphenylsulfanyl)-benzamide; N-[(2S,3R)-2-methyl-1-azabicyclo[2.2.2]oct-3-yl]-4-(4-acetylphenylsulfanyl)-benzamide; N-[(2S,3R)-2-methyl-1-azabicyclo[2.2.2]oct-3-yl]-4-(3-acetylphenylsulfanyl)-benzamide; N-[(2S,3R)-2-methyl-1-azabicyclo[2.2.2]oct-3-yl]-4-(2-acetylphenylsulfanyl)-benzamide; N-[(2S,3R)-2-methyl-1-azabicyclo[2.2.2]oct-3-yl]-4-(4-carbamoylphenylsulfanyl)-benzamide; N-[(2S,3R)-2-methyl-1-azabicyclo[2.2.2]oct-3-yl]-4-(3-carbamoylphenylsulfanyl)-benzamide; N-[(2S,3R)-2-methyl-1-azabicyclo[2.2.2]oct-3-yl]-4-(2-carbamoylphenylsulfanyl)-benzamide; N-[(2S,3R)-2-methyl-1-azabicyclo[2.2.2]oct-3-yl]-4-(4-cyanophenylsulfanyl)-benzamide; N-[(2S,3R)-2-methyl-1-azabicyclo[2.2.2]oct-3-yl]-4-(3-cyanophenylsulfanyl)-benzamide; N-[(2S,3R)-2-methyl-1-azabicyclo[2.2.2]oct-3-yl]-4-(2-cyanophenylsulfanyl)-benzamide; N-[(2S,3R)-2-methyl-1-azabicyclo[2.2.2]oct-3-yl]-4-(4-sulfamoylphenylsulfanyl)-benzamide; N-[(2S,3R)-2-methyl-1-azabicyclo[2.2.2]oct-3-yl]-4-(3-sulfamoylphenylsulfanyl)-benzamide; N-[(2S,3R)-2-methyl-1-azabicyclo[2.2.2]oct-3-yl]-4-(2-sulfamoylphenylsulfanyl)-benzamide; N-[(2S,3R)-2-methyl-1-azabicyclo[2.2.2]oct-3-yl]-4-(4-hydroxyphenylsulfanyl)-benzamide; N-[(2S,3R)-2-methyl-1-azabicyclo[2.2.2]oct-3-yl]-4-(3-hydroxyphenylsulfanyl)-benzamide; N-[(2S,3R)-2-methyl-1-azabicyclo[2.2.2]oct-3-yl]-4-(2-hydroxyphenylsulfanyl)-benzamide; N-[(2S,3R)-2-methyl-1-azabicyclo[2.2.2]oct-3-yl]-4-(4-acetamidophenylsulfanyl)-benzamide; N-[(2S,3R)-2-methyl-1-azabicyclo[2.2.2]oct-3-yl]-4-(3-acetamidophenylsulfanyl)-benzamide; N-[(2S,3R)-2-methyl-1-azabicyclo[2.2.2]oct-3-yl]-4-(2-acetamidophenylsulfanyl)-benzamide; N-[(2S,3R)-2-methyl-1-azabicyclo[2.2.2]oct-3-yl]-4-(thiophen-2-ylsulfanyl)-benzamide; N-[(2S,3R)-2-methyl-1-azabicyclo[2.2.2]oct-3-yl]-4-(5-methy-thiophen-2-ylsulfanyl)-benzamide; N-[(2S,3R)-2-methyl-1-azabicyclo[2.2.2]oct-3-yl]-4-(5-chlorothiophen-2-ylsulfanyl)-benzamide; N-[(2S,3R)-2-methyl-1-azabicyclo[2.2.2]oct-3-yl]-4-(5-methoxythiophen-2-ylsulfanyl)-benzamide; N-[(2S,3R)-2-methyl-1-azabicyclo[2.2.2]oct-3-yl]-4-(5-trifluoromethy-thiophen-2-ylsulfanyl)-benzamide; N-[(2S,3R)-2-methyl-1-azabicyclo[2.2.2]oct-3-yl]-4-(5-acety-thiophen-2-ylsulfanyl)-benzamide; N-[(2S,3R)-2-methyl-1-azabicyclo[2.2.2]oct-3-yl]-4-(5-acetaminothiophen-2-ylsulfanyl)-benzamide; N-[(2S,3R)-2-methyl-1-azabicyclo[2.2.2]oct-3-yl]-4-(5-cyanothiophen-2-ylsulfanyl)-benzamide; N-[(2S,3R)-2-methyl-1-azabicyclo[2.2.2]oct-3-yl]-4-(5-morpholin-4-yl-thiophen-2-ylsulfanyl)-benzamide; N-[(2S,3R)-2-methyl-1-azabicyclo[2.2.2]oct-3-yl]-4-(4-methy-thiophen-2-ylsulfanyl)-benzamide; N-[(2S,3R)-2-methyl-1-azabicyclo[2.2.2]oct-3-yl]-4-(4-chlorothiophen-2-ylsulfanyl)-benzamide; N-[(2S,3R)-2-methyl-1-azabicyclo[2.2.2]oct-3-yl]-4-(4-methoxythiophen-2-ylsulfanyl)-benzamide; N-[(2S,3R)-2-methyl-1-azabicyclo[2.2.2]oct-3-yl]-4-(4-trifluoromethy-thiophen-2-ylsulfanyl)-benzamide; N-[(2S,3R)-2-methyl-1-azabicyclo[2.2.2]oct-3-yl]-4-(4-acety-thiophen-2-ylsulfanyl)-benzamide; N-[(2S,3R)-2-methyl-1-azabicyclo[2.2.2]oct-3-yl]-4-(4-acetaminothiophen-2-ylsulfanyl)-benzamide; N-[(2S,3R)-2-methyl-1-azabicyclo[2.2.2]oct-3-yl]-4-(4-cyanothiophen-2-ylsulfanyl)-benzamide; N-[(2S,3R)-2-methyl-1-azabicyclo[2.2.2]oct-3-yl]-4-(4-morpholin-4-yl-thiophen-2-ylsulfanyl)-benzamide; N-[(2S,3R)-2-methyl-1-azabicyclo[2.2.2]oct-3-yl]-4-(furan-2-ylsulfanyl)-benzamide; N-[(2S,3R)-2-methyl-1-azabicyclo[2.2.2]oct-3-yl]-4-(5-methylfuran-2-ylsulfanyl)-benzamide; N-[(2S,3R)-2-methyl-1-azabicyclo[2.2.2]oct-3-yl]-4-(5-chlorofuran-2-ylsulfanyl)-benzamide; N-[(2S,3R)-2-methyl-1-azabicyclo[2.2.2]oct-3-yl]-4-(5-methoxyfuran-2-ylsulfanyl)-benzamide; N-[(2S,3R)-2-methyl-1-azabicyclo[2.2.2]oct-3-yl]-4-(5-trifluoromethylfuran-2-ylsulfanyl)-benzamide; N-[(2S,3R)-2-methyl-1-azabicyclo[2.2.2]oct-3-yl]-4-(5-acetylfuran-2-ylsulfanyl)-benzamide; N-[(2S,3R)-2-methyl-1-azabicyclo[2.2.2]oct-3-yl]-4-(5-acetaminofuran-2-ylsulfanyl)-benzamide; N-[(2S,3R)-2-methyl-1-azabicyclo[2.2.2]oct-3-yl]-4-(5-cyanofuran-2-ylsulfanyl)-benzamide; N-[(2S,3R)-2-methyl-1-azabicyclo[2.2.2]oct-3-yl]-4-(5-morpholin-4-yl-furan-2-ylsulfanyl)-benzamide; N-[(2S,3R)-2-methyl-1-azabicyclo[2.2.2]oct-3-yl]-4-(4-methylfuran-2-ylsulfanyl)-benzamide; N-[(2S,3R)-2-methyl-1-azabicyclo[2.2.2]oct-3-yl]-4-(4-chlorofuran-2-ylsulfanyl)-benzamide; N-[(2S,3R)-2-methyl-1-azabicyclo[2.2.2]oct-3-yl]-4-(4-methoxyfuran-2-ylsulfanyl)-benzamide; N-[(2S,3R)-2-methyl-1-azabicyclo[2.2.2]oct-3-yl]-4-(4-trifluoromethylfuran-2-ylsulfanyl)-benzamide; N-[(2S,3R)-2-methyl-1-azabicyclo[2.2.2]oct-3-yl]-4-(4-acetylfuran-2-ylsulfanyl)-benzamide; N-[(2S,3R)-2-methyl-1-azabicyclo[2.2.2]oct-3-yl]-4-(4-acetaminofuran-2-ylsulfanyl)-benzamide; N-[(2S,3R)-2-methyl-1-azabicyclo[2.2.2]oct-3-yl]-4-(4-cyanofuran-2-ylsulfanyl)-benzamide; N-[(2S,3R)-2-methyl-1-azabicyclo[2.2.2]oct-3-yl]-4-(4-morpholin-4-yl-furan-2-ylsulfanyl)-benzamide; N-[(2S,3R)-2-methyl-1-azabicyclo[2.2.2]oct-3-yl]-4-(oxazol-2-ylsulfanyl)-benzamide; N-[(2S,3R)-2-methyl-1-azabicyclo[2.2.2]oct-3-yl]-4-(5-methyloxazol-2-ylsulfanyl)-benzamide; N-[(2S,3R)-2-methyl-1-azabicyclo[2.2.2]oct-3-yl]-4-(5-chlorooxazol-2-ylsulfanyl)-benzamide; N-[(2S,3R)-2-methyl-1-azabicyclo[2.2.2]oct-3-yl]-4-(5-methoxyoxazol-2-ylsulfanyl)-benzamide; N-[(2S,3R)-2-methyl-1-azabicyclo[2.2.2]oct-3-yl]-4-(5- trifluoromethyloxazol-2-ylsulfanyl)-benzamide; N-[(2S,3R)-2-methyl-1-azabicyclo[2.2.2]oct-3-yl]-4-(5-acetyloxazol-2-ylsulfanyl)-benzamide; N-[(2S,3R)-2-methyl-1-azabicyclo[2.2.2]oct-3-yl]-4-(5-acetaminooxazol-2-ylsulfanyl)-benzamide; N-[(2S,3R)-2-methyl-1-azabicyclo[2.2.2]oct-3-yl]-4-(5-cyanooxazol-2-ylsulfanyl)-benzamide; N-[(2S,3R)-2-methyl-1-azabicyclo[2.2.2]oct-3-yl]-4-(5-morpholin-4-yl-oxazol-2-ylsulfanyl)-benzamide; N-[(2S,3R)-2-methyl-1-azabicyclo[2.2.2]oct-3-yl]-4-(oxazol-2-ylsulfanyl)-benzamide; N-[(2S,3R)-2-methyl-1-azabicyclo[2.2.2]oct-3-yl]-4-(4-methyloxazol-2-ylsulfanyl)-benzamide; N-[(2S,3R)-2-methyl-1-azabicyclo[2.2.2]oct-3-yl]-4-(4-chlorooxazol-2-ylsulfanyl)-benzamide; N-[(2S,3R)-2-methyl-1-azabicyclo[2.2.2]oct-3-yl]-4-(4-methoxyoxazol-2-ylsulfanyl)-benzamide; N-[(2S,3R)-2-methyl-1-azabicyclo[2.2.2]oct-3-yl]-4-(4-trifluoromethyloxazol-2-ylsulfanyl)-benzamide; N-[(2S,3R)-2-methyl-1-azabicyclo[2.2.2]oct-3-yl]-4-(4-acetyloxazol-2-ylsulfanyl)-benzamide; N-[(2S,3R)-2-methyl-1-azabicyclo[2.2.2]oct-3-yl]-4-(4-acetaminooxazol-2-ylsulfanyl)-benzamide; N-[(2S,3R)-2-methyl-1-azabicyclo[2.2.2]oct-3-yl]-4-(4-cyanooxazol-2-ylsulfanyl)-benzamide; N-[(2S,3R)-2-methyl-1-azabicyclo[2.2.2]oct-3-yl]-4-(4-morpholin-4-yl-oxazol-2-ylsulfanyl)-benzamide; N-[(2S,3R)-2-methyl-1-azabicyclo[2.2.2]oct-3-yl]-4-(oxazol-5-ylsulfanyl)-benzamide; N-[(2S,3R)-2-methyl-1-azabicyclo[2.2.2]oct-3-yl]-4-(2-methyloxazol-5-ylsulfanyl)-benzamide; N-[(2S,3R)-2-methyl-1-azabicyclo[2.2.2]oct-3-yl]-4-(2-chlorooxazol-5-ylsulfanyl)-benzamide; N-[(2S,3R)-2-methyl-1-azabicyclo[2.2.2]oct-3-yl]-4-(2-methoxyoxazol-5-ylsulfanyl)-benzamide; N-[(2S,3R)-2-methyl-1-azabicyclo[2.2.2]oct-3-yl]-4-(2-trifluoromethyloxazol-5-ylsulfanyl)-benzamide; N-[(2S,3R)-2-methyl-1-azabicyclo[2.2.2]oct-3-yl]-4-(2-acetyloxazol-5-ylsulfanyl)-benzamide; N-[(2S,3R)-2-methyl-1-azabicyclo[2.2.2]oct-3-yl]-4-(2-acetaminooxazol-5-ylsulfanyl)-benzamide; N-[(2S,3R)-2-methyl-1-azabicyclo[2.2.2]oct-3-yl]-4-(2-cyanooxazol-5-ylsulfanyl)-benzamide; N-[(2S,3R)-2-methyl-1-azabicyclo[2.2.2]oct-3-yl]-4-(2-morpholin-4-yl-oxazol-5-ylsulfanyl)-benzamide; N-[(2S,3R)-2-methyl-1-azabicyclo[2.2.2]oct-3-yl]-4-(thiazol-2-ylsulfanyl)-benzamide; N-[(2S,3R)-2-methyl-1-azabicyclo[2.2.2]oct-3-yl]-4-(5-methylthiazol-2-ylsulfanyl)-benzamide; N-[(2S,3R)-2-methyl-1-azabicyclo[2.2.2]oct-3-yl]-4-(5-chlorothiazol-2-ylsulfanyl)-benzamide; N-[(2S,3R)-2-methyl-1-azabicyclo[2.2.2]oct-3-yl]-4-(5-methoxythiazol-2-ylsulfanyl)-benzamide; N-[(2S,3R)-2-methyl-1-azabicyclo[2.2.2]oct-3-yl]-4-(5-trifluoromethylthiazol-2-ylsulfanyl)-benzamide; N-[(2S,3R)-2-methyl-1-azabicyclo[2.2.2]oct-3-yl]-4-(5-acetylthiazol-2-ylsulfanyl)-benzamide; N-[(2S,3R)-2-methyl-1-azabicyclo[2.2.2]oct-3-yl]-4-(5-acetaminothiazol-2-ylsulfanyl)-benzamide; N-[(2S,3R)-2-methyl-1-azabicyclo[2.2.2]oct-3-yl]-4-(5-cyanothiazol-2-ylsulfanyl)-benzamide; N-[(2S,3R)-2-methyl-1-azabicyclo[2.2.2]oct-3-yl]-4-(5-morpholin-4-yl-thiazol-2-ylsulfanyl)-benzamide; N-[(2S,3R)-2-methyl-1-azabicyclo[2.2.2]oct-3-yl]-4-(thiazol-2-ylsulfanyl)-benzamide; N-[(2S,3R)-2-methyl-1-azabicyclo[2.2.2]oct-3-yl]-4-(4-methylthiazol-2-ylsulfanyl)-benzamide; N-[(2S,3R)-2-methyl-1-azabicyclo[2.2.2]oct-3-yl]-4-(4-chlorothiazol-2-ylsulfanyl)-benzamide; N-[(2S,3R)-2-methyl-1-azabicyclo[2.2.2]oct-3-yl]-4-(4-methoxythiazol-2-ylsulfanyl)-benzamide; N-[(2S,3R)-2-methyl-1-azabicyclo[2.2.2]oct-3-yl]-4-(4-trifluoromethylthiazol-2-ylsulfanyl)-benzamide; N-[(2S,3R)-2-methyl-1-azabicyclo[2.2.2]oct-3-yl]-4-(4-acetylthiazol-2-ylsulfanyl)-benzamide; N-[(2S,3R)-2-methyl-1-azabicyclo[2.2.2]oct-3-yl]-4-(4-acetaminothiazol-2-ylsulfanyl)-benzamide; N-[(2S,3R)-2-methyl-1-azabicyclo[2.2.2]oct-3-yl]-4-(4-cyanothiazol-2-ylsulfanyl)-benzamide; N-[(2S,3R)-2-methyl-1-azabicyclo[2.2.2]oct-3-yl]-4-(4-morpholin-4-yl-thiazol-2-ylsulfanyl)-benzamide; N-[(2S,3R)-2-methyl-1-azabicyclo[2.2.2]oct-3-yl]-4-(thiazol-5-ylsulfanyl)-benzamide; N-[(2S,3R)-2-methyl-1-azabicyclo[2.2.2]oct-3-yl]-4-(2-methylthiazol-5-ylsulfanyl)-benzamide; N-[(2S,3R)-2-methyl-1-azabicyclo[2.2.2]oct-3-yl]-4-(2-chlorothiazol-5-ylsulfanyl)-benzamide; N-[(2S,3R)-2-methyl-1-azabicyclo[2.2.2]oct-3-yl]-4-(2-methoxythiazol-5-ylsulfanyl)-benzamide; N-[(2S,3R)-2-methyl-1-azabicyclo[2.2.2]oct-3-yl]-4-(2-trifluoromethylthiazol-5-ylsulfanyl)-benzamide; N-[(2S,3R)-2-methyl-1-azabicyclo[2.2.2]oct-3-yl]-4-(2-acetylthiazol-5-ylsulfanyl)-benzamide; N-[(2S,3R)-2-methyl-1-azabicyclo[2.2.2]oct-3-yl]-4-(2-acetaminothiazol-5-ylsulfanyl)-benzamide; N-[(2S,3R)-2-methyl-1-azabicyclo[2.2.2]oct-3-yl]-4-(2-cyanothiazol-5-ylsulfanyl)-benzamide; N-[(2S,3R)-2-methyl-1-azabicyclo[2.2.2]oct-3-yl]-4-(2-morpholin-4-yl-thiazol-5-ylsulfanyl)-benzamide; N-[(2S,3R)-2-methyl-1-azabicyclo[2.2.2]oct-3-yl]-4-([1,3,4]oxadiazol-2-ylsulfanyl)-benzamide; N-[(2S,3R)-2-methyl-1-azabicyclo[2.2.2]oct-3-yl]-4-(5-methyl[1,3,4]oxadiazol-2-ylsulfanyl)-benzamide; N-[(2S,3R)-2-methyl-1-azabicyclo[2.2.2]oct-3-yl]-4-(5-chloro[1,3,4]oxadiazol-2-ylsulfanyl)-benzamide; N-[(2S,3R)-2-methyl-1-azabicyclo[2.2.2]oct-3-yl]-4-(5-methoxy[1,3,4]oxadiazol-2-ylsulfanyl)-benzamide; N-[(2S,3R)-2-methyl-1-azabicyclo[2.2.2]oct-3-yl]-4-(5-trifluoromethyl[1,3,4]oxadiazol-2-ylsulfanyl)-benzamide; N-[(2S,3R)-2-methyl-1-azabicyclo[2.2.2]oct-3-yl]-4-(5-acetyl[1,3,4]oxadiazol-2-ylsulfanyl)-benzamide; N-[(2S,3R)-2-methyl-1-azabicyclo[2.2.2]oct-3-yl]-4-(5-acetamino[1,3,4]oxadiazol-2-ylsulfanyl)-benzamide; N-[(2S,3R)-2-methyl-1-azabicyclo[2.2.2]oct-3-yl]-4-(5-cyano[1,3,4]oxadiazol-2-ylsulfanyl)-benzamide; N-[(2S,3R)-2-methyl-1-azabicyclo[2.2.2]oct-3-yl]-4-(5-morpholin-4-yl-[1,3,4]oxadiazol-2-ylsulfanyl)-benzamide; N-[(2S,3R)-2-methyl-1-azabicyclo[2.2.2]oct-3-yl]-4-([1,3,4]thiadiazol-2-ylsulfanyl)-benzamide; N-[(2S,3R)-2-methyl-1-azabicyclo[2.2.2]oct-3-yl]-4-(5-methyl[1,3,4]thiadiazol-2-ylsulfanyl)-benzamide; N-[(2S,3R)-2-methyl-1-azabicyclo[2.2.2]oct-3-yl]-4-(5-chloro[1,3,4]thiadiazol-2-ylsulfanyl)-benzamide; N-[(2S,3R)-2-methyl-1-azabicyclo[2.2.2]oct-3-yl]-4-(5-methoxy[1,3,4]thiadiazol-2-ylsulfanyl)-benzamide; N-[(2S,3R)-2-methyl-1-azabicyclo[2.2.2]oct-3-yl]-4-(5-trifluoromethyl[1,3,4]thiadiazol-2-ylsulfanyl)-benzamide; N-[(2S,3R)-2-methyl-1-azabicyclo[2.2.2]oct-3-yl]-4-(5-acetyl[1,3,4]thiadiazol-2-ylsulfanyl)-benzamide; N-[(2S,3R)-2-methyl-1-azabicyclo[2.2.2]oct-3-yl]-4-(5-acetamino[1,3,4]thiadiazol-2-ylsulfanyl)-benzamide; N-[(2S,3R)-2-methyl-1-azabicyclo[2.2.2]oct-3-yl]-4-(5-cyano[1,3,4]

thiadiazol-2-ylsulfanyl)-benzamide; N-[(2S,3R)-2-methyl-1-azabicyclo[2.2.2]oct-3-yl]-4-(5-morpholin-4-yl-[1,3,4]thiadiazol-2-ylsulfanyl)-benzamide; N-[(2S,3R)-2-methyl-1-azabicyclo[2.2.2]oct-3-yl]-4-(pyrrol-2-yloxy)-benzamide; N-[(2S,3R)-2-methyl-1-azabicyclo[2.2.2]oct-3-yl]-4-(5-methylpyrrolrrol-2-yloxy)-benzamide; N-[(2S,3R)-2-methyl-1-azabicyclo[2.2.2]oct-3-yl]-4-(5-chloropyrrol-2-yloxy)-benzamide; N-[(2S,3R)-2-methyl-1-azabicyclo[2.2.2]oct-3-yl]-4-(5-methoxypyrrol-2-yloxy)-benzamide; N-[(2S,3R)-2-methyl-1-azabicyclo[2.2.2]oct-3-yl]-4-(5-trifluoromethylpyrrolrrol-2-yloxy)-benzamide; N-[(2S,3R)-2-methyl-1-azabicyclo[2.2.2]oct-3-yl]-4-(5-acetylpyrrol-2-yloxy)-benzamide; N-[(2S,3R)-2-methyl-1-azabicyclo[2.2.2]oct-3-yl]-4-(5-acetaminopyrrol -2-yloxy)-benzamide; N-[(2S,3R)-2-methyl-1-azabicyclo[2.2.2]oct-3-yl]-4-(5-cyanopyrrol-2-yloxy)-benzamide; N-[(2S,3R)-2-methyl-1-azabicyclo[2.2.2]oct-3-yl]-4-(5-morpholin-4-yl-pyrrol-2-yloxy)-benzamide; N-[(2S,3R)-2-methyl-1-azabicyclo[2.2.2]oct-3-yl]-4-(3H-imidazol-4-yloxy)-benzamide; N-[(2S,3R)-2-methyl-1-azabicyclo[2.2.2]oct-3-yl]-4-(2-methyl-3H-imidazol-4-yloxy)-benzamide; N-[(2S,3R)-2-methyl-1-azabicyclo[2.2.2]oct-3-yl]-4-(2-chloro-3H-imidazol-4-yloxy)-benzamide; N-[(2S,3R)-2-methyl-1-azabicyclo[2.2.2]oct-3-yl]-4-(2-methoxy-3H-imidazol-4-yloxy)-benzamide; N-[(2S,3R)-2-methyl-1-azabicyclo[2.2.2]oct-3-yl]-4-(2-trifluoromethyl-3H-imidazol-4-yloxy)-benzamide; N-[(2S,3R)-2-methyl-1-azabicyclo[2.2.2]oct-3-yl]-4-(2-acetyl-3H-imidazol-4-yloxy)-benzamide; N-[(2S,3R)-2-methyl-1-azabicyclo[2.2.2]oct-3-yl]-4-(2-acetamino-3H-imidazol-4-yloxy)-benzamide; N-[(2S,3R)-2-methyl-1-azabicyclo[2.2.2]oct-3-yl]-4-(2-cyano-3H-imidazol-4-yloxy)-benzamide; N-[(2S,3R)-2-methyl-1-azabicyclo[2.2.2]oct-3-yl]-4-(2-morpholin-4-yl-3H-imidazol-4-yloxy)-benzamide; N-[(2S,3R)-2-methyl-1-azabicyclo[2.2.2]oct-3-yl]-4-(isoxazol-2-yloxy)-benzamide; N-[(2S,3R)-2-methyl-1-azabicyclo[2.2.2]oct-3-yl]-4-(5-methylisoxazol-3-yloxy)-benzamide; N-[(2S,3R)-2-methyl-1-azabicyclo[2.2.2]oct-3-yl]-4-(5-chloroisoxazol-3-yloxy)-benzamide; N-[(2S,3R)-2-methyl-1-azabicyclo[2.2.2]oct-3-yl]-4-(5-methoxyisoxazol-3-yloxy)-benzamide; N-[(2S,3R)-2-methyl-1-azabicyclo[2.2.2]oct-3-yl]-4-(5-trifluoromethylisoxazol-3-yloxy)-benzamide; N-[(2S,3R)-2-methyl-1-azabicyclo[2.2.2]oct-3-yl]-4-(5-acetylisoxazol-3-yloxy)-benzamide; N-[(2S,3R)-2-methyl-1-azabicyclo[2.2.2]oct-3-yl]-4-(5-acetaminoisoxazol-3-yloxy)-benzamide; N-[(2S,3R)-2-methyl-1-azabicyclo[2.2.2]oct-3-yl]-4-(5-cyanoisoxazol-3-yloxy)-benzamide; N-[(2S,3R)-2-methyl-1-azabicyclo[2.2.2]oct-3-yl]-4-(5-morpholin-4-yl-isoxazol-3-yloxy)-benzamide; N-[(2S,3R)-2-methyl-1-azabicyclo[2.2.2]oct-3-yl]-4-(isothiazol-2-yloxy)-benzamide; N-[(2S,3R)-2-methyl-1-azabicyclo[2.2.2]oct-3-yl]-4-(5-methyl-isothiazol-3-yloxy)-benzamide; N-[(2S,3R)-2-methyl-1-azabicyclo[2.2.2]oct-3-yl]-4-(5-chloroisothiazol-3-yloxy)-benzamide; N-[(2S,3R)-2-methyl-1-azabicyclo[2.2.2]oct-3-yl]-4-(5-methoxyisothiazol-3-yloxy)-benzamide; N-[(2S,3R)-2-methyl-1-azabicyclo[2.2.2]oct-3-yl]-4-(5-trifluoromethyl-isothiazol-3-yloxy)-benzamide; N-[(2S,3R)-2-methyl-1-azabicyclo[2.2.2]oct-3-yl]-4-(5-acetyl-isothiazol-3-yloxy)-benzamide; N-[(2S,3R)-2-methyl-1-azabicyclo[2.2.2]oct-3-yl]-4-(5-acetaminoisothiazol-3-yloxy)-benzamide; N-[(2S,3R)-2-methyl-1-azabicyclo[2.2.2]oct-3-yl]-4-(5-cyanoisothiazol-3-yloxy)-benzamide; N-[(2S,3R)-2-methyl-1-azabicyclo[2.2.2]oct-3-yl]-4-(5-morpholin-4-yl-isothiazol-3-yloxy)-benzamide; N-[(2S,3R)-2-methyl-1-azabicyclo[2.2.2]oct-3-yl]-4-(pyrrol-2-ylsulfanyl)-benzamide; N-[(2S,3R)-2-methyl-1-azabicyclo[2.2.2]oct-3-yl]-4-(5-methylpyrrolrrol-2-ylsulfanyl)-benzamide; N-[(2S,3R)-2-methyl-1-azabicyclo[2.2.2]oct-3-yl]-4-(5-chloropyrrol-2-ylsulfanyl)-benzamide; N-[(2S,3R)-2-methyl-1-azabicyclo[2.2.2]oct-3-yl]-4-(5-methoxypyrrol-2-ylsulfanyl)-benzamide; N-[(2S,3R)-2-methyl-1-azabicyclo[2.2.2]oct-3-yl]-4-(5-trifluoromethylpyrrolrrol-2-ylsulfanyl)-benzamide; N-[(2S,3R)-2-methyl-1-azabicyclo[2.2.2]oct-3-yl]-4-(5-acetylpyrrol-2-ylsulfanyl)-benzamide; N-[(2S,3R)-2-methyl-1-azabicyclo[2.2.2]oct-3-yl]-4-(5-acetaminopyrrol-2-ylsulfanyl)-benzamide; N-[(2S,3R)-2-methyl-1-azabicyclo[2.2.2]oct-3-yl]-4-(5-cyanopyrrol-2-ylsulfanyl)-benzamide; N-[(2S,3R)-2-methyl-1-azabicyclo[2.2.2]oct-3-yl]-4-(5-morpholin-4-yl-pyrrol-2-ylsulfanyl)-benzamide; N-[(2S,3R)-2-methyl-1-azabicyclo[2.2.2]oct-3-yl]-4-(3H-imidazol-4-ylsulfanyl)-benzamide; N-[(2S,3R)-2-methyl-1-azabicyclo[2.2.2]oct-3-yl]-4-(2-methyl-3H-imidazol-4-ylsulfanyl)-benzamide; N-[(2S,3R)-2-methyl-1-azabicyclo[2.2.2]oct-3-yl]-4-(2-chloro-3H-imidazol-4-ylsulfanyl)-benzamide; N-[(2S,3R)-2-methyl-1-azabicyclo[2.2.2]oct-3-yl]-4-(2-methoxy-3H-imidazol-4-ylsulfanyl)-benzamide; N-[(2S,3R)-2-methyl-1-azabicyclo[2.2.2]oct-3-yl]-4-(2-trifluoromethyl-3H-imidazol-4-ylsulfanyl)-benzamide; N-[(2S,3R)-2-methyl-1-azabicyclo[2.2.2]oct-3-yl]-4-(2-acetyl-3H-imidazol-4-ylsulfanyl)-benzamide; N-[(2S,3R)-2-methyl-1-azabicyclo[2.2.2]oct-3-yl]-4-(2-acetamino-3H-imidazol-4-ylsulfanyl)-benzamide; N-[(2S,3R)-2-methyl-1-azabicyclo[2.2.2]oct-3-yl]-4-(2-cyano-3H-imidazol-4-ylsulfanyl)-benzamide; N-[(2S,3R)-2-methyl-1-azabicyclo[2.2.2]oct-3-yl]-4-(2-morpholin-4-yl-3H-imidazol-4-ylsulfanyl)-benzamide; N-[(2S,3R)-2-methyl-1-azabicyclo[2.2.2]oct-3-yl]-4-(isoxazol-2-ylsulfanyl)-benzamide; N-[(2S,3R)-2-methyl-1-azabicyclo[2.2.2]oct-3-yl]-4-(5-methylisoxazol-3-ylsulfanyl)-benzamide; N-[(2S,3R)-2-methyl-1-azabicyclo[2.2.2]oct-3-yl]-4-(5-chloroisoxazol-3-ylsulfanyl)-benzamide; N-[(2S,3R)-2-methyl-1-azabicyclo[2.2.2]oct-3-yl]-4-(5-methoxyisoxazol-3-ylsulfanyl)-benzamide; N-[(2S,3R)-2-methyl-1-azabicyclo[2.2.2]oct-3-yl]-4-(5-trifluoromethylisoxazol-3-ylsulfanyl)-benzamide; N-[(2S,3R)-2-methyl-1-azabicyclo[2.2.2]oct-3-yl]-4-(5-acetylisoxazol-3-ylsulfanyl)-benzamide; N-[(2S,3R)-2-methyl-1-azabicyclo[2.2.2]oct-3-yl]-4-(5-acetaminoisoxazol-3-ylsulfanyl)-benzamide; N-[(2S,3R)-2-methyl-1-azabicyclo[2.2.2]oct-3-yl]-4-(5-cyanoisoxazol-3-ylsulfanyl)-benzamide; N-[(2S,3R)-2-methyl-1-azabicyclo[2.2.2]oct-3-yl]-4-(5-morpholin-4-yl-isoxazol-3-ylsulfanyl)-benzamide; N-[(2S,3R)-2-methyl-1-azabicyclo[2.2.2]oct-3-yl]-4-(isothiazol-2-ylsulfanyl)-benzamide; N-[(2S,3R)-2-methyl-1-azabicyclo[2.2.2]oct-3-yl]-4-(5-methyl-isothiazol-3-ylsulfanyl)-benzamide; N-[(2S,3R)-2-methyl-1-azabicyclo[2.2.2]oct-3-yl]-4-(5-chloroisothiazol-3-ylsulfanyl)-benzamide; N-[(2S,3R)-2-methyl-1-azabicyclo[2.2.2]oct-3-yl]-4-(5-methoxyisothiazol-3-ylsulfanyl)-benzamide; N-[(2S, 3R)-2-methyl-1-azabicyclo[2.2.2]oct-3-yl]-4-(5-trifluoromethyl-isothiazol-3-ylsulfanyl)-benzamide; N-[(2S,3R)-2-methyl-1-azabicyclo[2.2.2]oct-3-yl]-4-(5-acetyl-isothiazol-3-ylsulfanyl)-benzamide; N-[(2S,3R)-2-methyl-1-azabicyclo[2.2.2]oct-3-yl]-4-(5-acetaminoisothiazol-3-ylsulfanyl)-benzamide; N-[(2S,3R)-2-methyl-1-azabicyclo[2.2.2]oct-3-yl]-4-(5-cyanoisothiazol-3-ylsulfanyl)-benzamide; N-[(2S,3R)-2-methyl-1-azabicyclo[2.2.2]oct-3-yl]-4-(5-morpholin-4-yl-isothiazol-3-ylsulfanyl)-benzamide; N-[(2S,3R)-2-methyl-1-azabicyclo[2.2.2]oct-3-yl]-4-(6-methylpyrrolridin-3-yloxy)-benzamide; N-[(2S,3R)-2-methyl-1-azabicyclo[2.2.2]oct-3-yl]-4-(6--chloropyridin-3-yloxy)-benzamide; N-[(2S,3R)-2-methyl-1-azabicyclo[2.2.2]oct-3-yl]-4-(6-methoxypyridin-3-yloxy)-benzamide; N-[(2S,3R)-2-methyl-1-azabicyclo[2.2.2]oct-3-yl]-4-(6-trifluoromethylpyrrolridin-3-yloxy)-benzamide; N-[(2S,3R)-2-methyl-1-azabicyclo[2.2.2]oct-3-yl]-4-(6-acetylpyridin-3-yloxy)-benzamide; N-[(2S,3R)-2-methyl-1-azabicyclo[2.2.2]oct-3-yl]-4-(6-acetaminopyridin-3-yloxy)-benzamide; N-[(2S,3R)-2-methyl-1-azabicyclo[2.2.2]oct-3-yl]-4-(6-cyanopyridin-3-yloxy)-benzamide; N-[(2S,3R)-2-methyl-1-azabicyclo[2.2.2]oct-3-yl]-4-(6-morpholin-4-yl-pyridin-3-yloxy)-benzamide; N-[(2S,3R)-2-methyl-1-azabicyclo[2.2.2]oct-3-yl]-4-(2-methylpyrrolridin-4-yloxy)-benzamide; N-[(2S,3R)-2-methyl-1-azabicyclo[2.2.2]oct-3-yl]-4-(2--chloropyridin-4-yloxy)-benzamide; N-[(2S,3R)-2-methyl-1-azabicyclo[2.2.2]oct-3-yl]-4-(2-methoxypyridin-4-yloxy)-benzamide; N-[(2S,3R)-2-methyl-1-azabicyclo[2.2.2]oct-3-yl]-4-(2-trifluoromethylpyrrolridin-4-yloxy)-benzamide; N-[(2S,3R)-2-methyl-1-azabicyclo[2.2.2]oct-3-yl]-4-(2-acetylpyridin-4-yloxy)-benzamide; N-[(2S,3R)-2-methyl-1-azabicyclo[2.2.2]oct-3-yl]-4-(2-acetaminopyridin-4-yloxy)-benzamide; N-[(2S,3R)-2-methyl-1-azabicyclo[2.2.2]oct-3-yl]-4-(2-cyanopyridin-4-yloxy)-benzamide; N-[(2S,3R)-2-methyl-1-azabicyclo[2.2.2]oct-3-yl]-4-(2-morpholin-4-yl-pyridin-4-yloxy)-benzamide; N-[(2S,3R)-2-methyl-1-azabicyclo[2.2.2]oct-3-yl]-4-(5-methylpyrrolridin-2-yloxy)-benzamide; N-[(2S,3R)-2-methyl-1-azabicyclo[2.2.2]oct-3-yl]-4-(5--chloropyridin-2-yloxy)-benzamide; N-[(2S,3R)-2-methyl-1-azabicyclo[2.2.2]oct-3-yl]-4-(5-methoxypyridin-2-yloxy)-benzamide; N-[(2S,3R)-2-methyl-1-azabicyclo[2.2.2]oct-3-yl]-4-(5-trifluoromethylpyrrolridin-2-yloxy)-benzamide; N-[(2S,3R)-2-methyl-1-azabicyclo[2.2.2]oct-3-yl]-4-(5-acetylpyridin-2-yloxy)-benzamide; N-[(2S,3R)-2-methyl-1-azabicyclo[2.2.2]oct-3-yl]-4-(5-acetaminopyridin-2-yloxy)-benzamide; N-[(2S,3R)-2-methyl-1-azabicyclo[2.2.2]oct-3-yl]-4-(5-cyanopyridin-2-yloxy)-benzamide; N-[(2S,3R)-2-methyl-1-azabicyclo[2.2.2]oct-3-yl]-4-(5-morpholin-4-yl-pyridin-2-yloxy)-benzamide; N-[(2S,3R)-2-methyl-1-azabicyclo[2.2.2]oct-3-yl]-4-(4-methylpyrrolridin-2-yloxy)-benzamide; N-[(2S,3R)-2-methyl-1-azabicyclo[2.2.2]oct-3-yl]-4-(4--chloropyridin-2-yloxy)-benzamide; N-[(2S,3R)-2-methyl-1-azabicyclo[2.2.2]oct-3-yl]-4-(4-methoxypyridin-2-yloxy)-benzamide; N-[(2S,3R)-2-methyl-1-azabicyclo[2.2.2]oct-3-yl]-4-(4-trifluoromethylpyrrolridin-2-yloxy)-benzamide; N-[(2S,3R)-2-methyl-1-azabicyclo[2.2.2]oct-3-yl]-4-(4-acetylpyridin-2-yloxy)-benzamide; N-[(2S,3R)-2-methyl-1-azabicyclo[2.2.2]oct-3-yl]-4-(4-acetaminopyridin-2-yloxy)-benzamide; N-[(2S,3R)-2-methyl-1-azabicyclo[2.2.2]oct-3-yl]-4-(4-cyanopyridin-2-yloxy)-benzamide; N-[(2S,3R)-2-methyl-1-azabicyclo[2.2.2]oct-3-yl]-4-(4-morpholin-4-yl-pyridin-2-yloxy)-benzamide; N-[(2S,3R)-2-methyl-1-azabicyclo[2.2.2]oct-3-yl]-4-(6-methylpyrrolridin-2-yloxy)-benzamide; N-[(2S,3R)-2-methyl-1-azabicyclo[2.2.2]oct-3-yl]-4-(6--chloropyridin-2-yloxy)-benzamide; N-[(2S,3R)-2-methyl-1-azabicyclo[2.2.2]oct-3-yl]-4-(6-methoxypyridin-2-yloxy)-benzamide; N-[(2S,3R)-2-methyl-1-azabicyclo[2.2.2]oct-3-yl]-4-(6-trifluoromethylpyrrolridin-2-yloxy)-benzamide; N-[(2S,3R)-2-methyl-1-azabicyclo[2.2.2]oct-3-yl]-4-(6-acetylpyridin-2-yloxy)-benzamide; N-[(2S,3R)-2-methyl-1-azabicyclo[2.2.2]oct-3-yl]-4-(6-acetaminopyridin-2-yloxy)-benzamide; N-[(2S,3R)-2-methyl-1-azabicyclo[2.2.2]oct-3-yl]-4-(6-cyanopyridin-2-yloxy)-benzamide; N-[(2S,3R)-2-methyl-1-azabicyclo[2.2.2]oct-3-yl]-4-(6-morpholin-4-yl-pyridin-2-yloxy)-benzamide; N-[(2S,3R)-2-methyl-1-azabicyclo[2.2.2]oct-3-yl]-4-(5-methylpyrrolridin-3-yloxy)-benzamide; N-[(2S,3R)-2-methyl-1-azabicyclo[2.2.2]oct-3-yl]-4-(5--chloropyridin-3-yloxy)-benzamide; N-[(2S,3R)-2-methyl-1-azabicyclo[2.2.2]oct-3-yl]-4-(5-methoxypyridin-3-yloxy)-benzamide; N-[(2S,3R)-2-methyl-1-azabicyclo[2.2.2]oct-3-yl]-4-(5-trifluoromethylpyrrolridin-3-yloxy)-benzamide; N-[(2S,3R)-2-methyl-1-azabicyclo[2.2.2]oct-3-yl]-4-(5-acetylpyridin-3-yloxy)-benzamide; N-[(2S,3R)-2-methyl-1-azabicyclo[2.2.2]oct-3-yl]-4-(5-acetaminopyridin-3-yloxy)-benzamide; N-[(2S,3R)-2-methyl-1-azabicyclo[2.2.2]oct-3-yl]-4-(5-cyanopyridin-3-yloxy)-benzamide; N-[(2S,3R)-2-methyl-1-azabicyclo[2.2.2]oct-3-yl]-4-(5-morpholin-4-yl-pyridin-3-yloxy)-benzamide; N-[(2S,3R)-2-methyl-1-azabicyclo[2.2.2]oct-3-yl]-4-(2--chloropyridin-3-yloxy)-benzamide; N-[(2S,3R)-2-methyl-1-azabicyclo[2.2.2]oct-3-yl]-4-(4--chloropyridin-3-yloxy)-benzamide; N-[(2S,3R)-2-methyl-1-azabicyclo[2.2.2]oct-3-yl]-4-(3--chloropyridin-4-yloxy)-benzamide; N-[(2S,3R)-2-methyl-1-azabicyclo[2.2.2]oct-3-yl]-4-(3--chloropyridin-2-yloxy)-benzamide; N-[(2S,3R)-2-methyl-1-azabicyclo[2.2.2]oct-3-yl]-4-(6-methylpyrrolridin-3-ylsulfanyl)-benzamide; N-[(2S,3R)-2-methyl-1-azabicyclo[2.2.2]oct-3-yl]-4-(6--chloropyridin-3-ylsulfanyl)-benzamide; N-[(2S,3R)-2-methyl-1-azabicyclo[2.2.2]oct-3-yl]-4-(6-methoxypyridin-3-ylsulfanyl)-benzamide; N-[(2S,3R)-2-methyl-1-azabicyclo[2.2.2]oct-3-yl]-4-(6-trifluoromethylpyrrolridin-3-ylsulfanyl)-benzamide; N-[(2S,3R)-2-methyl-1-azabicyclo[2.2.2]oct-3-yl]-4-(6-acetylpyridin-3-ylsulfanyl)-benzamide; N-[(2S,3R)-2-methyl-1-azabicyclo[2.2.2]oct-3-yl]-4-(6-acetaminopyridin-3-ylsulfanyl)-benzamide; N-[(2S,3R)-2-methyl-1-azabicyclo[2.2.2]oct-3-yl]-4-(6-cyanopyridin-3-ylsulfanyl)-benzamide; N-[(2S,3R)-2-methyl-1-azabicyclo[2.2.2]oct-3-yl]-4-(6-morpholin-4-yl-pyridin-3-ylsulfanyl)-benzamide; N-[(2S,3R)-2-methyl-1-azabicyclo[2.2.2]oct-3-yl]-4-(2-methylpyrrolridin-4-ylsulfanyl)-benzamide; N-[(2S,3R)-2-methyl-1-azabicyclo[2.2.2]oct-3-yl]-4-(2--chloropyridin-4-ylsulfanyl)-benzamide; N-[(2S,3R)-2- methyl-1-azabicyclo[2.2.2]oct-3-yl]-4-(2-methoxypyridin-4-ylsulfanyl)-benzamide; N-[(2S,3R)-2-methyl-1-azabicyclo[2.2.2]oct-3-yl]-4-(2-trifluoromethylpyrrolridin-4-ylsulfanyl)-benzamide; N-[(2S,3R)-2-methyl-1-azabicyclo[2.2.2]oct-3-yl]-4-(2-acetylpyridin-4-ylsulfanyl)-benzamide; N-[(2S,3R)-2-methyl-1-azabicyclo[2.2.2]oct-3-yl]-4-(2-acetaminopyridin-4-ylsulfanyl)-benzamide; N-[(2S,3R)-2-methyl-1-azabicyclo[2.2.2]oct-3-yl]-4-(2-cyanopyridin-4-ylsulfanyl)-benzamide; N-[(2S,3R)-2-methyl-1-azabicyclo[2.2.2]oct-3-yl]-4-(2-morpholin-4-yl-pyridin-4-ylsulfanyl)-benzamide; N-[(2S,3R)-2-methyl-1-azabicyclo[2.2.2]oct-3-yl]-4-(5-methylpyrrolridin-2-ylsulfanyl)-benzamide; N-[(2S,3R)-2-methyl-1-azabicyclo[2.2.2]oct-3-yl]-4-(5--chloropyridin-2-ylsulfanyl)-benzamide; N-[(2S,3R)-2-methyl-1-azabicyclo[2.2.2]oct-3-yl]-4-(5-methoxypyridin-2-ylsulfanyl)-benzamide; N-[(2S,3R)-2-methyl-1-azabicyclo[2.2.2]oct-3-yl]-4-(5-trifluoromethylpyrrolridin-2-ylsulfanyl)-benzamide; N-[(2S,3R)-2-methyl-1-azabicyclo[2.2.2]oct-3-yl]-4-(5-acetylpyridin-2-ylsulfanyl)-benzamide; N-[(2S,3R)-2-methyl-1-azabicyclo[2.2.2]oct-3-yl]-4-(5-acetaminopyridin-2-ylsulfanyl)-benzamide; N-[(2S,3R)-2-methyl-1-azabicyclo[2.2.2]oct-3-yl]-4-(5-cyanopyridin-2-ylsulfanyl)-benzamide; N-[(2S,3R)-2-methyl-1-azabicyclo[2.2.2]oct-3-yl]-4-(5-morpholin-4-yl-pyridin-2-ylsulfanyl)-benzamide; N-[(2S,3R)-2-methyl-1-azabicyclo[2.2.2]oct-3-yl]-4-(4-methylpyrrolridin-2-ylsulfanyl)-benzamide; N-[(2S,3R)-2-methyl-1-azabicyclo[2.2.2]oct-3-yl]-4-(4--chloropyridin-2-ylsulfanyl)-benzamide; N-[(2S,3R)-2-methyl-1-azabicyclo[2.2.2]oct-3-yl]-4-(4-methoxypyridin-2-ylsulfanyl)-benzamide; N-[(2S,3R)-2-methyl-1-azabicyclo[2.2.2]oct-3-yl]-4-(4-trifluoromethylpyrrolridin-2-ylsulfanyl)-benzamide; N-[(2S,3R)-2-methyl-1-azabicyclo[2.2.2]oct-3-yl]-4-(4-acetylpyridin-2-ylsulfanyl)-benzamide; N-[(2S,3R)-2-methyl-1-azabicyclo[2.2.2]oct-3-yl]-4-(4-acetaminopyridin-2-ylsulfanyl)-benzamide; N-[(2S,3R)-2-methyl-1-azabicyclo[2.2.2]oct-3-yl]-4-(4-cyanopyridin-2-ylsulfanyl)-benzamide; N-[(2S,3R)-2-methyl-1-azabicyclo[2.2.2]oct-3-yl]-4-(4-morpholin-4-yl-pyridin-2-ylsulfanyl)-benzamide; N-[(2S,3R)-2-methyl-1-azabicyclo[2.2.2]oct-3-yl]-4-(6-methylpyrrolridin-2-ylsulfanyl)-benzamide; N-[(2S,3R)-2-methyl-1-azabicyclo[2.2.2]oct-3-yl]-4-(6--chloropyridin-2-ylsulfanyl)-benzamide; N-[(2S,3R)-2-methyl-1-azabicyclo[2.2.2]oct-3-yl]-4-(6-methoxypyridin-2-ylsulfanyl)-benzamide; N-[(2S,3R)-2-methyl-1-azabicyclo[2.2.2]oct-3-yl]-4-(6-trifluoromethylpyrrolridin-2-ylsulfanyl)-benzamide; N-[(2S,3R)-2-methyl-1-azabicyclo[2.2.2]oct-3-yl]-4-(6-acetylpyridin-2-ylsulfanyl)-benzamide; N-[(2S,3R)-2-methyl-1-azabicyclo[2.2.2]oct-3-yl]-4-(6-acetaminopyridin-2-ylsulfanyl)-benzamide; N-[(2S,3R)-2-methyl-1-azabicyclo[2.2.2]oct-3-yl]-4-(6-cyanopyridin-2-ylsulfanyl)-benzamide; N-[(2S,3R)-2-methyl-1-azabicyclo[2.2.2]oct-3-yl]-4-(6-morpholin-4-yl-pyridin-2-ylsulfanyl)-benzamide; N-[(2S,3R)-2-methyl-1-azabicyclo[2.2.2]oct-3-yl]-4-(5-methylpyrrolridin-3-ylsulfanyl)-benzamide; N-[(2S,3R)-2-methyl-1-azabicyclo[2.2.2]oct-3-yl]-4-(5--chloropyridin-3-ylsulfanyl)-benzamide; N-[(2S,3R)-2-methyl-1-azabicyclo[2.2.2]oct-3-yl]-4-(5-methoxypyridin-3-ylsulfanyl)-benzamide; N-[(2S,3R)-2-methyl-1-azabicyclo[2.2.2]oct-3-yl]-4-(5-trifluoromethylpyrrolridin-3-ylsulfanyl)-benzamide; N-[(2S,3R)-2-methyl-1-azabicyclo[2.2.2]oct-3-yl]-4-(5-acetylpyridin-3-ylsulfanyl)-benzamide; N-[(2S,3R)-2-methyl-1-azabicyclo[2.2.2]oct-3-yl]-4-(5-acetaminopyridin-3-ylsulfanyl)-benzamide; N-[(2S,3R)-2-methyl-1-azabicyclo[2.2.2]oct-3-yl]-4-(5-cyanopyridin-3-ylsulfanyl)-benzamide; N-[(2S,3R)-2-methyl-1-azabicyclo[2.2.2]oct-3-yl]-4-(5-morpholin-4-yl-pyridin-3-ylsulfanyl)-benzamide; N-[(2S,3R)-2-methyl-1-azabicyclo[2.2.2]oct-3-yl]-4-(2--chloropyridin-3-ylsulfanyl)-benzamide; N-[(2S,3R)-2-methyl-1-azabicyclo[2.2.2]oct-3-yl]-4-(4--chloropyridin-3-ylsulfanyl)-benzamide; N-[(2S,3R)-2-methyl-1-azabicyclo[2.2.2]oct-3-yl]-4-(3--chloropyridin-4-ylsulfanyl)-benzamide; N-[(2S,3R)-2-methyl-1-azabicyclo[2.2.2]oct-3-yl]-4-(3--chloropyridin-2-ylsulfanyl)-benzamide; or a pharmaceutically acceptable salt thereof.

58. The method according to claim 57, wherein said compound(s) is(are) administered rectally, topically, orally, sublingually, or parenterally.

59. The method according to claim 57, wherein said compound(s) is(are) administered from about 0.001 to about 100 mg/kg of body weight of said mammal per day.

60. The method according to claim 57, wherein said compound(s) is(are) administered from about 0. 1 to about 50 mg/kg of body weight of said mammal per day.

* * * * *